United States Patent [19]
Barnett et al.

[11] Patent Number: 6,103,487
[45] Date of Patent: Aug. 15, 2000

[54] METHOD OF TREATING CANCER

[75] Inventors: Stanley F. Barnett, North Wales; David C. Heimbrook, Fleetwood; Hans E. Huber, Lansdale; Denis R. Patrick, Chalfont, all of Pa.

[73] Assignee: Merck & Co., Inc., Rahway, N.J.

[21] Appl. No.: 09/140,557

[22] Filed: Aug. 26, 1998

Related U.S. Application Data

[60] Provisional application No. 60/057,340, Aug. 27, 1997.

[51] Int. Cl.$^7$ ........................................ C12Q 1/48
[52] U.S. Cl. .................... 435/15; 435/7.72; 435/193; 436/64; 436/71; 436/86; 436/100; 436/101; 436/102; 436/103; 436/182; 436/815
[58] Field of Search .................... 435/7.72, 15, 193; 436/64, 71, 86, 100, 101, 102, 103, 182, 815

[56] References Cited

U.S. PATENT DOCUMENTS 5,185,248   2/1993   Barbacid et al. ........................ 435/15

FOREIGN PATENT DOCUMENTS

| WO95/20396 | 8/1995 | WIPO . |
| WO95/20651 | 8/1995 | WIPO . |
| WO 96/30343 | 10/1996 | WIPO . |
| WO97/38664 | 10/1997 | WIPO . |

OTHER PUBLICATIONS

Biochemistry, vol. 27, pp. 3613–3617 (1988), by M. DiGregorio, et al.
Biochemistry, vol. 7, No. 11, pp. 3997–4004 (1968), by W. B. Anderson, et al.
Biochemistry, vol. 9, No. 3, pp. 610–616 (1970), by R. N. Horne, et al.
Biochemistry, vol. 7, No. 4, pp. 1479–1485 (1968), by W. B. Anderson, et al.
Biochim Biophys. Acta, vol. 242, pp. 1–13 (1971), by R. N. Horne, et al.
TIBS, vol. 15, pp. 6–10, (1990), by M. Chabre.
Cancer Research, vol. 57, pp. 1846–1850 (1997), by K. Miquel, et al.
Bioorg & Med. Chem., vol. 4, No. 9, pp. 1537–1543 (1996), by J. D. Scholten, et al.
Cancer Research, vol. 55, pp. 3295–3304 (1995), by M. B. Dalton, et al.
J. of Biol. Chem., vol. 266, No. 22, pp. 14603–14610 (1991), by T. F. McGuire, et al.
J. of Biol. Chem., vol. 271, No. 44, pp. 27402–27407 (1996), by T. F. McGuire, et al.
J. of Biol. Chem., vol. 270, No. 45, pp. 26770–26773 (1995), by E. C. Lerner, et al.
J. of Biol. Chem., vol. 272, No. 29, pp. 18077–18081 (1997), by J. D. Scholten, et al.
Science, vol. 260, pp. 1934–1937 (1993), by N. E. Kohl, et al.
J. of Biol. Chem., vol. 266, No. 22, pp. 14603–14610 (1991), by S. L. Moores, et al.
J. of Biol. Chem., vol. 263, No. 9, pp. 4056–4058 (1988), by R. A. Pfuetzner, et al.
J. Am. Chem. Soc., vol. 111, pp. 3734–3739 (1989), by C. Dale Poulter, et al.
Eur. J. Biochem., vol. 218, pp. 523–528 (1993), by R. A. Pfuetzner, et al.
Eur. J. Biochem., vol. 218, pp. 529–534 (1993), by W. W–C. Chan, et al.
Biochemical Pharma, vol. 54, pp. 113–120 (1997), by Z Ren, et al.
J. of Biol. Chem., vol. 272, No. 22, pp. 14459–14464 (1997), by D. B. Whyte, et al.
J. of Biol. Chem., vol. 272, No. 22, pp. 14093–14097 (1997), by C. A. Rowell, et al.

*Primary Examiner*—Frederick Krass
*Attorney, Agent, or Firm*—David A. Muthard; Mark R. Daniel

[57] ABSTRACT

The instant invention provides for a method of inhibiting prenyl-protein transferases and treating cancer which comprises administering to a mammal a prenyl-protein transferase inhibitor which is efficacious in vivo as an inhibitor of geranylgeranyl-protein transferase type I (GGTase-I). The invention also provides for a method of inhibiting farnesyl-protein transferase and geranylgeranyl-protein transferase type I by administering a compound that is a dual inhibitor of both of those prenyl-protein transferases. The invention also provides for a method of identifying such a compound, the method comprising a modified inhibitory assay that incorporates a modulator anion that alters the in vitro potency of prenyl-protein transferase inhibitors in a way that predicts their potency in vivo, thus providing convenient identification of compounds that possess such in vivo activity.

11 Claims, 2 Drawing Sheets

SEQUENCE LISTING

<160> NUMBER OF SEQ ID NOS: 15

<210> SEQ ID NO 1
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 1

Cys Val Ile Met
1

<210> SEQ ID NO 2
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 2

Cys Val Leu Leu
1

<210> SEQ ID NO 3
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

```
<400> SEQUENCE: 3

Cys Val Val Met
1

<210> SEQ ID NO 4
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 4

Cys Ile Ile Met
1

<210> SEQ ID NO 5
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 5

Cys Leu Leu Leu
1

<210> SEQ ID NO 6
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 6

Cys Gln Leu Leu
1

<210> SEQ ID NO 7
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 7

Cys Ser Ile Met
1

<210> SEQ ID NO 8
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 8

Cys Ala Ile Met
1

<210> SEQ ID NO 9
<211> LENGTH: 4
<212> TYPE: PRT
```

```
<213> ORGANISM: Artificial Sequence
<220> FEATURE:
<223> OTHER INFORMATION: C-terminus CAAX sequence of prenyl-protein
      transferase substrate

<400> SEQUENCE: 9

Cys Lys Val Leu
1

<210> SEQ ID NO 10
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 10

Cys Leu Ile Met
1

<210> SEQ ID NO 11
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 11

Cys Val Leu Ser
1

<210> SEQ ID NO 12
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 12

Cys Ala Ile Leu
1

<210> SEQ ID NO 13
<211> LENGTH: 15
<212> TYPE: PRT
<213> ORGANISM: Artificial Sequence
<220> FEATURE:
<223> OTHER INFORMATION: synthesized peptide substrate for
      geranylgeranyl-protein transferase type I

<400> SEQUENCE: 13

Gly Lys Lys Lys Lys Lys Lys Ser Lys Thr Lys Cys Val Ile Met
1               5                   10                  15

<210> SEQ ID NO 14
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 14

Cys Val Ile Leu
1
```

```
<210> SEQ ID NO 15
<211> LENGTH: 4
<212> TYPE: PRT
<213> ORGANISM: Artificial Sequence
<220> FEATURE:
<223> OTHER INFORMATION: C-terminus CAAX sequence of prenyl-protein
      transferase substrate

<400> SEQUENCE: 15

Cys Asn Ile Gln
```

METHOD OF TREATING CANCER

This application claims the benefit of U.S. Provisional Application No. 60/057,340, filed Aug. 27, 1997.

BACKGROUND OF THE INVENTION

The present invention relates to a method of treating cancer which utilizes prenyl-protein transferase inhibitors which are efficacious in vivo as inhibitors of geranylgeranyl-protein transferase type I (GGTase-I). The invention also relates to a method for identifying such prenyl-protein transferase inhibitors.

Prenylation of proteins by prenyl-protein transferases represents a class of post-translational modification (Glomset, J. A., Gelb, M. H., and Farnsworth, C. C. (1990), Trends Biochem. Sci. 15, 139–142; Maltese, W. A. (1990), FASEB J. 4, 3319–3328). This modification typically is required for the membrane localization and function of these proteins. Prenylated proteins share characteristic C-terminal sequences including CAAX (C, Cys; A, an aliphatic amino acid; X, another amino acid), XXCC, or XCXC. Three post-translational processing steps have been described for proteins having a C-terminal CAAX sequence: addition of either a 15 carbon (farnesyl) or 20 carbon (geranylgeranyl) isoprenoid to the Cys residue, proteolytic cleavage of the last 3 amino acids, and methylation of the new C-terminal carboxylate (Cox, A. D. and Der, C. J. (1992a), *Critical Rev. Oncogenesis* 3:365–400; Newman, C. M. H. and Magee, A. I. (1993), *Biochim. Biophys. Acta* 1155:79–96). Some proteins may also have a fourth modification: palmitoylation of one or two Cys residues N-terminal to the farnesylated Cys. While some mammalian cell proteins terminating in XCXC are carboxymethylated, it is not clear whether carboxy methylation follows prenylation of proteins terminating with a XXCC motif (Clarke, S. (1992), Annu. Rev. Biochem. 61, 355–386). For all of the prenylated proteins, addition of the isoprenoid is the first step and is required for the subsequent steps (Cox, A. D. and Der, C. J. (1992a), *Critical Rev. Oncogenesis* 3:365–400; Cox, A. D. and Der, C. J. (1992b) *Current Opinion Cell Biol.* 4:1008–1016).

Three enzymes have been described that catalyze protein prenylation: farnesyl-protein transferase (FPTase), geranylgeranyl-protein transferase type I (GGPTase-I), and geranylgeranyl-protein transferase type-II (GGPTase-II, also called Rab GGPTase). These enzymes are found in both yeast and mammalian cells (Clarke, 1992; Schafer, W. R. and Rine, J. (1992) *Annu. Rev. Genet.* 30:209–237). Each of these enzymes selectively uses farnesyl diphosphate or geranylgeranyl diphosphate as the isoprenoid donor and selectively recognizes the protein substrate. FPTase farnesylates CAAX-containing proteins that end with Ser, Met, Cys, Gln or Ala. For FPTase, CAAX tetrapeptides comprise the minimum region required for interaction of the protein substrate with the enzyme. The enzymological characterization of these three enzymes has demonstrated that it is possible to selectively inhibit one with little inhibitory effect on the others (Moores, S. L., Schaber, M. D., Mosser, S. D., Rands, E., O'Hara, M. B., Garsky, V. M., Marshall, M. S., Pompliano, D. L., and Gibbs, J. B., *J. Biol. Chem.*, 266:17438 (1991), U.S. Pat. No. 5,470,832).

The prenylation reactions have been shown genetically to be essential for the function of a variety of proteins (Clarke, 1992; Cox and Der, 1992a; Gibbs, J. B. (1991). *Cell* 65: 1–4; Newman and Magee, 1993; Schafer and Rine, 1992). This requirement often is demonstrated by mutating the CAAX Cys acceptors so that the proteins can no longer be prenylated. The resulting proteins are devoid of their central biological activity. These studies provide a genetic "proof of principle" indicating that inhibitors of prenylation can alter the physiological responses regulated by prenylated proteins.

The Ras protein is part of a signaling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation, Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Activation of Ras leads to activation of multiple intracellular signal transduction pathways, including the MAP Kinase pathway and the Rho/Rac pathway (Joneson et al., Science 271:810–812).

Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

The Ras protein is one of several proteins that are known to undergo post-translational modification. Farnesyl-protein transferase utilizes farnesyl pyrophosphate to covalently modify the Cys thiol group of the Ras CAAX box with a farnesyl group (Reiss et al., *Cell,* 62:81–88 (1990); Schaber et al., *J. Biol. Chem.,* 265:14701–14704 (1990); Schafer et al., *Science,* 249:1133–1139 (1990); Manne et al., *Proc. Natl. Acad. Sci USA,* 87:7541–7545 (1990)).

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa-Aaa-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)).

Other farnesylated proteins include the Ras-related GTP-binding proteins such as RhoB, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibitors of farnesyl-protein transferase (FPTase) have been described in two general classes. The first class includes analogs of farnesyl diphosphate (FPP), while the second is related to protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS,* 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science* 260:1934–1937 (1993); Graham, et al., *J. Med. Chem.*, 37, 725 (1994)).

Mammalian cells express four types of Ras proteins (H-, N-, K4A-, and K4B-Ras) among which K4B-Ras is the most frequently mutated form of Ras in human cancers. The genes that encode these proteins are abbreviated H-ras, N-ras, K4A-ras and K4B-ras respectively. H-ras is an abbreviation for Harvey-ras. K4A-ras and K4B-ras are abbreviations for the Kirsten splice variants of ras that contain the 4A and 4B exons, respectively. Inhibition of farnesyl-protein transferase has been shown to block the growth of H-ras-transformed cells in soft agar and to modify other aspects of their transformed phenotype. It has also been demonstrated that certain inhibitors of farnesyl-protein transferase selectively block the processing of the H-Ras oncoprotein intracellularly (N. E. Kohl et al., *Science,* 260:1934–1937 (1993) and G. L. James et al., *Science* 260:1937–1942 (1993). Recently, it has been shown that an inhibitor of farnesyl-protein transferase blocks the growth of H-ras-dependent tumors in nude mice (N. E. Kohl et al., *Proc. Natl. Acad. Sci U.S.A.*, 91:9141–9145 (1994) and induces regression of mammary and salivary carcinomas in H-ras transgenic mice (N. E. Kohl et al., *Nature Medicine,* 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Inhibition of farnesyl pyrophosphate biosynthesis by inhibiting HMG-CoA reductase blocks Ras membrane localization in cultured cells.

It has been disclosed that the lysine-rich region and terminal CVIM sequence of the C-terminus of K4B-Ras confer resistance to inhibition of the cellular processing of that protein by certain selective FPTase inhibitors. (James, et al., *J. Biol. Chem.* 270, 6221 (1995)) Those FPTase inhibitors were effective in inhibiting the processing of H-Ras proteins. James et al., suggested that prenylation of the K4B-Ras protein by GGTase contributed to the resistance to the selective FPTase inhibitors. (Zhang et al, *J. Biol. Chem.* 272 :10232–239 (1997); Rowell et al, *J. Biol. Chem.* 272 :14093–14097 (1997); Whyte et al, *J. Biol. Chem.* 272 :14459–14464 (1997)).

Several groups of scientists have recently disclosed compounds that are non-selective FPTase/GGTase inhibitors. (Nagasu et al. *Cancer Research,* 55:5310–5314 (1995); PCT application WO 95/25086).

Recently, synergy between certain anions and farnesyl-diphosphate competitive inhibitors of FPTase has been disclosed (J. D. Scholten et al. *J. Biol. Chem.* 272:18077–18081 (1997)).

It is the object of the present invention to provide a method of inhibiting prenyl-protein transferases and treating cancer which utilizes a compound which is a prenyl-protein transferase inhibitor, and which is efficacious in vivo as an inhibitor of the growth of cancer cells characterized by a mutated K4B-Ras protein.

A composition which comprises such an inhibitor compound is used in the present invention to treat cancer.

It is also the object of the instant invention to provide a method for identifying a prenyl-protein transferase inhibitor which is efficacious in vivo as an inhibitor of geranylgeranyl-protein transferase type I (GGTase-I), also known as CAAX GGTase.

SUMMARY OF THE INVENTION

The instant invention provides for a method of inhibiting prenyl-protein transferases and treating cancer which comprises administering to a mammal a prenyl-protein transferase inhibitor which is efficacious in vivo as an inhibitor of geranylgeranyl-protein transferase type I (GGTase-I). The invention also provides for a method of inhibiting farnesyl-protein transferase and geranylgeranyl-protein transferase type I by administering a compound that is a dual inhibitor of both of those prenyl-protein transferases. The invention also provides for a method of identifying such a compound, the method comprising a modified inhibitory assay that incorporates a modulator anion that alters the in vitro potency of prenyl-protein transferase inhibitors in a way that predicts their potency in vivo, thus providing convenient identification of compounds that possess such in vivo activity.

BRIEF DESCRIPTION OF THE FIGURES

FIG. 1A: Titrations of Compound 1 were performed at various fixed concentrations of β-glycerol phosphate. FIG. 1B: Compound 1 $IC_{50}$'s were re-plotted as a function of the concentration of glycerophosphate.

DETAILED DESCRIPTION OF THE INVENTION

Figure 1A:
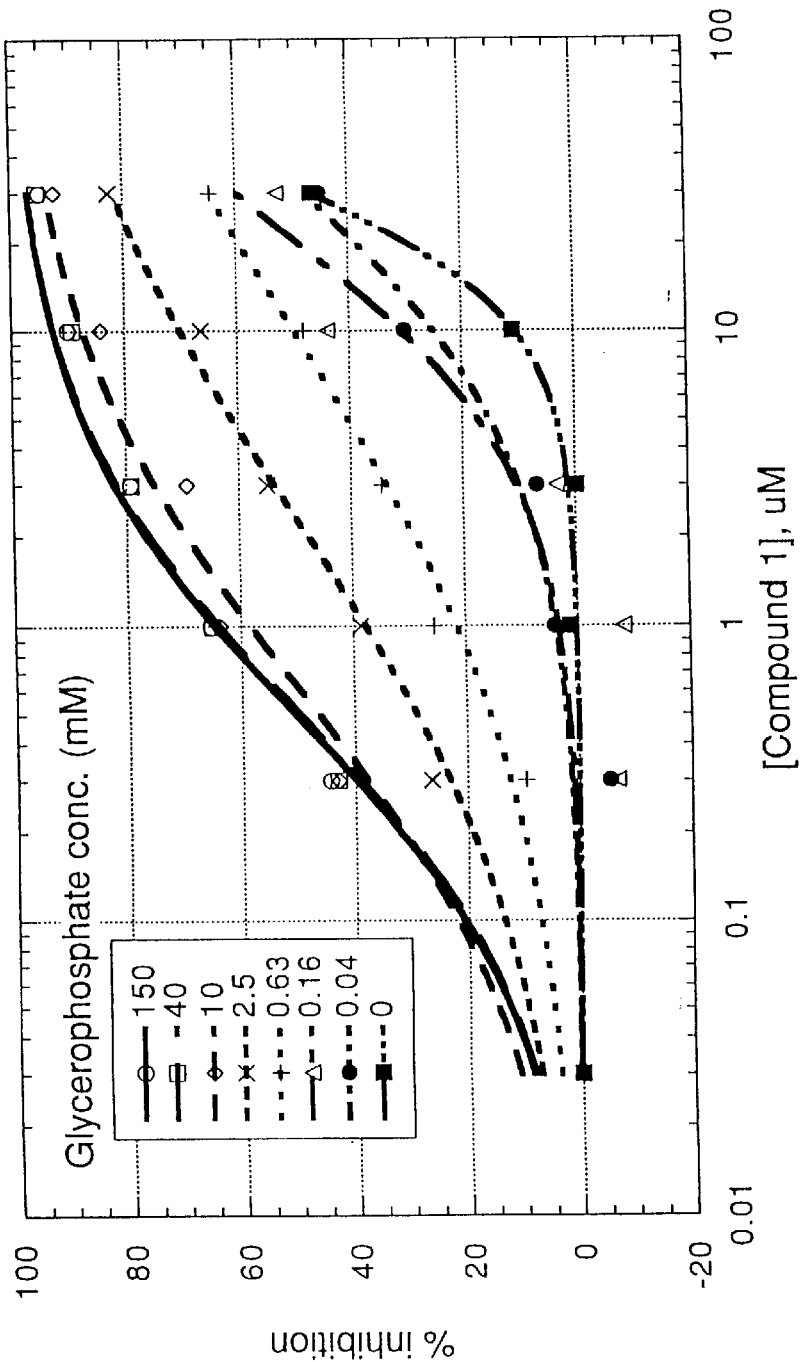
FIGS. 1A and 1B: Effect of β-glycerol phosphate on $IC_{50}$ of Compound 1 in GGTase-I reaction Effect of β-glycerol phosphate on $IC_{50}$ of Compound 1 in GGTase-I reaction using recombinant enzyme and K4B-Ras protein substrate is illustrated.
Figure 1B:
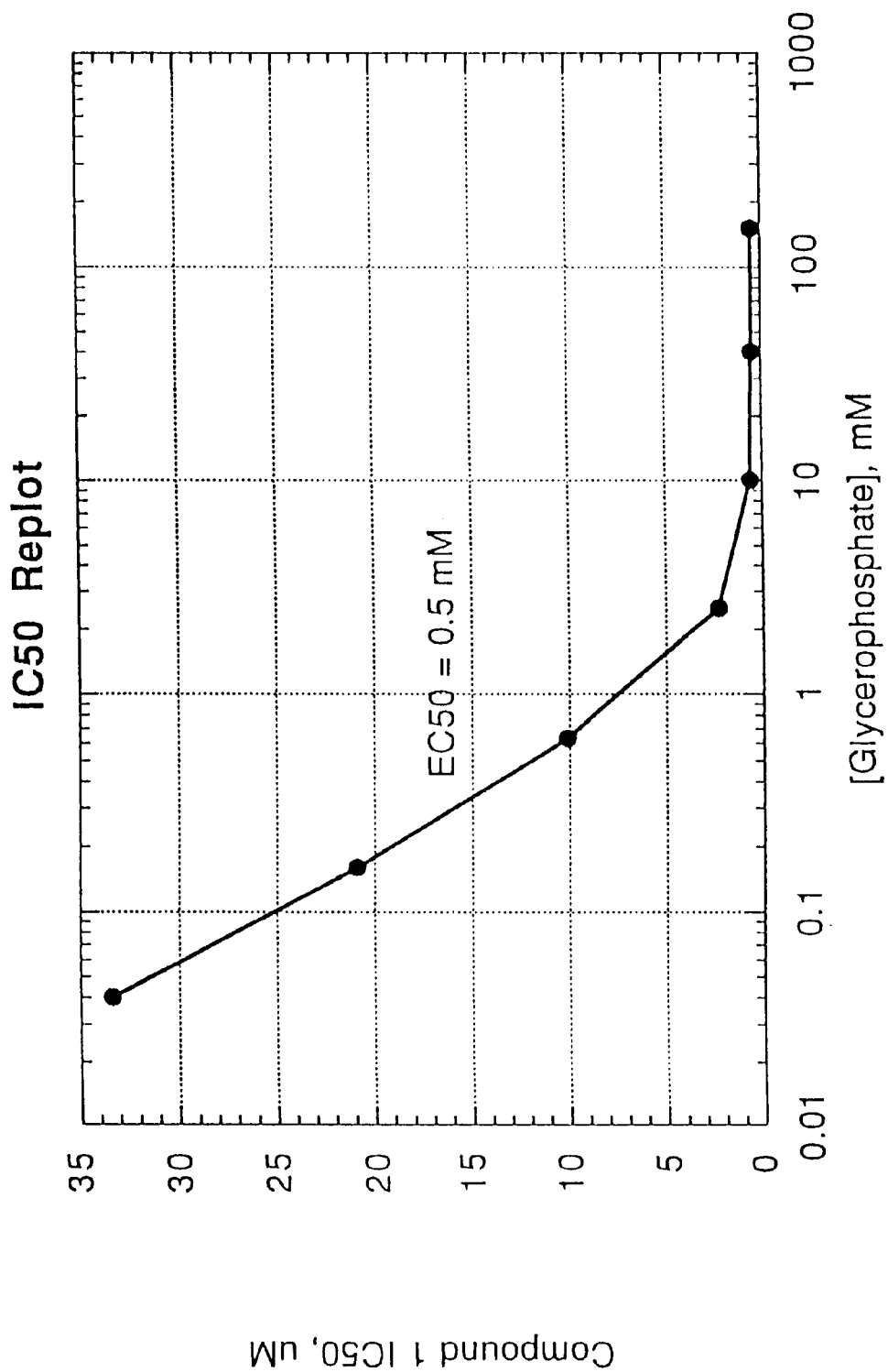

The present invention relates to a method of inhibiting prenyl-protein transferases which comprises administering to a mammal in need thereof a pharmaceutically effective amount of a prenyl-protein transferase inhibitor which is efficacious in vivo as an inhibitor of geranylgeranyl-protein transferase type I (GGTase-I). Such an inhibitor is characterized by:

a) an $IC_{50}$ (a measurement of in vitro inhibitory activity) of less than about 5 μM against transfer of a geranylgeranyl residue to a protein or peptide substrate comprising a $CAAX^G$ motif by geranylgeranyl-protein transferase type I in the presence of a modulating anion.

The inhibitor used in the instant method may be further characterized by one or both:

b) an $IC_{50}$ (a measurement of in vitro inhibitory activity) of less than about 1 μM against transfer of a farnesyl residue to a protein or peptide substrate comprising a $CAAX^F$ motif by farnesyl-protein transferase; and c) an $IC_{50}$ (a measurement of in vitro inhibitory activity) of less than about 100 nM against the anchorage independent growth of H-ras-transformed mammalian fibroblasts.

The inhibitor compounds useful in the instant method are also useful in the treatment of cancer and other proliferative disorders in mammals in need thereof. In an embodiment of the invention the inhibitor compounds have inhibitory concentrations ($IC_{50}$) of less than about 1 μM against GGTase-I in the presence of a modulating anion. Preferably such compounds have inhibitory concentrations ($IC_{50}$) of less than about 500 nM against GGTase-I in the presence of a modulating anion. Most preferably, such compounds have an $IC_{50}$ of less than 250 nM against GGTase-I in the presence of a modulating anion. A preferred cancer is one which is characterized by mutated K4B-Ras.

In another embodiment, the compound useful in the methods of the instant inventions is characterized by an $IC_{50}$ (a measurement of in vitro inhibitory activity) of less than about 500 nM, but greater than about 5 nM against transfer of a geranylgeranyl residue to a protein or peptide substrate comprising a $CAAX^G$ motif by geranylgeranyl-protein transferase type I in the presence of a modulating anion.

Preferably, the prenyl-protein transferases that are being inhibited by the instant method are both farnesyl-protein transferase and geranylgeranyl-protein transferase type I.

The invention also relates to a method of identifying a prenyl-protein transferase inhibitor which is efficacious in vivo as an inhibitor of geranylgeranyl-protein transferase type I (GGTase-I). The instant method comprises the step of determining the inhibitory activity of a test compound against GGTase-I in a novel modified in vitro enzymatic assay.

The modified GGTase-I inhibition assay of the instant invention comprises an anion at a concentration that modulates the in vitro GGTase-I inhibitory potency of the prenyl-protein transferase inhibitor. In an embodiment of the instant methods, the prenyl-protein transferase inhibitor which is efficacious in vivo as an inhibitor of GGTase-I is characterized by an increased potency in vitro against GGTase-I in the instant modified assay when compared to its potency in the absence of the modulating anion. The ratio of the inhibitory activities in the presence vs the absence of the modulating anion may also provide useful mechanistic information on the interaction of the inhibitory compound with GGTase-I.

In this embodiment of the instant invention, with regard to the compound utilized in the instant methods of inhibiting farnesyl-protein transferase and GGTase-I and treating cancer, the $IC_{50}$ (a measurement of in vitro inhibitory activity) of the compound against transfer of a geranylgeranyl residue to a protein or peptide substrate comprising a $CAAX^G$ motif by geranylgeranyl-protein transferase type I in the presence of a modulating anion is greater than 5 fold lower than the $IC_{50}$ against said transfer of a geranylgeranyl residue in the absence of a modulating anion. It is more preferred in this embodiment that the compound in the presence of a modulating anion has greater than 7 fold lower $IC_{50}$. It is more preferred that the compound in the presence of a modulating anion has greater than 10 fold lower $IC_{50}$. It is still more preferred in this embodiment that the compound in the presence of a modulating anion has greater than 25 fold lower $IC_{50}$. It is most preferred in this embodiment that the compound in the presence of a modulating anion has greater than 150 fold lower $IC_{50}$.

In another embodiment of the instant invention, with regard to the compound utilized in the instant methods of inhibiting farnesyl-protein transferase and GGTase-I and treating cancer, the $IC_{50}$ (a measurement of in vitro inhibitory activity) of the compound against transfer of a geranylgeranyl residue to a protein or peptide substrate comprising a $CAAX^G$ motif by geranylgeranyl-protein transferase type I in the presence of a modulating anion is 5 fold or less lower than the $IC_{50}$ against said transfer of a geranylgeranyl residue in the absence of a modulating anion.

In particular, the assay for identifying compounds that inhibit geranylgeranyl-protein transferase type I activity (also referred to as the modified in vitro GGTase-I assay), comprises the steps of:

a) reacting a protein or peptide substrate comprising a $CAAX^G$ motif with geranylgeranyl pyrophosphate and geranylgeranyl-protein transferase type I in the presence of a test compound and further in the presence of a modulating anion;

b) detecting whether the geranylgeranyl residue is incorporated into the protein or peptide substrate, in which the ability of the test compound to inhibit geranylgeranyl-protein transferase type I activity is indicated by a decrease in the incorporation of the geranylgeranyl residue into the protein or peptide substrate as compared to the amount of the geranylgeranyl residue incorporated into the protein or peptide substrate in the absence of the test substance.

The modulating anion may be selected from any type of molecule containing an anion moiety. Preferably the modulating anion is selected from a phosphate or sulfate containing anion. Particular examples of modulating anions useful in the instant GGTase-I inhibition assay include adenosine 5'-triphosphate (ATP), 2'-deoxyadenosine 5'-triphosphate (dATP), 2'-deoxycytosine 5'-triphosphate (dCTP), β-glycerol phosphate, pyrophosphate, guanosine 5'-triphosphate (GTP), 2'-deoxyguanosine 5'-triphosphate (dGTP), uridine 5'-triphosphate, dithiophosphate, 3'-deoxythymidine 5'-triphosphate, tripolyphosphate, D-myo-inositol 1,4,5-triphosphate, chloride, guanosine 5'-monophosphate, 2'-deoxyguanosine 5'-monophosphate, orthophosphate, formycin A, inosine diphosphate, trimetaphosphate, sulfate and the like. Preferably, the modulating anion is selected from adenosine 5'-triphosphate, 2'-deoxyadenosine 5'-triphosphate, 2'-deoxycytosine 5'-triphosphate, β-glycerol phosphate, pyrophosphate, guanosine 5'-triphosphate, 2'-deoxyguanosine 5'-triphosphate, uridine 5'-triphosphate, dithiophosphate, 3'-deoxythymidine 5'-triphosphate, tripolyphosphate, D-myo-inositol 1,4,5-triphosphate and sulfate. Most preferably, the modulating anion is selected from adenosine 5'-triphosphate, β-glycerol phosphate, pyrophosphate, dithiophosphate and sulfate.

The extent to which the in vitro GGTase-I inhibitory potency of the prenyl-protein transferase inhibitor is increased in the presence of the modulating anion is dependent on the amount of anion that is added to the buffered assay system and the nature of the modulating anion. Preferably from about 0.1 mM to about 100 mM of the modulating anion is added to the buffered assay system. Most preferably, from about 1 mM to about 10 mM of the modulating anion is added.

The protein or peptide substrate utilized in the instant assay may incorporate any $CAAX^G$ motif that is geranylgeranylated by GGTase-I. The term "$CAAX^G$" will refer to such motifs that may be geranylgeranylated by GGTase-I. In particular such "$CAAX^G$" motifs include (the corresponding human protein is in parentheses): CVIM (K4B-Ras), CVLL (mutated H-Ras), CVVM (N-Ras), CIIM (K4A-Ras), CLLL (Rap-IA), CQLL (Rap-IB), CSIM, CAIM, CKVL, CLIM (PFX) and CVIL (Rap-2B). Preferably, the CAAX motif is CVIM. It is understood that some of the "$CAAX^G$" containing protein or peptide substrates may also be farnesylated by farnesyl-protein transferase.

As used herein, the term "$CAAX^F$" is used to designate a protein or peptide substrate that incorporates four amino acid C-terminus motif that is farnesylated by farnesyl-protein transferase. In particular such "$CAAX^F$" motifs include (the corresponding human protein is in parentheses): CVLS (H-ras), CVIM (K4B-Ras), CVVM (N-Ras) and CNIQ (Rap-2A). It is understood that certain of the "$CAAX^F$" containing protein or peptide substrates may also be geranylgeranylated by GGTase-I.

When a particular Ras protein is referred to herein by a term such as "K4B-Ras", "N-Ras", "H-Ras" and the like, such a term represents both the protein arising from expression of the corresponding wild type ras gene and various proteins arising from expression of ras genes containing various point mutations. When a particular ras gene is referred to herein by a term such as "K4B-ras", "N-ras", "H-ras" and the like, such a term represents both the wild type ras gene and ras genes containing various point mutations.

It is further preferred that the compound identified by the instant method is also a potent in vivo farnesyl-protein transferase inhibitor. It has been surprisingly found that such a potent dual inhibitor is particularly useful as an in vivo inhibitor of the growth of cancer cells, particularly those cancers characterized by a mutated K4B-Ras protein, at concentrations of inhibitor that do not cause mechanism based toxicity. Mechanism-based toxicity of farnesyl-protein transferase inhibitors can be anticipated in rapidly proliferating tissues, for example, the bone marrow. Such an inhibitor can be identified by the steps of:

a) assessing a test compound for its in vitro inhibitory activity against transfer of a geranylgeranyl residue to a protein or peptide substrate comprising a $CAAX^G$ motif by geranylgeranyl-protein transferase in the presence of a modulating anion;

b) assessing a test compound for its in vitro inhibitory activity against transfer of a farnesyl residue to a protein or peptide substrate comprising a $CAAX^F$ motif by farnesyl-protein transferase; and c) assessing the test compound for its ability to inhibit the anchorage independent growth of H-ras-transformed mammalian fibroblasts.

Preferably, the potent dual inhibitor identified by the instant method has an $IC_{50}$ of less than about 100 nM against the anchorage independent growth of H-ras-transformed mammalian fibroblasts in a cell culture assay (referred to herein as the SALSA assay). Other methods of assessing the ability of a test compound to inhibit the anchorage independent growth of ras-transformed mammalian fibroblasts have been previously described (eg. N. E. Kohl et al. *Science*, 260:1934–1937 (1993)). Most preferably, the potent dual inhibitor identified by the instant method has an $IC_{50}$ of less than about 20 nM in the SALSA assay.

Preferably the potent dual inhibitor has an inhibitory concentration ($IC_{50}$) of less than about 1 $\mu M$ against GGTase-I in the modified in vitro GGTase-I assay. More preferably such compounds have inhibitory concentrations ($IC_{50}$) of less than about 500 nM against GGTase-I in the presence of a modulating anion. Preferably the potent dual inhibitor has an inhibitory concentration ($IC_{50}$) of less than about 500 nM against FPTase in the in vitro FPTase assay. More preferably, the instant inhibitor has an inhibitory concentration ($IC_{50}$) of less than about 100 nM against FPTase in the in vitro FPTase assay. Still more preferably, the instant inhibitor has an inhibitory concentration ($IC_{50}$) of less than about 10 nM against FPTase in the in vitro FPTase assay.

Preferably, the potent dual inhibitor identified by the instant method has an $IC_{50}$ of less than about 1 $\mu M$ against the anchorage independent growth of H-ras-transformed mammalian fibroblasts in a cell culture assay (referred to herein as the SALSA assay), an inhibitory concentration ($IC_{50}$) of less than about 1 $\mu M$ against GGTase-I in the modified in vitro GGTase-I assay and an inhibitory concentration ($IC_{50}$) of less than about 500 nM against FPTase in the in vitro FPTase assay.

In a further embodiment of the instant invention, with regard to the compound utilized in the instant methods of inhibiting both farnesyl-protein transferase and GGTase-I and treating cancer, the ratio of the apparent enzymologic $K_i$ value of the compound against transfer of a geranylgeranyl residue to a protein or peptide substrate comprising a $CAAX^G$ motif by geranylgeranyl-protein transferase type I in the presence of a modulating anion (hereafter $K_{ia}^G$) (determined as described in Example 11) to the apparent enzymologic $K_i$ value of the compound against transfer of a farnesyl residue to a protein or peptide substrate comprising a $CAAX^F$ motif by farnesyl-protein transferase (hereafter $K_{ia}^F$) (determined as described in Example 10) is greater than 0.002 and less than 5,000. As used herein, the term "apparent enzymologic $K_i$" represents either the only enzymologic $K_i$ exhibited by a compound in the assay and calculations or, if multiple enzymologic $K_i$'s are exhibited by a compound in the assay and calculations, then the lowest enzymologic $K_i$. Preferably, the ratio of $K_{ia}^G$ to $K_{ia}^F$ is greater than 0.1 and less than 500. Most preferably, ratio of $K_{ia}^G$ to $K_{ia}^F$ is greater than 1 and less than 100.

The term GGTase-I or farnesyl-protein transferase inhibiting compound refers to compounds which antagonize, inhibit or counteract the activities of: the gene coding GGTase-I or farnesyl-protein transferase or the proteins encoded by these genes.

The preferred therapeutic effect provided by the instant composition is the treatment of cancer and specifically the inhibition of cancerous tumor growth and/or the regression of cancerous tumors. Cancers which are treatable in accordance with the invention described herein include cancers of the brain, breast, colon, genitourinary tract, prostate, skin, lymphatic system, pancreas, rectum, stomach, larynx, liver and lung. More particularly, such cancers include histiocytic lymphoma, lung adenocarcinoma, pancreatic carcinoma, colo-rectal carcinoma, small cell lung cancers, bladder cancers, head and neck cancers, acute and chronic leukemias, melanomas, and neurological tumors.

The composition of this invention is also useful for inhibiting other proliferative diseases, both benign and malignant, wherein Ras proteins are aberrantly activated as a result of oncogenic mutation in other genes (i.e., the ras gene itself is not activated by mutation to an oncogenic form) with said inhibition being accomplished by the administration of an effective amount of the instant composition to a mammal in need of such treatment. For example, the composition is useful in the treatment of neurofibromatosis, which is a benign proliferative disorder.

The composition of the instant invention is also useful in the prevention of restenosis after percutaneous transluminal coronary angioplasty by inhibiting neointimal formation (C. Indolfi et al. *Nature medicine*, 1:541–545(1995).

The instant composition may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of vision deficit related to retinal vascularization.

The instant compounds may also be useful in the treatment of certain viral infections, in particular in the treatment of hepatitis delta and related viruses (J. S. Glenn et al. *Science*, 256:1331–1333 (1992).

The instant compounds may also be useful as inhibitors of proliferation of vascular smooth muscle cells and therefore useful in the prevention and therapy of arteriosclerosis and diabetic vascular pathologies.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

As used herein, the term "composition" is intended to encompass a product comprising the specified ingredients in the specific amounts, as well as any product which results, directly or indirectly, from combination of the specific ingredients in the specified amounts.

The compounds identified by the instant method may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of neurofibromatosis, restinosis, polycystic kidney disease, infections of hepatitis delta and related viruses and fungal infections. The instant compounds may also be useful in combination with other inhibitors of parts of the signaling pathway that links cell surface growth factor receptors to nuclear signals initiating cellular proliferation.

The instant compounds may be utilized in combination with farnesyl pyrophosphate competitive inhibitors of the activity of farnesyl-protein transferase or in combination with a compound which has Raf antagonist activity. The instant compounds may also be co-administered with compounds that are selective inhibitors of geranylgeranyl protein transferase or selective inhibitors of farnesyl-protein transferase.

The compounds of the instant invention may also be co-administered with other well known cancer therapeutic agents that are selected for their particular usefulness against the condition that is being treated. Included in such combinations of therapeutic agents are combinations of the instant prenyl-protein transferase inhibitors and an antineoplastic agent. It is also understood that the instant combination of antineoplastic agent and inhibitor of prenyl-protein transferase may be used in conjunction with other methods of treating cancer and/or tumors, including radiation therapy and surgery.

If formulated as a fixed dose, such combination products employ the combinations of this invention within the dosage range described below and the other pharmaceutically active agent(s) within its approved dosage range Combinations of the instant invention may alternatively be used sequentially with known pharmaceutically acceptable agent(s) when a multiple combination formulation is inappropriate.

Radiation therapy, including x-rays or gamma rays which are delivered from either an externally applied beam or by implantation of tiny radioactive sources, may also be used in combination with an inhibitor of prenyl-protein transferase alone to treat cancer.

Additionally, compounds of the instant invention may also be useful as radiation sensitizers, as described in WO 97/38697, published on Oct. 23, 1997, and herein incorporated by reference.

The instant compounds may also be useful in combination with other inhibitors of parts of the signaling pathway that links cell surface growth factor receptors to nuclear signals initiating cellular proliferation. Thus, the instant compounds may be utilized in combination with farnesyl pyrophosphate competitive inhibitors of the activity of farnesyl-protein transferase or in combination with a compound which has Raf antagonist activity.

The instant compounds may also be useful in combination with an integrin antagonist for the treatment of cancer, as described in U.S. Ser. No. 09/055,487, filed Apr. 6, 1998, which is incorporated herein by reference.

As used herein the term an integrin antagonist refers to compounds which selectively antagonize, inhibit or counteract binding of a physiological ligand to an integrin(s) that is involved in the regulation of angiogenisis, or in the growth and invasiveness of tumor cells. In particular, the term refers to compounds which selectively antagonize, inhibit or counteract binding of a physiological ligand to the ($\alpha v \beta 3$ integrin, which selectively antagonize, inhibit or counteract binding of a physiological ligand to the ($\alpha v \beta 5$ integrin, which antagonize, inhibit or counteract binding of a physiological ligand to both the $\alpha v \beta 3$ integrin and the $\alpha v \beta 5$ integrin, or which antagonize, inhibit or counteract the activity of the particular integrin(s) expressed on capillary endothelial cells. The term also refers to antagonists of the $\alpha v \beta 6$, $\alpha v \beta 8$, $\alpha 1 \beta 1$, $\alpha 2 \beta 1$, $\alpha 5 \beta 1$, $\alpha 6 \beta 1$ and $\alpha 6 \beta 4$ integrins. The term also refers to antagonists of any combination of $\alpha v \beta 3$, $\alpha v \beta 5$, $\alpha v \beta 6$, $\alpha v \beta 8$, $\alpha 1 \beta 1$, $\alpha 2 \beta 1$, $\alpha 5 \beta 1$, $\alpha 6 \beta 1$ and $\alpha 6 \beta 4$ integrins. The instant compounds may also be useful with other agents that inhibit angiogenisis and thereby inhibit the growth and invasiveness of tumor cells, including, but not limited to angiostatin and endostatin.

When a composition according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of a prenyl-protein transferase inhibitor are administered to a mammal undergoing treatment for cancer. Administration occurs in an amount of each type of inhibitor of between about 0.1 mg/kg of body weight to about 60 mg/kg of body weight per day, preferably of between 0.5 mg/kg of body weight to about 40 mg/kg of body weight per day. A particular therapeutic dosage that comprises the instant composition includes from about 0.01 mg to about 1000 mg of a prenyl-protein transferase inhibitor. Preferably, the dosage comprises from about 1 mg to about 1000 mg of a prenyl-protein transferase inhibitor.

Examples of an antineoplastic agent include, in general, microtubule-stabilising agents (such as paclitaxel (also known as Taxol®), docetaxel (also known as Taxotere®), or their derivatives); alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

Compounds of the instant invention that are identified by the properties described hereinabove include:

(a) a compound represented by formula I:

$$\text{(R}^8\text{)}_r\text{—V—A}^1(\text{CR}^{1a}_2)_n\text{A}^2(\text{CR}^{1a}_2)_n\text{—[ring]—}(\text{CR}^{1b}_2)_p\text{—X—N[ring]N—Z} \quad \text{I}$$

wherein:
$R^{1a}$ is selected from: hydrogen or $C_1$–$C_6$ alkyl;
$R^{1b}$ is independently selected from:
  a) hydrogen,
  b) aryl, heterocycle, cycloalkyl, $R^{10}O$—, —$N(R^{10})_2$ or $C_2$–$C_6$ alkenyl,
  c) $C_1$–$C_6$ alkyl unsubstituted or substituted by aryl, heterocycle, cycloalkyl, alkenyl, $R^{10}O$—, or —$N(R^{10})_2$;
$R^3$ and $R^4$ selected from H and $CH_3$;
$R^2$ is selected from H; unsubstituted or substituted aryl, unsubstituted or substituted heteroaryl, $$\text{—C(=O)NR}^6\text{R}^7;$$

or $C_{1-5}$ alkyl, unbranched or branched, unsubstituted or substituted with one or more of:
  1) aryl,
  2) heterocycle,
  3) $OR^6$,
  4) $SR^{6a}$, $SO_2R^{6a}$, or
  5)

$$\text{—C(=O)NR}^6\text{R}^7;$$

and $R^2$ and $R^3$ are optionally attached to the same carbon atom;

$R^6$ and $R^7$ are independently selected from:
  H; $C_{1-4}$ alkyl, $C_{3-6}$ cycloalkyl, aryl, heterocycle, unsubstituted or substituted with:
    a) $C_{1-4}$ alkoxy,
    b) halogen,
    c) perfluoro-$C_{1-4}$ alkyl, or
    d) aryl or heterocycle;

$R^{6a}$ is selected from:
  $C_{1-4}$ alkyl or $C_{3-6}$ cycloalkyl, unsubstituted or substituted with:
    a) $C_{1-4}$ alkoxy,
    b) halogen, or
    c) aryl or heterocycle;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ is hydrogen or methyl;
$R^{10}$ is independently selected from hydrogen, $C_1$–$C_6$ alkyl, $C_1$–$C_6$ perfluoroalkyl, 2,2,2-trifluoroethyl, benzyl and aryl;
$R^{11}$ is independently selected from $C_1$–$C_6$ alkyl and aryl;
$A^1$ and $A^2$ are independently selected from: a bond, —CH=CH—, —C≡C—, —C(O)—, —C(O)NR$^{10}$—, O, —N(R$^{10}$)—, or S(O)$_m$;
V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) $C_1$–$C_{20}$ alkyl wherein from 0 to 4 carbon atoms are replaced with a heteroatom selected from O, S, and N, and
  e) $C_2$–$C_{20}$ alkenyl, and provided that V is not hydrogen if $A^1$ is S(O)$_m$ and V is not hydrogen if $A^1$ is a bond, n is 0 and $A^2$ is S(O)$_m$;

X is —$CH_2$— or —C(=O)—;
Z is selected from:
  1) a unsubstituted or substituted group selected from aryl, heteroaryl, arylmethyl, heteroarylmethyl, arylsulfonyl, heteroarylsulfonyl, wherein the substituted group is substituted with one or more of the following:
    a) $C_{1-4}$ alkyl, unsubstituted or substituted with: $C_{1-4}$ alkoxy, $NR^6R^7$, $C_{3-6}$ cycloalkyl, unsubstituted or substituted aryl, heterocycle, HO, —S(O)$_m$R$^{6a}$, or —C(O)NR$^6$R$^7$,
    b) aryl or heterocycle,
    c) halogen,
    d) OR$^6$, e) $NR^6R^7$,
f) CN,
g) $NO_2$,
h) $CF_3$;
i) $-S(O)_mR^{6a}$,
j) $-C(O)NR^6R^7$, or
k) $C_3-C_6$ cycloalkyl; or
2) unsubstituted $C_1-C_6$ alkyl, substituted $C_1-C_6$ alkyl, unsubstituted $C_3-C_6$ cycloalkyl or substituted $C_3-C_6$ cycloalkyl, wherein the substituted $C_1-C_6$ alkyl and substituted $C_3-C_6$ cycloalkyl is substituted with one or two of the following:
a) $C_{1-4}$ alkoxy,
b) $NR^6R^7$,
c) $C_{3-6}$ cycloalkyl,
d) $-NR^6C(O)R^7$,
e) HO,
f) $-S(O)_mR^{6a}$,
g) halogen, or
h) perfluoroalkyl;

m is 0, 1 or 2;
n is 0, 1, 2, 3 or 4;
p is 0, 1, 2, 3 or 4; and
r is 0 to 5, provided that r is 0 when V is hydrogen;
provided that the substituent $(R^8)_r-V-A^1(CR^{1a}_2)_nA^2(CR^{1a}_2)_n-$ is not H;
b) the inhibitors of farnesyl-protein transferase are illustrated by the formula II:

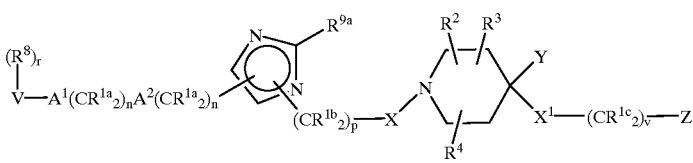

II wherein:

$R^{1a}$ is selected from: hydrogen or $C_1-C_6$ alkyl;

$R^{1b}$ is independently selected from:
a) hydrogen,
b) aryl, heterocycle, cycloalkyl, $R^{10}O-$, $-N(R^{10})_2$ or $C_2-C_6$ alkenyl,
c) $C_1-C_6$ alkyl unsubstituted or substituted by unsubstituted or substituted aryl, heterocycle, cycloalkyl, alkenyl, $R^{10}O-$, or $-N(R^{10})_2$;

$R^{1c}$ is selected from:
a) hydrogen,
b) unsubstituted or substituted $C_1-C_6$ alkyl wherein the substituent on the substituted $C_1-C_6$ alkyl is selected from unsubstituted or substituted aryl, heterocyclic, $C_3-C_{10}$ cycloalkyl, $C_2-C_6$ alkenyl, $C_2-C_6$ alkynyl, $R^{10}O-$, $R^{11}S(O)_m-$, $R^{10}C(O)NR^{10}-$, $(R^{10})_2N-C(O)-$, CN, $(R^{10})_2N-C(NR^{10})-$, $R^{10}C(O)-$, $R^{10}OC(O)-$, $N_3$, $-N(R^{10})_2$, and $R^{11}OC(O)-NR^{10}-$, and
c) unsubstituted or substituted aryl;

$R^3$ and $R^4$ independently selected from H and $CH_3$;

$R^2$ is selected from H; $OR^{10}$;

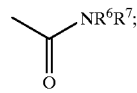

or $C_{1-5}$ alkyl, unbranched or branched, unsubstituted or substituted with one or more of:
1) aryl,
2) heterocycle,
3) $OR^6$,
4) $SR^{6a}$, $SO_2R^{6a}$, or
5)

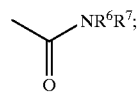

and $R^2$, $R^3$ and $R^4$ are optionally attached to the same carbon atom;

$R^6$ and $R^7$ are independently selected from: H; $C_{1-4}$ alkyl, $C_{3-6}$ cycloalkyl, aryl, heterocycle, unsubstituted or substituted with:
a) $C_{1-4}$ alkoxy,
b) halogen, or
c) aryl or heterocycle;

$R^{6a}$ is selected from:
$C_{1-4}$ alkyl or $C_{3-6}$ cycloalkyl, unsubstituted or substituted with:
a) $C_{1-4}$ alkoxy,
b) halogen, or
c) aryl or heterocycle;

$R^8$ is independently selected from:
a) hydrogen,
b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{9a}$ is hydrogen or methyl;

$R^{10}$ is independently selected from hydrogen, $C_1-C_6$ alkyl, $C_1-C_6$ perfluoroalkyl, 2,2,2-trifluoroethyl, benzyl and aryl;

$R^{11}$ is independently selected from $C_1-C_6$ alkyl and aryl;

$R^{12}$ is selected from: H; unsubstituted or substituted $C_{1-8}$ alkyl, unsubstituted or substituted aryl or unsubstituted or substituted heterocycle, wherein the substituted alkyl, substituted aryl or substituted heterocycle is substituted with one or more of:
1) aryl or heterocycle, unsubstituted or substituted with:

a) $C_{1-4}$ alkyl,
b) $(CH_2)_pOR^6$,
c) $(CH_2)_pNR^6R^7$,
d) halogen,
e) CN,
f) aryl or heteroaryl,
g) perfluoro-$C_{1-4}$ alkyl,
h) $SR^{6a}$, $S(O)R^{6a}$, $SO_2R^{6a}$,
2) $C_{3-6}$ cycloalkyl,
3) $OR^6$,
4) $SR^{6a}$, $S(O)R^{6a}$, or $SO_2R^{6a}$, 5) 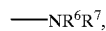—$NR^6R^7$, 6) 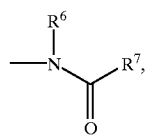

7) 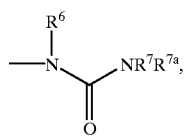

8) 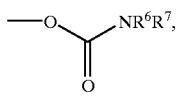

9) 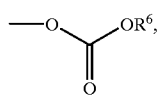

10) 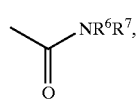

11) 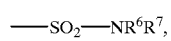—$SO_2$—$NR^6R^7$,

12) 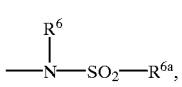

13) 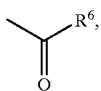

14) 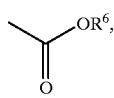

15) $N_3$,
16) F,
17) perfluoro-$C_{1-4}$-alkyl, or
18) $C_{1-6}$-alkyl;

$A^1$ and $A^2$ are independently selected from: a bond, —CH=CH—, —C≡C—, —C(O)—, —C(O)NR^{10}—, —NR^{10}C(O)—, O, —N(R^{10})—, or $S(O)_m$;

V is selected from:

a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1-C_{20}$ alkyl wherein from 0 to 4 carbon atoms are replaced with a heteroatom selected from O, S, and N, and
e) $C_2-C_{20}$ alkenyl, and provided that V is not hydrogen if $A^1$ is $S(O)_m$ and V is not hydrogen if $A^1$ is a bond, n is 0 and $A^2$ is $S(O)_m$;

X is —$CH_2$— or —C(=O)—;

$X^1$ is a bond, —C(=O)—, —$NR^6C(=O)$—, —$NR^6$—, —O— or —$S(=O)_m$—;

Y is selected from:
a) hydrogen,
b) $R^{10}O$—, $R^{11}S(O)_m$—, $R^{10}C(O)NR^{10}$—, $(R^{10})_2N$—C(O)—, CN, $NO_2$, $(R^{10})_2N$—$C(NR^{10})$—, $R^{12}C(O)$—, $R^{10}OC(O)$—, $N_3$, F, —$N(R^{10})_2$, or $R^{11}OC(O)NR^{10}$—,
c) unsubstituted or substituted $C_1-C_6$ alkyl wherein the substituent on the substituted $C_1-C_6$ alkyl is selected from unsubstituted or substituted aryl, $R^{10}O$—, $R^{10}C(O)NR^{10}$—, $(R^{10})_2N$—C(O)—, $R^{10}C(O)$— and $R^{10}OC(O)$—;

Z is an unsubstituted or substituted aryl, wherein the substituted aryl is substituted with one or more of the following:
1) $C_{1-4}$ alkyl, unsubstituted or substituted with:
 a) $C_{1-4}$ alkoxy,
 b) $NR^6R^7$,
 c) $C_{3-6}$ cycloalkyl,
 d) aryl, substituted aryl or heterocycle,
 e) HO,
 f) —$S(O)_mR^{6a}$, or
 g) —$C(O)NR^6R^7$,
2) aryl or heterocycle,
3) halogen,
4) $OR^6$,
5) $NR^6R^7$,
6) CN,
7) $NO_2$,
8) $CF_3$;
9) —$S(O)_mR^{6a}$,
10) —$C(O)NR^6R^7$, or
11) $C_3-C_6$ cycloalkyl;

m is 0, 1 or 2;
n is 0, 1, 2, 3 or 4;
p is 0, 1, 2, 3 or 4; and
r is 0 to 5, provided that r is 0 when V is hydrogen; and
v is 0, 1 or 2;

(c) a compound represented by formula III:

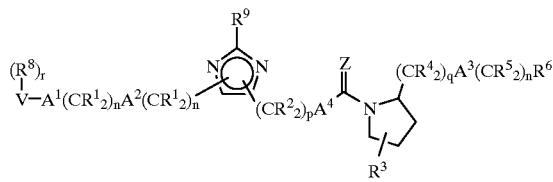

III wherein:

$R^1$ is independently selected from: hydrogen or $C_1$–$C_6$ alkyl;

$R^2$ is independently selected from:
  a) hydrogen,
  b) substituted or unsubstituted aryl, substituted or unsubstituted heterocycle, $C_3$–$C_{10}$ cycloalkyl, $R^{10}O$— or $C_2$–$C_6$ alkenyl,
  c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

$R^3$ is selected from:
  a) hydrogen,
  b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, —$N(R^{10})_2$, or $R^{11}OC(O)NR^{10}$—,
  c) substituted or unsubstituted aryl, substituted or unsubstituted heterocycle, $C_3$–$C_{10}$ cycloalkyl, $C_2$–$C_6$ alkenyl, fluoro, chloro, $R^{12}O$—, $R^{11}S(O)_m$—, $R^{10}C(O)NR^{10}$—, CN, $NO_2$, $(R^{10})_2N$—$C(NR^{10})$—, $R^{10}C(O)$—, $N_3$, —$N(R^{10})_2$, or $R^{11}OC(O)NR^{10}$—, and
  d) $C_1$–$C_6$ alkyl substituted with an unsubstituted or substituted group selected from substituted or unsubstituted aryl, substituted or unsubstituted heterocyclic and $C_3$–$C_{10}$ cycloalkyl;

$R^4$ and $R^5$ are independently selected from:
  a) hydrogen,
  b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, —$N(R^{10})_2$, or $R^{11}OC(O)NR^{10}$—,
  c) substituted or unsubstituted aryl, substituted or unsubstituted heterocycle, $C_3$–$C_{10}$ cycloalkyl, $C_2$–$C_6$ alkenyl, fluoro, chloro, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $N_3$, —$N(R^{10})_2$, or $R^{11}OC(O)NR^{10}$—, and
  d) $C_1$–$C_6$ alkyl substituted with an unsubstituted or substituted group selected from substituted or unsubstituted aryl, substituted or unsubstituted heterocyclic and $C_3$–$C_{10}$ cycloalkyl;

$R^6$ is independently selected from:
  a) hydrogen,
  b) substituted or unsubstituted aryl, substituted or unsubstituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, allyloxy, $R^{10}C(O)NR^{10}$—, CN, $NO_2$, $(R^{10})_2N$—$C(NR^{10})$—, $R^{10}C(O)$—, —$N(R^{10})_2$, $(R^{12})_2NC(O)$— or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^7$ is independently selected from
  a) hydrogen,
  b) unsubstituted or substituted aryl,
  c) unsubstituted or substituted heterocycle,
  d) unsubstituted or substituted cycloalkyl, and
  e) $C_1$–$C_6$ alkyl substituted with hydrogen or an unsubstituted or substituted group selected from aryl, heterocycle and cycloalkyl;
    wherein heterocycle is selected from pyrrolidinyl, imidazolyl, pyridinyl, thiazolyl, pyridonyl, indolyl, quinolinyl, isoquinolinyl, and thienyl;

$R^8$ is selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^9$ is selected from:
  a) hydrogen,
  b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
  c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_6$ alkyl, $C_1$–$C_6$ perfluoroalkyl, 2,2,2-trifluoroethyl, benzyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ alkyl substituted with $CO_2R^{10}$, $C_1$–$C_6$ alkyl substituted with aryl, $C_1$–$C_6$ alkyl substituted with substituted aryl, $C_1$–$C_6$ alkyl substituted with heterocycle, $C_1$–$C_6$ alkyl substituted with substituted heterocycle, aryl and substituted aryl;

$A^1$ and $A^2$ are independently selected from: a bond, —CH=CH—, —C≡C—, —C(O)—, —C(O)NR$^7$—, —NR$^7$C(O)—, —S(O)$_2$NR$^7$—, —NR$^7$S(O)$_2$—, O, —N(R$^7$)—, or S(O)$_m$;

$A^3$ is selected from: a bond, —C(O)NR$^7$—, —NR$^7$C(O)—, —S(O)$_2$NR$^7$—, —NR$^7$S(O)$_2$— or—N(R$^7$)—;

$A^4$ is selected from: a bond, O, —N(R$^7$)— or S;

V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) $C_1$–$C_{20}$ alkyl wherein from 0 to 4 carbon atoms are replaced with a heteroatom selected from O, S, and N, and
  e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

Z is independently $(R^1)_2$ or O;

m is 0, 1 or 2;

n is 0, 1, 2, 3 or 4;

p is 0, 1, 2, 3 or 4;

q is 0 or 1; and r is 0 to 5, provided that r is 0 when V is hydrogen;

d) a compound represented by formula A:

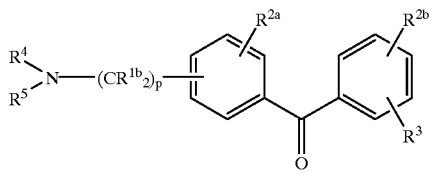

wherein:

$R^{1a}$ is selected from: hydrogen or $C_1$–$C_6$ alkyl;

$R^{1b}$ is independently selected from:
  a) hydrogen,
  b) aryl, heterocycle, cycloalkyl, $R^{10}O$—, —$N(R^{10})_2$ or $C_2$–$C_6$ alkenyl,
  c) $C_1$–$C_6$ alkyl unsubstituted or substituted by aryl, heterocycle, cycloalkyl, alkenyl, $R^{10}O$—, or —$N(R^{10})_2$;

$R^{2a}$, $R^{2b}$ and $R^3$ are independently selected from:
  a) hydrogen,
  b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $R^{10}OC(O)$—, —$N(R^{10})_2$, or $R^{11}OC(O)NR^{10}$—,
  c) unsubstituted or substituted aryl, unsubstituted or substituted heterocycle, unsubstituted or substituted cycloalkyl, alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, halogen or $R^{11}OC(O)NR^{10}$—, and
  d) $C_1$–$C_6$ alkyl substituted with an unsubstituted or substituted group selected from aryl, heterocyclic and $C_3$–$C_{10}$ cycloalkyl;

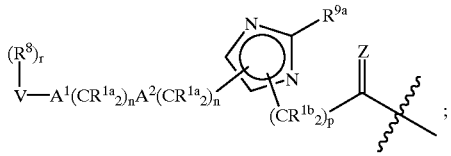

$R^5$ is hydrogen;

$R^8$ is selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{9a}$ is independently selected from $C_1$–$C_6$ alkyl and aryl;

$R^{10}$ is independently selected from hydrogen, $C_1$–$C_6$ alkyl, $C_1$–$C_6$ perfluoroalkyl, 2,2,2-trifluoroethyl, benzyl and aryl;

$R^{11}$ is independently selected from $C_1$–$C_6$ alkyl, benzyl and aryl;

$A^1$ and $A^2$ are independently selected from: a bond, —CH=CH—, —C≡C—, —C(O)—, —C(O)NR^8—, —NR^8C(O)—, O, —N(R^8)—, —S(O)_2N(R^8)—, —N(R^8)S(O)_2—, or $S(O)_m$;

V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) $C_1$–$C_{20}$ alkyl wherein from 0 to 4 carbon atoms are replaced with a heteroatom selected from O, S, and N, and
  e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

Z is $H_2$ or O;

m is 0, 1 or 2;

n is 0, 1, 2, 3 or 4;

p is independently 0, 1, 2, 3 or 4; and r is 0 to 5, provided that r is 0 when V is hydrogen;

or the pharmaceutically acceptable salts thereof.

In a further embodiment of the formula I compounds of this invention, the inhibitors of farnesyl-protein transferase are illustrated by the formula I-a:

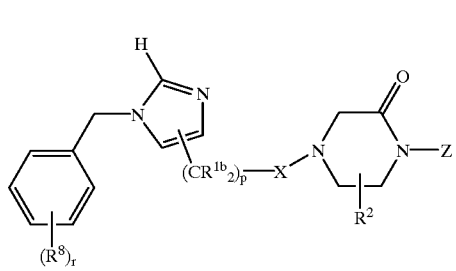

wherein:

$R^{1b}$ is independently selected from:
  a) hydrogen,
  b) aryl, heterocycle, cycloalkyl, $R^{10}O$—, —$N(R^{10})_2$ or $C_2$–$C_6$ alkenyl,
  c) $C_1$–$C_6$ alkyl unsubstituted or substituted by aryl, heterocycle, cycloalkyl, alkenyl, $R^{10}O$—, or —$N(R^{10})_2$;

$R^2$ is selected from H; unsubstituted or substituted aryl or $C_{1-5}$ alkyl, unbranched or branched, unsubstituted or substituted with one or more of:
  1) aryl,
  2) heteroaryl,
  3) $OR^6$, or
  4) $SR^{6a}$;

$R^6$ and $R^7$ are independently selected from: $C_{1-4}$ alkyl, aryl, and heteroaryl, unsubstituted or substituted with:
  a) $C_{1-4}$ alkoxy,
  b) halogen,
  c) perfluoro-$C_{1-4}$ alkyl, or
  d) aryl or heteroaryl;

$R^{6a}$ is selected from:
  $C_{1-4}$ alkyl, unsubstituted or substituted with:
  a) $C_{1-4}$ alkoxy, or
  b) aryl or heteroaryl;

$R^8$ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{10}$ is independently selected from hydrogen, $C_1$–$C_6$ alkyl, $C_1$–$C_6$ perfluoroalkyl, 2,2,2-trifluoroethyl, benzyl and aryl;

$R^{11}$ is independently selected from $C_1$–$C_6$ alkyl and aryl;

X is —$CH_2$— or —C(=O)—;

Z is an unsubstituted or substituted group selected from aryl, arylmethyl and arylsulfonyl, wherein the substituted group is substituted with one or more of the following:
  a) $C_{1-4}$ alkyl, unsubstituted or substituted with: $C_{1-4}$ alkoxy $NR^6R^7$, $C_{3-6}$ cycloalkyl, unsubstituted or substituted aryl, heterocycle, HO, —$S(O)_mR^{6a}$, or —$C(O)NR^6R^7$,
  b) aryl or heterocycle,
  c) halogen,
  d) $OR^6$,
  e) $NR^6R^7$,
  f) CN,
  g) $NO_2$,
  h) $CF_3$;
  i) —$S(O)_mR^{6a}$,
  j) —$C(O)NR^6R^7$, or
  k) $C_3$–$C_6$ cycloalkyl;

m is 0, 1 or 2; and p is 0, 1, 2, 3 or 4; and r is 0 to 3;

or the pharmaceutically acceptable salts thereof.

In another embodiment of this invention, the inhibitors of farnesyl-protein transferase are illustrated by the formula II-a:

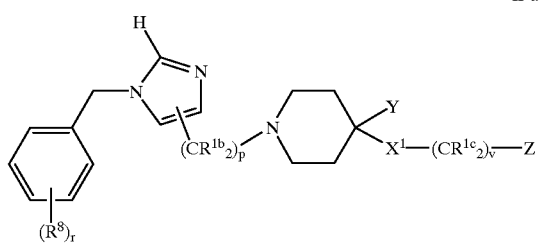

II-a wherein:

$R^{1b}$ is independently selected from:
  a) hydrogen,
  b) aryl, heterocycle, cycloalkyl, $R^{10}O$—, —$N(R^{10})_2$ or $C_2$–$C_6$ alkenyl,
  c) $C_1$–$C_6$ alkyl unsubstituted or substituted by unsubstituted or substituted aryl, heterocycle, cycloalkyl, alkenyl, $R^{10}O$—, or —$N(R^{10})_2$;

$R^{1c}$ is selected from:
  a) hydrogen,
  b) unsubstituted or substituted $C_1$–$C_6$ alkyl wherein the substituent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—$C(NR^{10})$—, $R^{10}C(O)$—, $R^{10}C(O)$—, $N_3$, —$N(R^{10})_2$, and $R^{11}OC(O)$—$NR^{10}$—, and
  c) unsubstituted or substituted aryl;

$R^6$, $R^7$ and $R^7a$ are independently selected from: H; $C_{1-4}$ alkyl, $C_{3-6}$ cycloalkyl, aryl, heterocycle, unsubstituted or substituted with:
  a) $C_{1-4}$ alkoxy,
  b) halogen, or
  c) aryl or heterocycle;

$R^{6a}$ is selected from:
$C_{1-4}$ alkyl or $C_{3-6}$ cycloalkyl, unsubstituted or substituted with:
  a) $C_{1-4}$ alkoxy,
  b) halogen, or
  c) aryl or heterocycle;

$R^8$ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{10}$ is independently selected from hydrogen, $C_1$–$C_6$ alkyl, $C_1$–$C_6$ perfluoroalkyl, 2,2,2-trifluoroethyl, benzyl and aryl;

$R^{11}$ is independently selected from $C_1$–$C_6$ alkyl and substituted or unsubstituted aryl;

$R^{12}$ is selected from: H; unsubstituted or substituted $C_{1-8}$ alkyl, unsubstituted or substituted aryl or unsubstituted or substituted heterocycle, wherein the substituted alkyl, substituted aryl or substituted heterocycle is substituted with one or more of:
  1) aryl or heterocycle, unsubstituted or substituted with:
    a) $C_{1-4}$ alkyl,
    b) halogen,
    c) CN,
    d) perfluoro-$C_{1-4}$ alkyl,
  2) $C_{3-6}$ cycloalkyl,
  3) $OR^6$,
  4) $SR^{6a}$, $S(O)R^{6a}$, or $SO_2R^{6a}$,

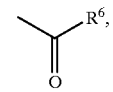

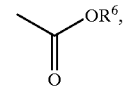

$X^1$ is a bond, —C(=O)— or —$S(=O)_m$;

Y is selected from:
  a) hydrogen,
  b) $R^{10}O$—, $R^{11}S(O)_m$—, $R^{10}C(O)NR^{10}$—, $(R^{10})_2N$—C(O)—, CN, $NO_2$, $(R^{10})_2N$—$C(NR^{10})$—, $R^{12}C(O)$—, $R^{10}OC(O)$—, $N_3$, F, —$N(R^{10})_2$, or $R^{11}OC(O)NR^{10}$—,
  c) unsubstituted or substituted $C_1$–$C_6$ alkyl wherein the substituent on the substituted $C_1$–$C_6$ alkyl is selected from unsubstituted or substituted aryl, $R^{10}O$—, $R^{10}C(O)NR^{10}$—, $(R^{10})_2N$—C(O)—, $R^{10}C(O)$— and $R^{10}OC(O)$—;

Z is an unsubstituted or substituted aryl, wherein the substituted aryl is substituted with one or more of the following:

1) $C_{1-4}$ alkyl, unsubstituted or substituted with:
   a) $C_{1-4}$ alkoxy,
   b) $NR^6R^7$,
   c) $C_{3-6}$ cycloalkyl,
   d) aryl, substituted aryl or heterocycle,
   e) HO,
   f) $-S(O)_mR^{6a}$, or
   g) $-C(O)NR^6R^7$,
2) aryl or heterocycle,
3) halogen,
4) $OR^6$,
5) $NR^6R^7$,
6) CN,
7) $NO_2$,
8) $CF_3$,
9) $-S(O)_mR^{6a}$,
10) $-C(O)NR^6R^7$, or
11) $C_3-C_6$ cycloalkyl;

m is 0, 1 or 2;
p is 1 or 2;
r is 0 to 3; and
V is 0, or 2;
or a pharmaceutically acceptable salt thereof.

In a further embodiment of this invention, the inhibitors of farnesyl-protein transferase are illustrated by the formula III-a:

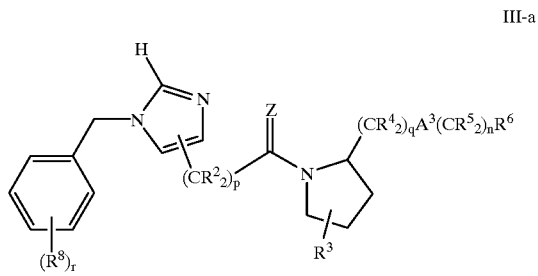

III-a wherein:
$R^2$ is independently selected from:
a) hydrogen,
b) aryl, heterocycle, cycloalkyl, $R^{10}O-$, $-N(R^{10})_2$ or $C_2-C_6$ alkenyl,
c) $C_1-C_6$ alkyl unsubstituted or substituted by aryl, heterocycle, cycloalkyl, alkenyl, $R^{10}O-$, or $-N(R^{10})_2$;

$R^3$ is selected from:
a) hydrogen,
b) $C_1-C_6$ alkyl unsubstituted or substituted by $C_2-C_6$ alkenyl, $R^{10}O-$, $R^{11}S(O)_m-$, $R^{10}C(O)NR^{10}-$, CN, $N_3$, $(R^{10})_2N-C(NR^{10})-$, $R^{10}C(O)-$, $-N(R^{10})_2$, or $R^{11}OC(O)NR^{10}-$,
c) substituted or unsubstituted aryl, substituted or unsubstituted heterocycle, $C_3-C_{10}$ cycloalkyl, $C_2-C_6$ alkenyl, fluoro, chloro, $R^{12}O-$, $R^{11}S(O)_m-$, $R^{10}C(O)NR^{10}-$, CN, $NO_2$, $(R^{10})_2N-C(NR^{10})-$, $R^{10}C(O)-$, $N_3$, $-N(R^{10})_2$, or $R^{11}OC(O)NR^{10}-$, and
d) $C_1-C_6$ alkyl substituted with an unsubstituted or substituted group selected from substituted or unsubstituted aryl, substituted or unsubstituted heterocyclic and $C_3-C_{10}$ cycloalkyl;

$R^4$ and $R^5$ are independently selected from:
a) hydrogen,
b) $C_1-C_6$ alkyl unsubstituted or substituted by $R^{10}O-$ or $-N(R^{10})_2$, c) substituted or unsubstituted aryl, substituted or unsubstituted heterocycle, $C_3-C_{10}$ cycloalkyl, $C_2-C_6$ alkenyl, fluoro, chloro, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $N_3$, $-N(R^{10})_2$, or $R^{11}OC(O)NR^{10}-$, and
d) $C_1-C_6$ alkyl substituted with an unsubstituted or substituted group selected from substituted or unsubstituted aryl, substituted or unsubstituted heterocyclic and $C_3-C_{10}$ cycloalkyl;

$R^6$ is independently selected from:
a) hydrogen,
b) substituted or unsubstituted aryl, substituted or unsubstituted heterocycle, $C_1-C_6$ alkyl, $C_2-C_6$ alkenyl, $C_2-C_6$ alkynyl, $C_1-C_6$ perfluoroalkyl, F, Cl, $R^{10}O-$, allyloxy, $R^{10}C(O)NR^{10}-$, CN, $NO_2$, $(R^{10})_2N-C(NR^{10})-$, $R^{10}C(O)-$, $-N(R^{10})_2$, $(R^{12})_2NC(O)-$ or $R^{11}OC(O)NR^{10}-$, and
c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^7$ is independently selected from
a) hydrogen,
b) unsubstituted or substituted aryl,
c) unsubstituted or substituted heterocycle,
d) unsubstituted or substituted cycloalkyl, and
e) $C_1-C_6$ alkyl substituted with hydrogen or an unsubstituted or substituted group selected from aryl, heterocycle and cycloalkyl;
  wherein heterocycle is selected from pyrrolidinyl, imidazolyl, pyridinyl, thiazolyl, pyridonyl, indolyl, quinolinyl, isoquinolinyl, and thienyl;

$R^8$ is independently selected from:
a) hydrogen,
b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{10}$ is independently selected from hydrogen, $C_1-C_6$ alkyl, $C_1-C_6$ perfluoroalkyl, 2,2,2-trifluoroethyl, benzyl and aryl;
$R^{11}$ is independently selected from $C_1-C_6$ alkyl and aryl;
$R^{12}$ is independently selected from hydrogen, $C_1-C_6$ alkyl, $C_1-C_6$ alkyl substituted with $CO_2R^{10}$, $C_1-C_6$ alkyl substituted with aryl, $C_1-C_6$ alkyl substituted with substituted aryl, $C_1-C_6$ alkyl substituted with heterocycle, $C_1-C_6$ alkyl substituted with substituted heterocycle, aryl and substituted aryl;
$A^3$ is selected from: a bond, $-C(O)NR^7-$, $-NR^7C(O)-$, $-S(O)_2NR^7-$, $-NR^7S(O)_2-$ or $-N(R^7)-$;
Z is independently $H_2$ or O;
m is 0, or 2; and
n is 0, 1, 2, 3 or 4;
p is 0, 1, 2, 3 or 4;
q is 0 or 1; and
r is 0 to 3;
or the pharmaceutically acceptable salts thereof.

In a further embodiment of the formula A compounds of this invention, the inhibitors of farnesyl-protein transferase are illustrated by the formula A-i:

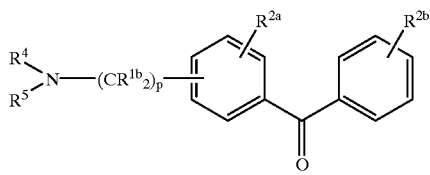

A-i wherein:

$R^{1b}$ is independently selected from:
 a) hydrogen,
 b) aryl, heterocycle, cycloalkyl, $R^{10}O-$, $-N(R^{10})_2$ or $C_2-C_6$ alkenyl,
 c) $C_1-C_6$ alkyl unsubstituted or substituted by aryl, heterocycle, cycloalkyl, alkenyl, $R^{10}O-$, or $-N(R^{10})_2$;

$R^{2a}$ and $R^{2b}$ are independently selected from:
 a) hydrogen,
 b) $C_1-C_6$ alkyl unsubstituted or substituted by $C_2-C_6$ alkenyl, $R^{10}O-$, $R^{11}S(O)_m-$, $R^{10}C(O)NR^{10}-$, CN, $N_3$, $(R^{10})_2N-C(NR^{10})-$, $R^{10}C(O)-$, $R^{10}C(O)-$, $-N(R^{10})_2$, or $R^{11}OC(O)NR^{10}-$,
 c) unsubstituted or substituted aryl, unsubstituted or substituted heterocycle, unsubstituted or substituted cycloalkyl, alkenyl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $R^{10}OC(O)-$, $N_3$, $-N(R^{10})_2$, halogen or $R^{11}OC(O)NR^{10}-$, and
 d) $C_1-C_6$ alkyl substituted with an unsubstituted or substituted group selected from aryl, heterocyclic and $C_3-C_{10}$ cycloalkyl;

$R^4$ is

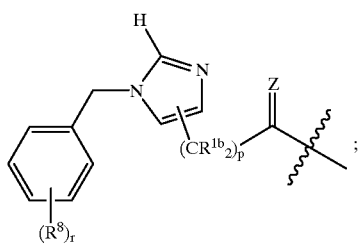

$R^5$ is hydrogen;
$R^8$ is independently selected from:
 a) hydrogen,
 b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
 c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{10}$ is independently selected from hydrogen, $C_1-C_6$ alkyl, substituted or unsubstituted $C_1-C_6$ aralkyl and substituted or unsubstituted aryl;
$R^{11}$ is independently selected from $C_1-C_6$ alkyl, benzyl and aryl;
Z is $H_2$ or O;
m is 0, or 2;
n is 0, 1, 2, 3 or 4;
p is independently 0, 1 or 2; and r is 0 to 5;

or the pharmaceutically acceptable salts thereof.

Specific compounds which are inhibitors of prenyl-protein transferases and are therefore useful in the present invention include:

1-[2(R)-Amino-3-mercaptopropyl]-2(S)-[(3-pyridyl)methoxyethyl)]-4-(1-naphthoyl)piperazine 1-[2(R)-Amino-3-mercaptopropyl]-2(S)-(benzyloxymethyl)-4-(1-naphthoyl)piperazine 1-[2(R)-Amino-3-mercaptopropyl]-2(S)-(benzyloxymethyl)-4-[7-(2,3-dihydrobenzofuroyl)]piperazine 1-[2(R)-Amino-3-mercaptopropyl]-2(S)-(benzamido)-4-(1-naphthoyl)piperazine 1-[2(R)-Amino-3-mercaptopropyl]-2(S)-[4-(5-dimethylamino-1-naphyhalenesulfonamido)-1-butyl]-4-(1-naphthoyl)piperazine N-[2(S)-(1-(4-Nitrophenylmethyl)-1H-imidazol-5-ylacetyl)amino-3(S)-methylpentyl]-N-1-naphthylmethyl-glycyl-methionine N-[2(S)-(1-(4-Nitrophenylmethyl)-1H-imidazol-5-ylacetyl)amino-3(S)-methylpentyl]-N-1-naphthylmethyl-glycyl-methionine methyl ester N-[2(S)-([1-(4-cyanobenzyl)-1H-imidazol-5-yl]acetylamino)-3(S)-methylpentyl]-N-(1-naphthylmethyl)glycyl-methionine N-[2(S)-([1-(4-cyanobenzyl)-1H-imidazol-5-yl]acetylamino)-3(S)-methylpentyl]-N-(1-naphthylmethyl)glycyl-methionine methyl ester 2(S)-n-Butyl-4-(1-naphthoyl)-1-[1-(2-naphthylmethyl)imidazol-5-ylmethyl]-piperazine 2(S)-n-Butyl-1-[1-(4-cyanobenzyl)imidazol-5-ylmethyl]-4-(1-naphthoyl)piperazine 1-{[1-(4-cyanobenzyl)-1H-imidazol-5-yl]acetyl}-2(S)-n-butyl-4-(1-naphthoyl)piperazine 1-(3-chlorophenyl)-4-[1-(4-cyanobenzyl)imidazolylmethyl]-2-piperazinone 1-phenyl-4-[1-(4-cyanobenzyl)-1H-imidazol-5-ylethyl]-piperazin-2-one 1-(3-trifluoromethylphenyl)-4-[1-(4-cyanobenzyl)-1H-imidazol-5-ylmethyl]-piperazin-2-one 1-(3-bromophenyl)-4-[1-(4-cyanobenzyl)-1H-imidazol-5-ylmethyl]-piperazin-2-one 5(S)-(2-[2,2,2-trifluoroethoxy]ethyl)-1-(3-trifluoromethylphenyl)-4-[1-(4-cyanobenzyl)-4-imidazolylmethyl]-piperazin-2-one 1-(5,6,7,8-tetrahydronaphthyl)-4-[1-(4-cyanobenzyl)-1H-imidazol-5-ylmethyl]-piperazin-2-one 1-(2-methyl-3-chlorophenyl)-4-[1-(4-cyanobenzyl)-4-imidazolylmethyl)]-piperazin-2-one 2(RS)-{[1-(Naphth-2-ylmethyl)-1H-imidazol-5-yl)]acetyl}amino-3-(t-butoxycarbonyl)amino-N-(2-methylbenzyl) propionamide N-{1-(4-Cyanobenzyl)-1H-imidazol-5-ylmethyl}-4(R)-benzyloxy-2(S)-{N'-acetyl-N'-3-chlorobenzyl}aminomethylpyrrolidine N-{1-(4-Cyanobenzyl)-1H-imidazol-5-ylethyl}-4(R)-benzyloxy-2(S)-{N'-acetyl-N'-3-chlorobenzyl laminomethyl pyrrolidine 1-[1-(4-Cyanobenzyl)-1H-imidazol-5-ylacetyl)]pyrrolidin-2(S)-ylmethyl]-(N-2-methylbenzyl)-glycine N'-(3-chlorophenylmethyl) amide 1-[1-(4-Cyanobenzyl)-1H-imidazol-5-ylacetyl]pyrrolidin-2(S)-ylmethyl]-(N-2-methylbenzyl)-glycine N'-methyl-N'-(3-chlorophenylmethyl) amide (S)-2-[(1-(4-Cyanobenzyl)-5-imidazolylmethyl)amino]-N-(benzyloxycarbonyl)-N-(3-chlorobenzyl)-4-(methanesulfonyl)butanamine 1-(3,5-Dichlorobenzenesulfonyl)-3 (S)-[N-(1-(4-cyanobenzyl)-1H-imidazol-5-ylethyl)carbamoyl] piperidine N-{[1-(4-Cyanobenzyl)-1H-imidazol-5-yl]methyl}-4-(3-methylphenyl)-4-hydroxy piperidine, N-{[1-(4-Cyanobenzyl)-1H-imidazol-5-yl]methyl}-4-(3-chlorophenyl)-4 hydroxy piperidine, 4-[1-(4-cyanobenzyl)-5-imidazolylmethyl]-1-(2,3-dimethylphenyl)-piperazine-2,3-dione 1-(2-(3-Trifluoromethoxyphenyl)-pyrid-5-ylmethyl)-5-(4-cyanobenzyl)imidazole 4-{5-[1-(3-Chloro-phenyl)-2-oxo-1,2-dihydro-pyridin-4-ylmethyl]-imidazol-1-ylmethyl}-2-methoxy-benzonitrile 3(R)-3-[1-(4-Cyanobenzyl)imidazol-5-yl-ethylamino]-5-phenyl-1-(2,2,2-trifluoroethyl)-H-benzo[e][1,4]diazepine 3(S)-3-[1-(4-Cyanobenzyl) imidazol-5-yl]-ethylamino]-5-phenyl-1-(2,2,2-trifluoroethyl)-H-benzo[e][1,4]diazepine N-[1-(4-Cyanobenzyl)-1H-imidazol-5-ylacetyl)pyrrolidin-2(S)-ylmethyl]-N-(1-naphthylmethyl)glycyl-methionine N-[1-(4-Cyanobenzyl)-1H-imidazol-5-ylacetyl)pyrrolidin-2(S)-ylmethyl]-N-(1-naphthylmethyl)glycyl-methionine methyl ester N-[1-(1H-Imidazol-4-ylpropionyl)pyrrolidin-2(S)-ylmethyl]-N-(2-methoxybenzyl)glycyl-methionine N-[1-(1H-Imidazol-4-ylpropionyl)pyrrolidin-2(S)-ylmethyl]-N-(2-methoxybenzyl)glycyl-methionine methyl ester 2(S)-(4-Acetamido-1-butyl)-1-[2(R)-amino-3-mercaptopropyl]-4-(1-naphthoyl)piperazine 2(RS)-{[1-(Naphth-2-ylmethyl)-1H-imidazol-5-yl)]acetyl}amino-3-(t-butoxycarbonyl)amino-N-cyclohexyl-propionamide 1-{2(R,S)-[1-(4-cyanobenzyl)-1H-imidazol-5-yl]propanoyl}-2(S)-n-butyl-4-(1-naphthoyl)piperazine 1-[1-(4-cyanobenzyl)imidazol-5-ylmethyl]-4-(diphenylmethyl)piperazine 1-(Diphenylmethyl)-3(S)-[N-(1-(4-cyanobenzyl)-2-methyl-1H-imidazol-5-ylethyl)-N-(acetyl)aminomethyl]piperidine N-[1-(1H-Imidazol-4-ylpropionyl)pyrrolidin-2(S)-ylmethyl]-N-(2-chlorobenzyl)glycyl-methionine N-[1-(1H-Imidazol-4-ylpropionyl)pyrrolidin-2(S)-ylmethyl]-N-(2-chlorobenzyl)glycyl-methionine methyl ester 3(R)-3-[1-(4-Cyanobenzyl)imidazol-5-yl-methylamino]-5-phenyl-1-(2,2,2-trifluoroethyl)-H-benzo[e][1,4]diazepine 1-(3-trifluoromethoxyphenyl)-4-[1-(4-cyanobenzyl)imidazolylmethyl]-2-piperazinone 1-(2,5-dimethylphenyl)-4-[1-(4-cyanobenzyl)imidazolylmethyl]-2-piperazinone 1-(3-methylphenyl)-4-[1-(4-cyanobenzyl)imidazolylmethyl]-2-piperazinone 1-(3-iodophenyl)-4-[1-(4-cyanobenzyl)imidazolylmethyl]-2-piperazinone 1-(3-chlorophenyl)-4-[1-(4-cyano-3-methoxybenzyl)imidazolylmethyl]-2-piperazinone 1-(3-trifluoromethoxyphenyl)-4-[1-(4-cyano-3-methoxybenzyl)imidazolyl methyl]-2-piperazinone 4-[((1-(4-cyanobenzyl)-5-imidazolyl)methyl)amino]benzophenone 1-(1-{[3-(4-cyano-benzyl)-3H-imidazol-4-yl]-acetyl}-pyrrolidin-2(S)-ylmethyl)-3(S)-ethyl-pyrrolidine-2(S)-carboxylic acid 3-chlorobenzylamide or the pharmaceutically acceptable salt thereof.

Compounds within the scope of this invention previously described as inhibitors of farnesyl-protein transferase but which have been further identified by the instant assays as inhibitors of prenylprotein transferases and are therefore useful in the present invention, and methods of synthesis thereof, can be found in the following patents, pending applications and publications, which are herein incorporated by reference:

U.S. Pat. No. 5,736,539 (Apr. 7, 1998); WO 95/00497 (Jan. 5, 1995)

U.S. Pat. No. 5,652,257 (Jul. 29, 1997); WO 96/10034 (Apr. 4, 1996) WO 96/30343 (Oct. 3, 1996); U.S. Ser. No. 08/412,829 filed on Mar. 29, 1995, now abandoned; and Ser. No. 08/470,690 filed on Jun. 6, 1995, now abandoned; and U.S. Ser. No. 08/600,728 filed on Feb. 28, 1996, now U.S. Pat. No. 5,856,326

U.S. Pat. No. 5,661,161 (Aug. 26, 1997);

U.S. Pat. No. 5,756,528 (May 6, 1998); WO 96/39137 (Dec. 12, 1996);

WO 96/37204 (Nov. 28, 1996); U.S. Ser. No. 08/449,038 filed on May 24, 1995, now abandoned; U.S. Ser. No. 08/648,330 filed on May 15, 1996, now U.S. Pat. No. 5,710,171;

WO 97/18813 (May 29, 1997); U.S. Ser. No. 08/749,254 filed on Nov. 15, 1996, now U.S. Pat. No. 5,817,678, WO 97/38665 (Oct. 23, 1997); U.S. Ser. No. 08/831,308 filed on Apr. 1, 1997, now U.S. Pat. No. 5,891,889;

WO 97/36889 (Oct. 9, 1997); U.S. Ser. No. 08/823,923 filed on Mar. 25, 1997, now U.S. Pat. No. 5,889,012;

WO 97/36901 (Oct. 9, 1997); U.S. Ser. No. 08/827,483 filed on Mar. 27, 1997, now U.S. Pat. No. 5,872,136;

WO 97/36879 (Oct. 9, 1997); U.S. Ser. No. 08/823,920 filed on Mar. 25, 1997, now U.S. Pat. No. 5,852,010;

WO 97/36605 (Oct. 9, 1997); U.S. Ser. No. 08/823,934 filed on Mar. 25, 1997, now U.S. Pat. No. 5,965,578;

WO 98/28980, (Jul. 9, 1998); U.S. Ser. No. 08/997,171 filed on Dec. 22, 1997; and U.S. Ser. No. 60/014,791 filed on Apr. 3, 1996; U.S. Ser. No. 08/831,308, filed on Apr. 4, 1997, now U.S. Pat. No. 5,891,889.

All patents, publications and pending patent applications identified are hereby incorporated by reference.

With respect to the compounds of formulas I through IIIa the following definitions apply:

The term "alkyl" refers to a monovalent alkane (hydrocarbon) derived radical containing from 1 to 15 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

When substituted alkyl is present, this refers to a straight, branched or cyclic alkyl group as defined above, substituted with 1–3 groups as defined with respect to each variable.

Heteroalkyl refers to an alkyl group having from 2–15 carbon atoms, and interrupted by from 1–4 heteroatoms selected from O, S and N.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (nonresonating) carbon-carbon double bonds may be present. Examples of alkenyl groups include vinyl, allyl, iso-propenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

Aryl refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl and naphthyl substituted with one or two groups. With regard to the farnesyl transferase inhibitors, "aryl" is intended to include any stable monocyclic, bicyclic or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl and the like.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to three groups.

Heteroaryl thus includes aromatic and partially aromatic groups which contain one or more heteroatoms. Examples of this type are thiophene, purine, imidazopyridine, pyridine, oxazole, thiazole, oxazine, pyrazole, tetrazole, imidazole, pyridine, pyrimidine, pyrazine and triazine. Examples of partially aromatic groups are tetrahydro-imidazo[4,5-c]pyridine, phthalidyl and saccharinyl, as defined below.

With regard to the farnesyl transferase inhibitors, the term heterocycle or heterocyclic, as used herein, represents a stable 5- to 7-membered monocyclic or stable 8- to 11-membered bicyclic or stable 11–15 membered tricyclic heterocycle ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, and thienyl. Preferably, heterocycle is selected from imidazolyl, 2-oxopyrrolidinyl, piperidyl, pyridyl and pyrrolidinyl.

With regard to the farnesyl transferase inhibitors, the terms "substituted aryl", "substituted heterocycle" and "substituted cycloalkyl" are intended to include the cyclic group which is substituted with 1 or 2 substituents selected from the group which includes but is not limited to F, Cl, Br, $CF_3$, $NH_2$, $N(C_1-C_6 \text{ alkyl})_2$, $NO_2$, CN, $(C_1-C_6 \text{ alkyl})O—$, $—OH$, $(C_1-C_6 \text{ alkyl})S(O)_m—$, $(C_1-C_6 \text{ alkyl})C(O)NH—$, $H_2N—C(NH)—$, $(C_1-C_6 \text{ alkyl})C(O)—$, $(C_1-C_6 \text{ alkyl})OC(O)—$, $N_3$, $(C_1-C_6 \text{ alkyl})OC(O) \text{ NH}—$ and $C_1-C_{20}$ alkyl.

In the present method, amino acids which are disclosed are identified both by conventional 3 letter and single letter abbreviations as indicated below:

| | | |
|---|---|---|
| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V | with respect to the term "CAAX" the letter "A" represents an aliphatic amino acid and is not limited to alanine.

The compounds used in the present method may have asymmetric centers and occur as racemates, racemic mixtures, and as individual diastereomers, with all possible isomers, including optical isomers, being included in the present invention. Unless otherwise specified, named amino acids are understood to have the natural "L" stereoconfiguration When $R^2$ and $R^3$ are combined to form $—(CH_2)_u—$, cyclic moieties are formed. Examples of such cyclic moieties include, but are not limited to:

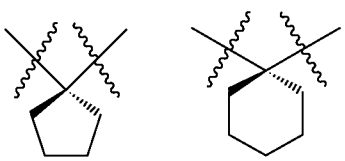

In addition, such cyclic moieties may optionally include a heteroatom(s). Examples of such heteroatom-containing cyclic moieties include, but are not limited to:

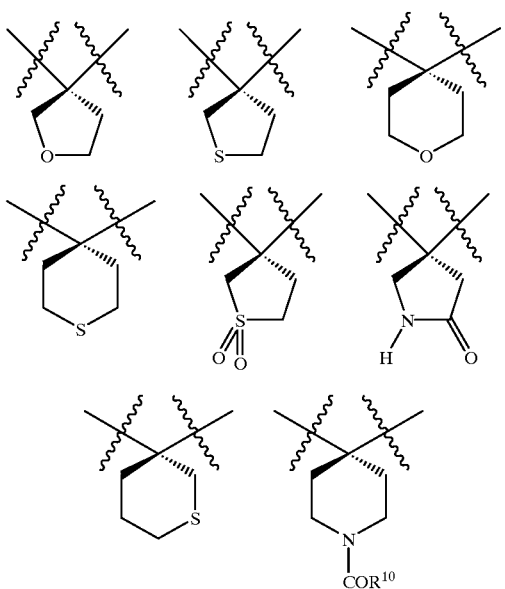

When $R^6$ and $R^7$, $R^7$ and $R^{7a}$, or are combined to form —$(CH_2)_u$—, cyclic moieties are formed. Examples of such cyclic moieties include, but are not limited to:

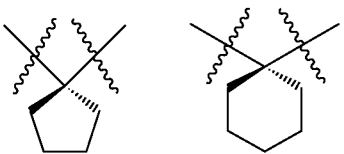

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{10}$, Z, n, etc.) at a particular location in a molecule be independent of its definitions elsewhere in that molecule. Thus, —$N(R^{10})_2$ represents —NHH, —$NHCH_3$, —$NHC_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

Peptidyl compounds useful in the instant methods can be synthesized from their constituent amino acids by conventional peptide synthesis techniques, and the additional methods described below. Standard methods of peptide synthesis are disclosed, for example, in the following works: Schroeder et al., "The Peptides", Vol. I, Academic Press 1965, or Bodanszky et al., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984. Also useful in exemplifying syntheses of specific unnatural amino acid residues are European Pat. Appl. No. 0 350 163 A2 (particularly page 51–52) and J. E. Baldwin et al Tetrahedron, 50:5049–5066 (1994). With regards to the synthesis of such peptidyl compounds containing a (β-acetylamino)alanine residue at the C-terminus, use of the commercially available Nα-Z-L-2,3-diaminopropionic acid (Fluka) as a starting material is preferred.

Abbreviations used in the description of the chemistry and in the Examples that follow are:

$Ac_2O$ Acetic anhydride;
Boc t-Butoxycarbonyl;
DBU 1,8-diazabicyclo[5.4.0]undec-7-ene;
DMAP 4-Dimethylaminopyridine;
DME 1,2-Dimethoxyethane;
DMF Dimethylformamide;
$EDC_1$-(3-dimethylaminopropyl)-3-ethyl-carbodiimide-hydrochloride;
HOBT 1-Hydroxybenzotriazole hydrate;
$Et_3N$ Triethylamine;
EtOAc Ethyl acetate;
FAB Fast atom bombardment;
HOOBT 3-Hydroxy-1,2,2-benzotriazin-4(3H)-one;
HPLC High-performance liquid chromatography;
MCPBA m-Chloroperoxybenzoic acid;
MsCl Methanesulfonyl chloride;
NaHMDS Sodium bis(trimethylsilyl)amide;
Py Pyridine;
TFA Trifluoroacetic acid;
THF Tetrahydrofuran.

The compounds are useful in various pharmaceutically acceptable salt forms. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

Pharmaceutically acceptable salts include conventional non-toxic salts or quarternary ammonium salts formed, e.g., from non-toxic inorganic or organic acids. Non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, sulfanilic, 2-acetoxybenzoic, fumaric, toluenesulfonic, methanesulfonic, ethane disulfonic, oxalic, isethionic, trifluoroacetic and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The prenyl transferase inhibitors of formula (I) can be synthesized in accordance with Schemes 1–11, in addition to other standard manipulations such as ester hydrolysis, cleavage of protecting groups, etc., as may be known in the literature or exemplified in the experimental procedures. Substituents R, $R^a$ and $R^b$, as shown in the Schemes, represent the substituents $R^2$, $R^3$, $R^4$, and $R^5$; however their point of attachment to the ring is illustrative only and is not meant to be limiting.

These reactions may be employed in a linear sequence to provide the compounds of the invention or they may be used to synthesize fragments which are subsequently joined by the alkylation reactions described in the Schemes.

Synopsis of Schemes 1–11

The requisite intermediates are in some cases commercially available, or can be prepared according to literature procedures, for the most part.

Piperazin-5-ones can be prepared as shown in Scheme 1. Thus, the protected suitably substituted amino acid IV can be converted to the corresponding aldehyde V by first forming the amide and then reducing it with LAH. Reductive amination of Boc-protected amino aldehydes V gives rise to compound VI. The intermediate VI can be converted to a piperazinone by acylation with chloroacetyl chloride to give VII, followed by base-induced cyclization to VIII. Deprotection, followed by reductive alkylation with a protected imidazole carboxaldehyde leads to IX, which can be alkylated with an arylmethylhalide to give the imidazolium salt X. Final removal of protecting groups by either solvolysis with a lower alkyl alcohol, such as methanol, or treatment with triethylsilane in methylene chloride in the presence of trifluoroacetic acid gives the final product XI.

The intermediate VIII can be reductively alkylated with a variety of aldehydes, such as XII. The aldehydes can be prepared by standard procedures, such as that described by O. P. Goel, U. Krolls, M. Stier and S. Kesten in *Organic Syntheses*, 1988, 67, 69–75, from the appropriate amino acid (Scheme 2). The reductive alkylation can be accomplished at pH 5–7 with a variety of reducing agents, such as sodium triacetoxyborohydride or sodium cyanoborohydride in a solvent such as dichloroethane, methanol or dimethylformamide. The product XIII can be deprotected to give the final compounds XIV with trifluoroacetic acid in methylene chloride. The final product XIV is isolated in the salt form, for example, as a trifluoroacetate, hydrochloride or acetate salt, among others. The product diamine XIV can further be selectively protected to obtain XV, which can subsequently be reductively alkylated with a second aldehyde to obtain XVI. Removal of the protecting group, and conversion to cyclized products such as the dihydroimidazole XVII can be accomplished by literature procedures.

Alternatively, the imidazole acetic acid XVIII can be converted to the acetate XIX by standard procedures, and XIX can be first reacted with an alkyl halide, then treated with refluxing methanol to provide the regiospecifically alkylated imidazole acetic acid ester XX (Scheme 3). Hydrolysis and reaction with piperazinone VIII in the presence of condensing reagents such as 1-(3-dimethylaminopropyl)-3-ethylcarbodiimide (EDC) leads to acylated products such as XXI.

If the piperazinone VIII is reductively alkylated with an aldehyde which also has a protected hydroxyl group, such as XXII in Scheme 4, the protecting groups can be subsequently removed to unmask the hydroxyl group (Schemes 4, 5). The alcohol can be oxidized under standard conditions to e.g. an aldehyde, which can then be reacted with a variety of organometallic reagents such as Grignard reagents, to obtain secondary alcohols such as XXIV. In addition, the fully deprotected amino alcohol XXV can be reductively alkylated (under conditions described previously) with a variety of aldehydes to obtain secondary amines, such as XXVI (Scheme 5), or tertiary amines.

The Boc protected amino alcohol XXIII can also be utilized to synthesize 2-aziridinylmethylpiperazinones such as XXVII (Scheme 6). Treating XXIII with 1,1'-sulfonyldiimidazole and sodium hydride in a solvent such as dimethylformamide led to the formation of aziridine XXVII. The aziridine reacted in the presence of a nucleophile, such as a thiol, in the presence of base to yield the ring-opened product XXVIII.

In addition, the piperazinone VIII can be reacted with aldehydes derived from amino acids such as O-alkylated tyrosines, according to standard procedures, to obtain compounds such as XXX (Scheme 7). When R' is an aryl group, XXX can first be hydrogenated to unmask the phenol, and the amine group deprotected with acid to produce XXXI. Alternatively, the amine protecting group in XXX can be removed, and O-alkylated phenolic amines such as XXXII produced.

Scheme 8 illustrates the use of an optionally substituted homoserine lactone XXXIII to prepare a Boc-protected piperazinone XXXVII. Intermediate XXXVII may be deprotected and reductively alkylated or acylated as illustrated in the previous Schemes. Alternatively, the hydroxyl moiety of intermediate XXXVII may be mesylated and displaced by a suitable nucleophile, such as the sodium salt of ethane thiol, to provide an intermediate XXXVIII. Intermediate XXXVII may also be oxidized to provide the carboxylic acid on intermediate IXL, which can be utilized form an ester or amide moiety.

N-Aralkyl-piperazin-5-ones can be prepared as shown in Scheme 9. Reductive amination of Boc-protected amino aldehydes V (prepared from III as described previously) gives rise to compound XL. This is then reacted with bromoacetyl bromide under Schotten-Baumann conditions; ring closure is effected with a base such as sodium hydride in a polar aprotic solvent such as dimethylformamide to give XLI. The carbamate protecting group is removed under acidic conditions such as trifluoroacetic acid in methylene chloride, or hydrogen chloride gas in methanol or ethyl acetate, and the resulting piperazine can then be carried on to final products as described in Schemes 1–7.

The isomeric piperazin-3-ones can be prepared as described in Scheme 10. The imine formed from arylcarboxamides XLII and 2-aminoglycinal diethyl acetal (XLIII) can be reduced under a variety of conditions, including sodium triacetoxyborohydride in dichloroethane, to give the amine XLIV. Amino acids I can be coupled to amines XLIV under standard conditions, and the resulting amide XLV when treated with aqueous acid in tetrahydrofuran can cyclize to the unsaturated XLVI. Catalytic hydrogenation under standard conditions gives the requisite intermediate XLVII, which is elaborated to final products as described in Schemes 1–7.

Amino acids of the general formula IL which have a sidechain not found in natural amino acids may be prepared by the reactions illustrated in Scheme 11 starting with the readily prepared imine XLVIII.

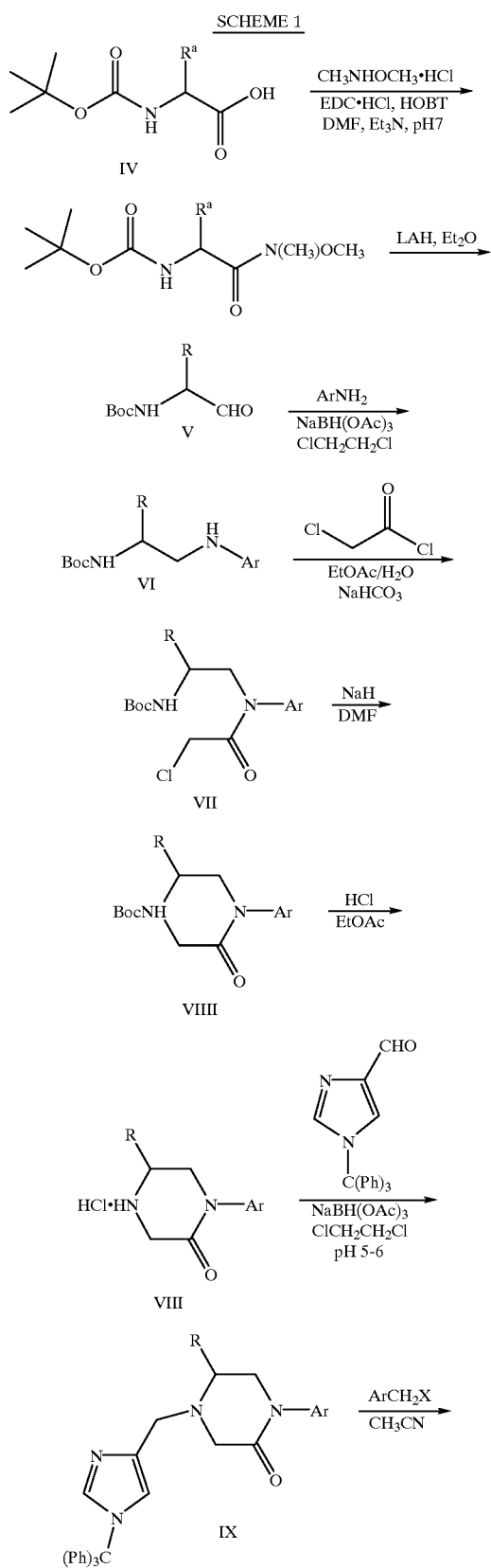
SCHEME 1
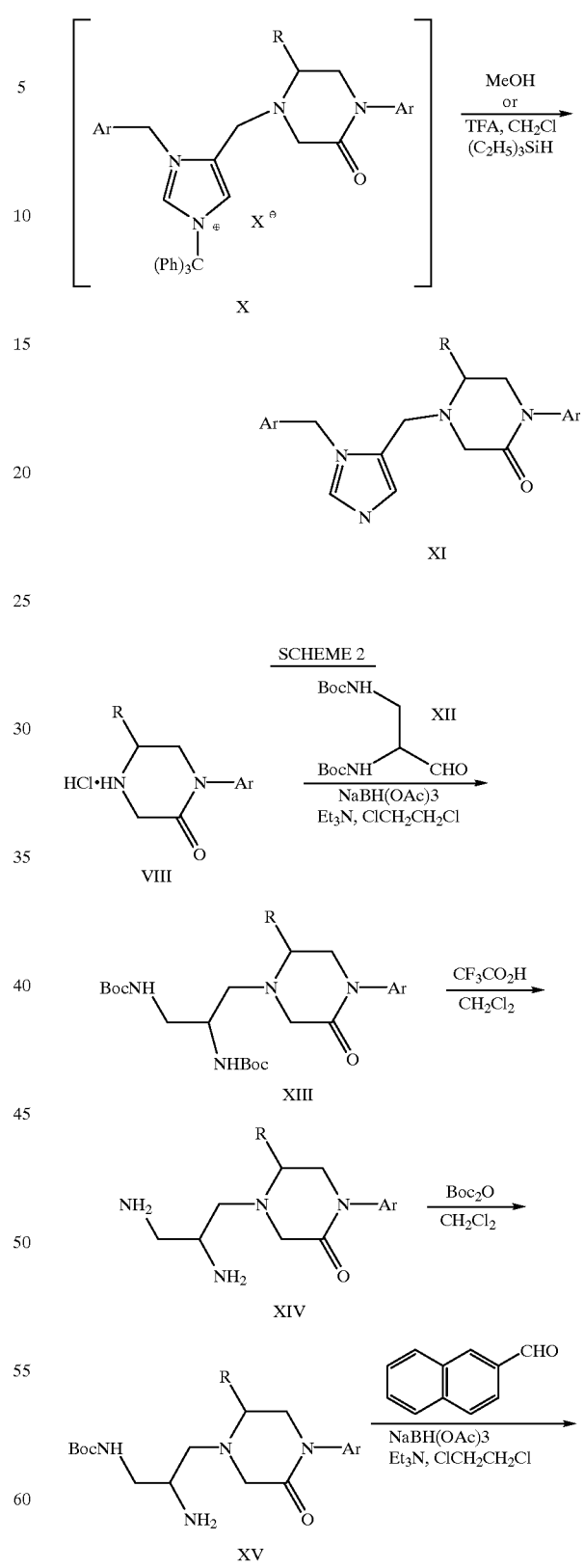
SCHEME 2

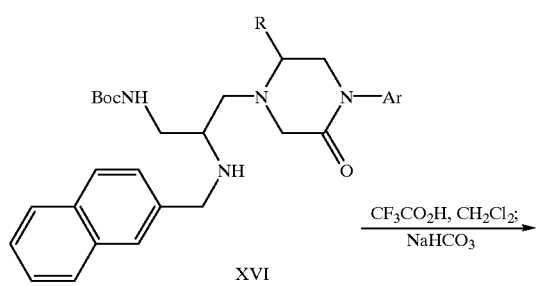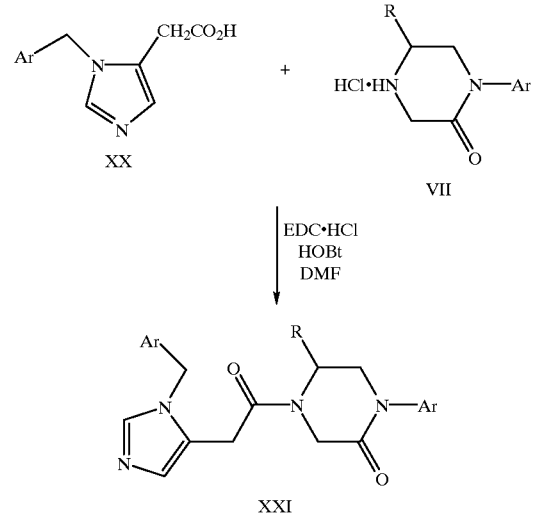

SCHEME 5
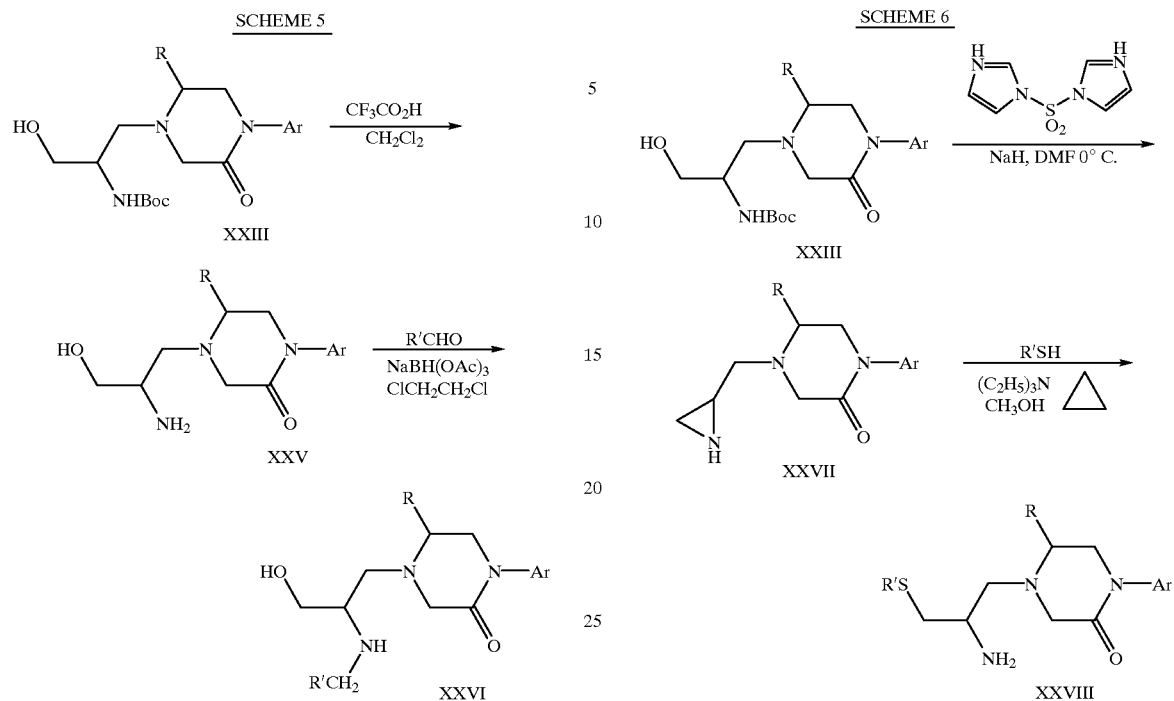
SCHEME 6
SCHEME 7
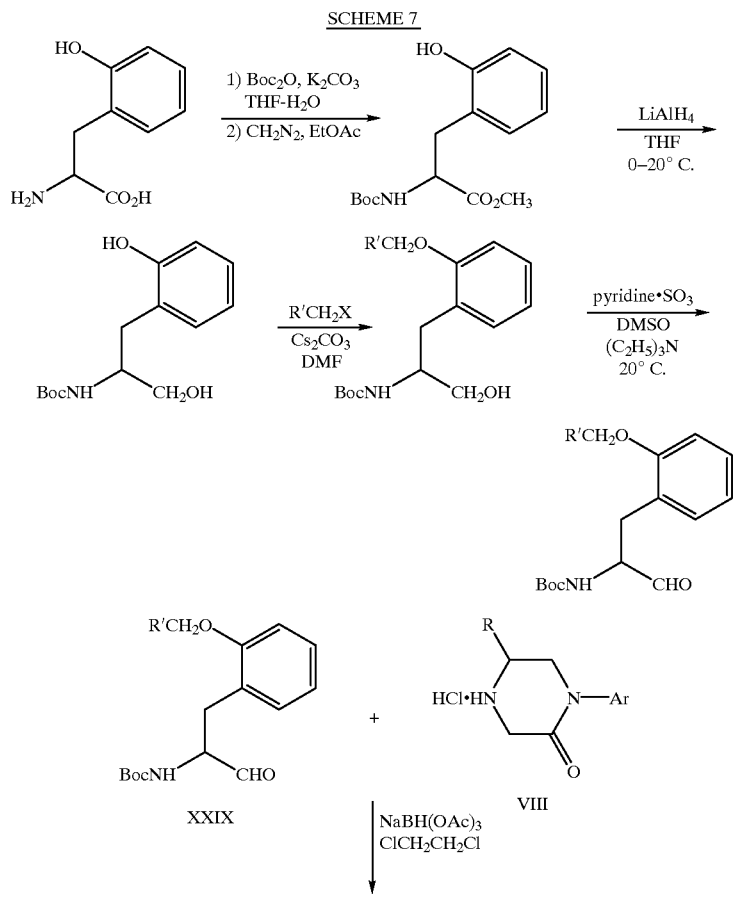

-continued
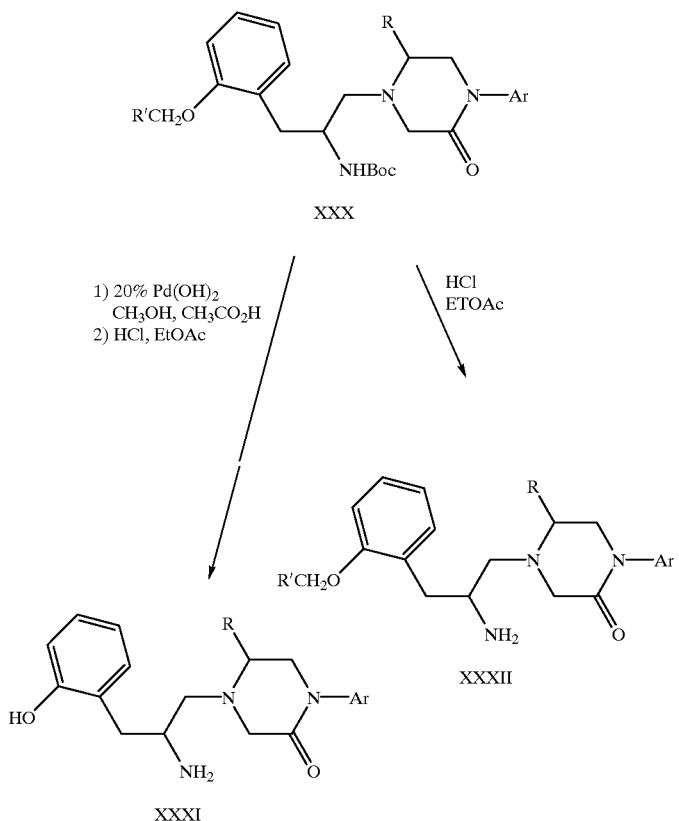
SCHEME 8
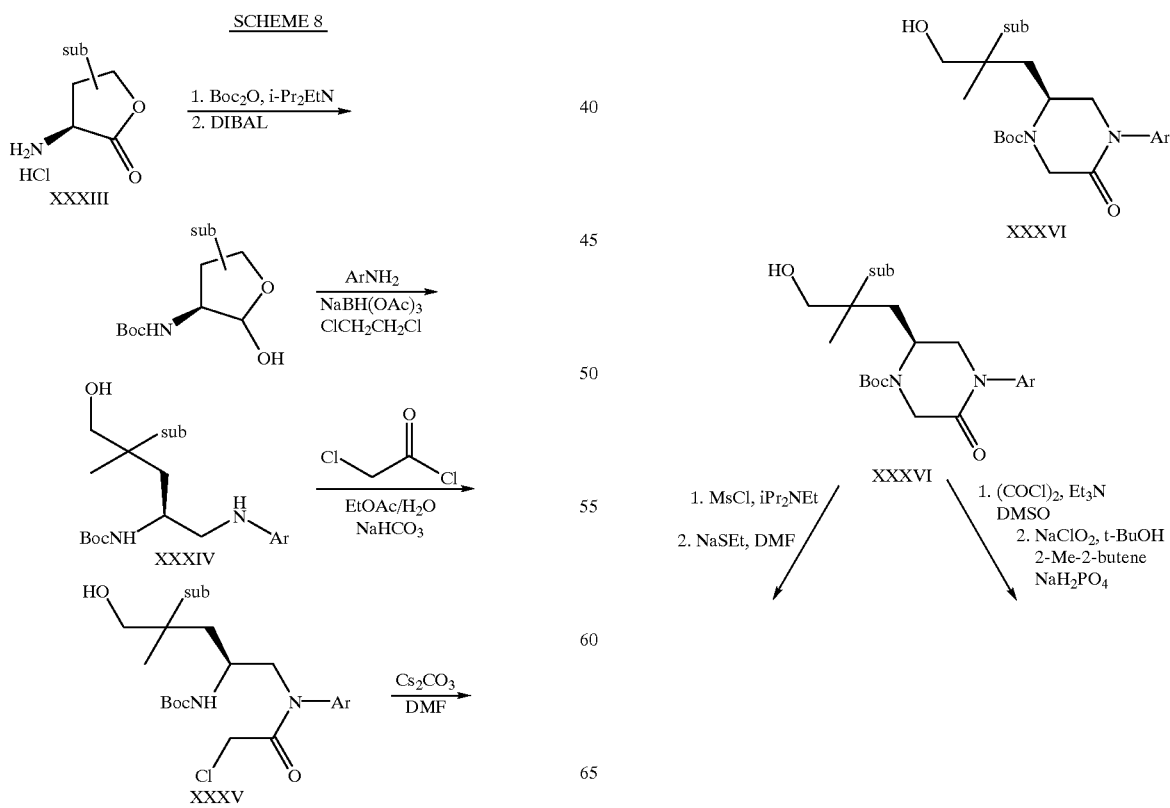

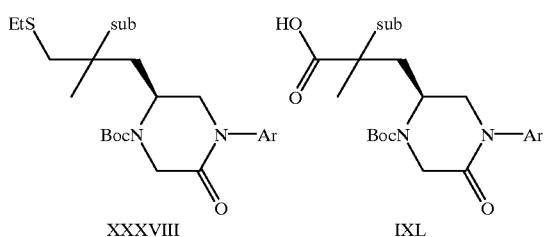

XXXVIII    IXL

SCHEME 9

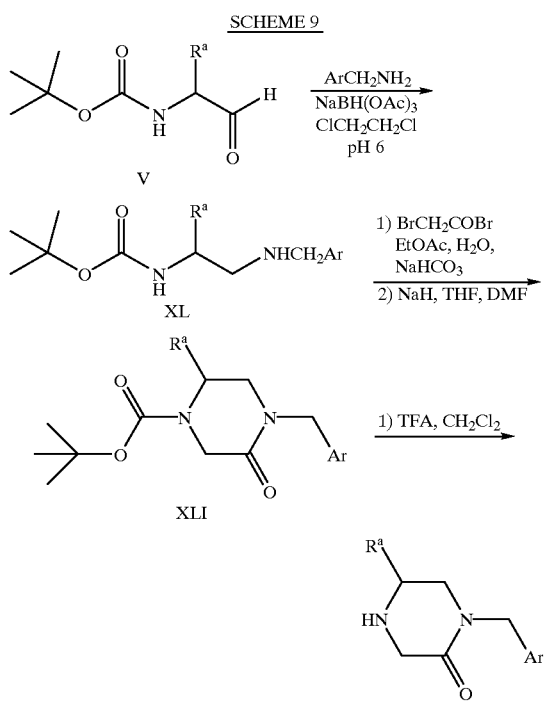

SCHEME 10

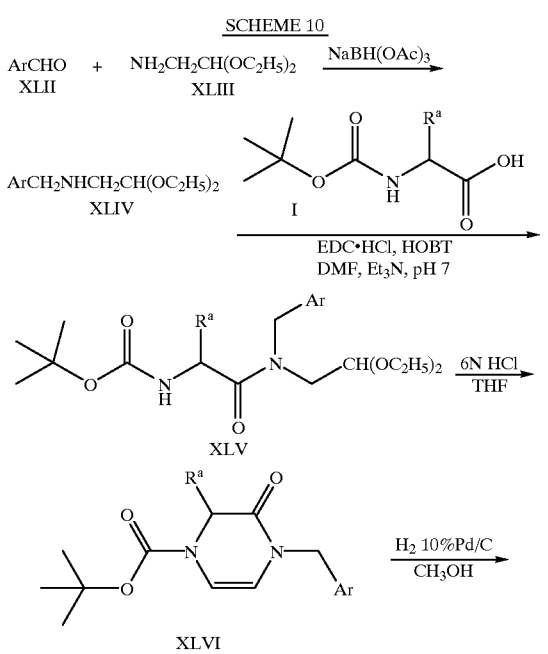

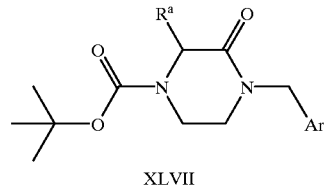

XLVII

SCHEME 11

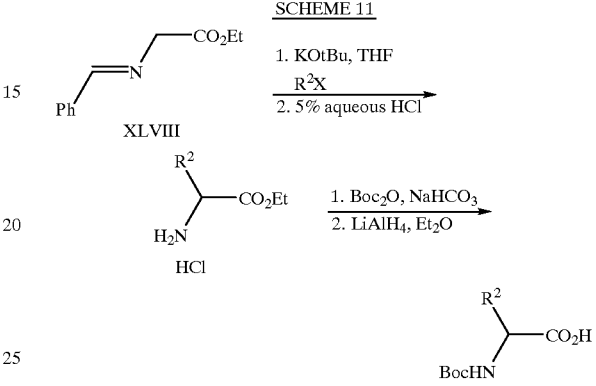

Reactions used to generate the compounds of the formula (II) are prepared by employing reactions as shown in the Schemes 16–37, in addition to other standard manipulations such as ester hydrolysis, cleavage of protecting groups, etc., as may be known in the literature or exemplified in the experimental procedures. Substituents $R^a$ and $R^b$, as shown in the Schemes, represent the substituents $R^2$, $R^3$, $R^4$, and $R^5$; substituent "sub" represents a suitable substituent on the substituent Z. The point of attachment of such substituents to a ring is illustrative only and is not meant to be limiting.

These reactions may be employed in a linear sequence to provide the compounds of the invention or they may be used to synthesize fragments which are subsequently joined by the alkylation reactions described in the Schemes.

Synopsis of Schemes 16–37

The requisite intermediates utilized as starting material in the Schemes hereinbelow are in some cases commercially available, or can be prepared according to literature procedures. In Scheme 16, for example, a suitably substituted Boc protected isonipecotate LI may be deprotonated and then treated with a suitably substituted alkylating group, such as a suitably substituted benzyl bromide, to provide the gem disubstituted intermediate LIII. Deprotection and reduction provides the hydroxymethyl piperidine LIV which can be utilized is synthesis of compounds of the invention or which may be nitrogen-protected and methylated to give the intermediate LV.

As shown in Scheme 17, the protected piperidine intermediate LIII can be deprotected and reductively alkylated with aldehydes such as 1-trityl-4-imidazolyl-carboxaldehyde or 1-trityl-4-imidazolylacetaldehyde, to give products such as LVI. The trityl protecting group can be removed from LVI to give LVII, or alternatively, LVI can first be treated with an alkyl halide then subsequently deprotected to give the alkylated imidazole LVIII.

The deprotected intermediate LIII can also be reductively alkylated with a variety of other aldehydes and acids as shown above in Schemes 4–7.

An alternative synthesis of the hydroxymethyl intermediate LIV and utilization of that intermediate in the synthesis of the instant compounds which incorporate the preferred imidazolyl moiety is illustrated in Scheme 18. Scheme 19 illustrates the reductive alkylation of intermediate LIV to provide a 4-cyanobenzylimidazolyl substituted piperidine. The cyano moiety may be selectively hydrolyzed with sodium borate to provide the corresponding amido compound of the instant invention.

Scheme 20 alternative preparation of the methyl ether intermediate LV and the alkylation of LV with a suitably substituted imidazolylmethyl chloride to provide the instant compound. Preparation of the homologous 1-(imidazolylethyl)piperidine is illustrated in Scheme 21.

Specific substitution on the piperidine of the compounds of the instant invention may be accomplished as illustrated in Scheme 22. Thus, metal-halogen exchange coupling of a butynyl moiety to an isonicotinate, followed by hydrogenation, provides the 2-butylpiperidine intermediate that can then undergo the reactions previously described to provide the compound of the instant invention.

Incorporation of a 4-amido moiety for LV is illustrated in Scheme 23.

Scheme 24 illustrates the synthesis of the instant compounds wherein the moiety Z is attached directly to the piperidine ring. Thus the piperidone LIX is treated with a suitably substituted phenyl Grignard reagent to provide the gem disubstituted piperidine LX. Deprotection provides the key intermediate LXI. Intermediate LXI may be acetylated as described above to provide the instant compound LXII (Scheme 25).

As illustrated in Scheme 26, the protected piperidine LX may be dehydrated and then hydroborated to provide the 3-hydroxypiperidine LXIII. This compound may be deprotected and further derivatized to provide compounds of the instant invention (as shown in Scheme 27) or the hydroxyl group may be alkylated, as shown in Scheme 26, prior to deprotection and further manipulation.

The dehydration product may also be catalytically reduced to provide the des-hydroxy intermediate LXV, as shown in Scheme 28, which can be processed via the reactions illustrated in the previous Schemes.

Schemes 29 and 30 illustrate further chemical manipulations of the 4-carboxylic acid functionality to provide instant compounds wherein the substituent Y is an acetylamine or sulfonamide moiety.

Scheme 31 illustrates incorporation of a nitrile moiety in the 4-position of the piperidine of the compounds of formula II. Thus, the hydroxyl moiety of a suitably substituted 4-hydroxypiperidine is substituted with nitrile to provide intermediate LXVI, which can undergo reactions previously described in Schemes 17–21.

Scheme 32 illustrates the preparation of several pyridyl intermediates that may be utilized with the piperidine intermediates such as compound LI in Scheme 16 to provide the instant compounds. Scheme 33 shows a generalized reaction sequence which utilizes such pyridyl intermediates.

Compounds of the instant invention wherein $X^1$ is a carbonyl moiety may be prepared as shown in Scheme 34. Intermediate LXVII may undergo subsequent reactions as illustrated in Schemes 17–21 to provide the instant compounds. Preparation of the instant compounds wherein $X^1$ is sulfur in its various oxidation states is shown in Scheme 35. Intermediates LXVIII–LXXI may undergo the previously described reactions to provide the instant compounds.

Scheme 36 illustrated preparation of compounds of the formula A wherein Y is hydrogen. Thus, suitably substituted isonipecotic acid may be treated with N,O-dimethylhydroxylamine and the intermediate LXXII reacted with a suitably substituted phenyl Grignard reagent to provide intermediate LXXIII. That intermediate may undergo the reactions previously described in Schemes 17–21 and may be further modified by reduction of the phenyl ketone to provide the alcohol LXXIV.

Compounds of the instant invention wherein $X^1$ is an amine moiety may be prepared as shown in Scheme 37. Thus the N-protected 4-piperidinone may be reacted with a suitably substituted aniline in the presence of trimethylsilylcyanide to provide the 4-cyano-4-aminopiperidine LXXV. Intermediate LXXV may then be converted in sequence to the corresponding amide LXXVI, ester LXXVII and alcohol LXXVIII. Intermediates LXXVI–LXXVIII can be deprotected and can then undergo the reactions previously described in Schemes 17–21 to provide the compounds of the instant invention.

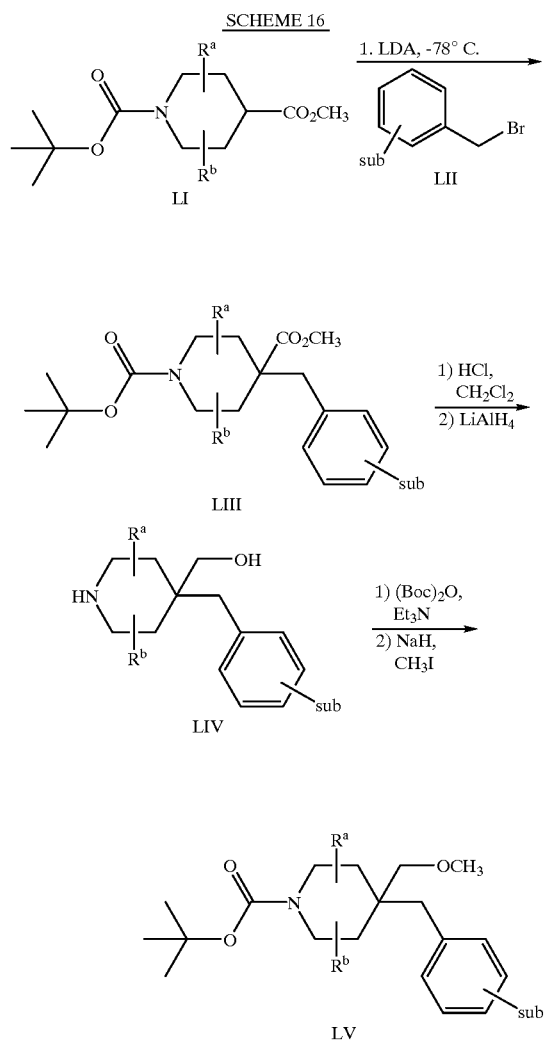

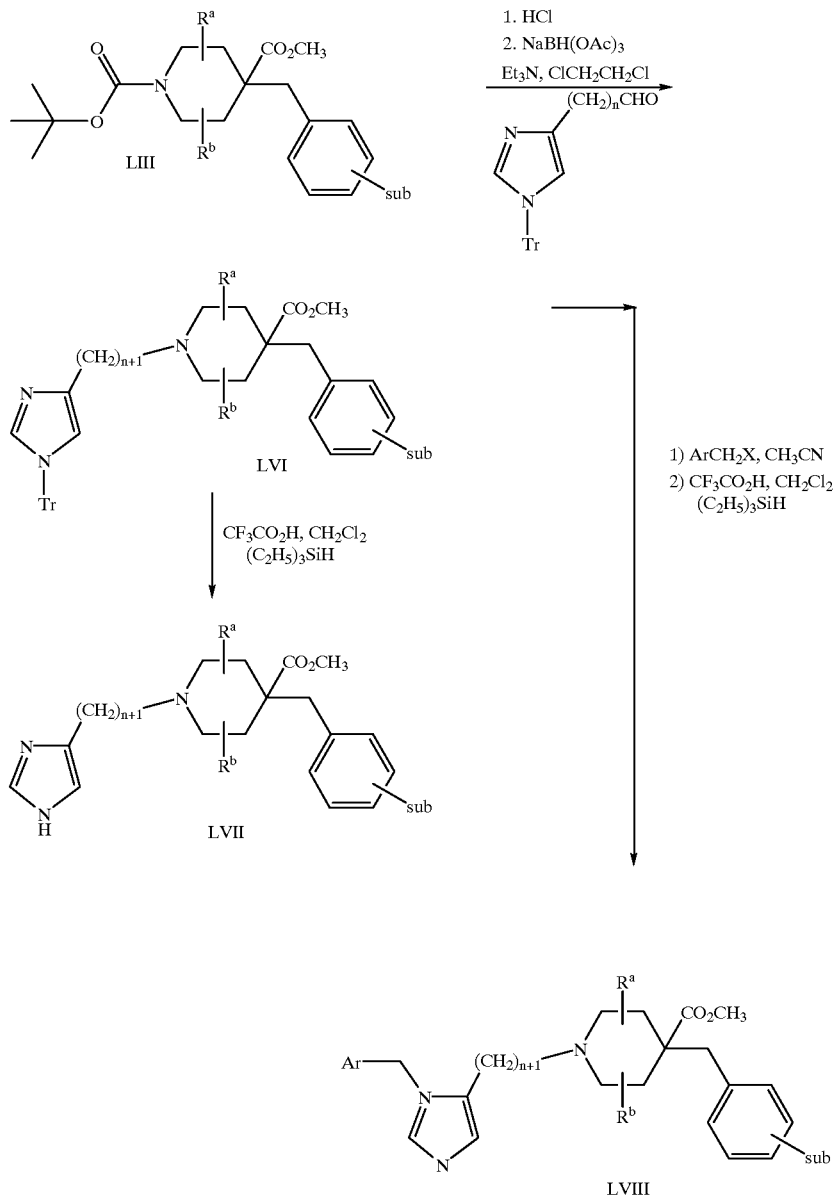
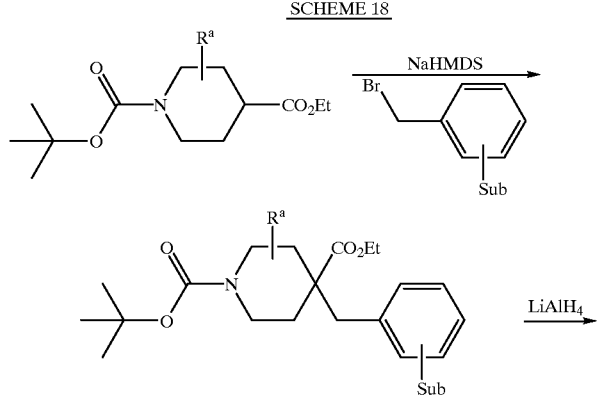

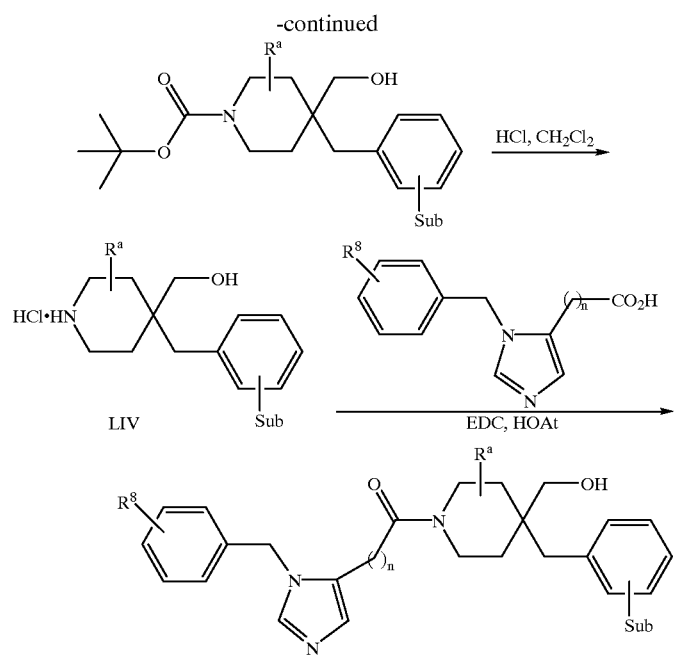
SCHEME 19
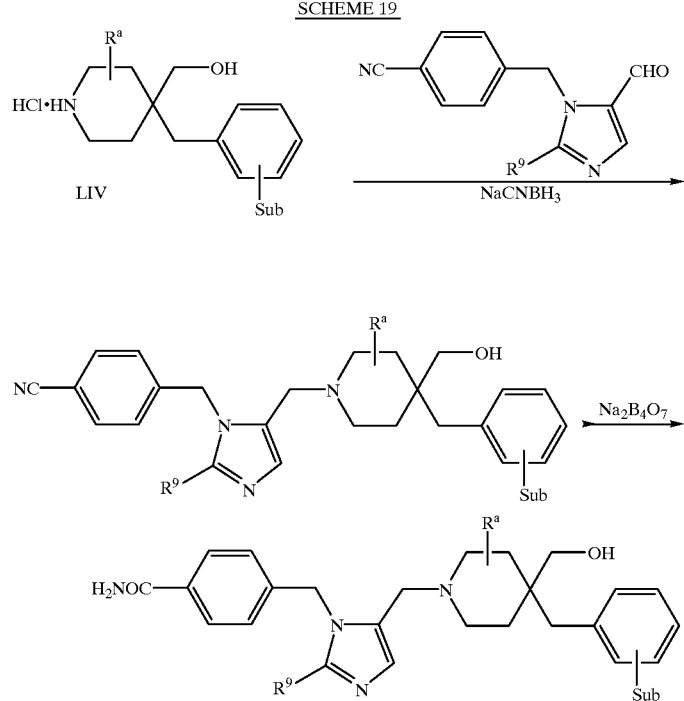

SCHEME 20
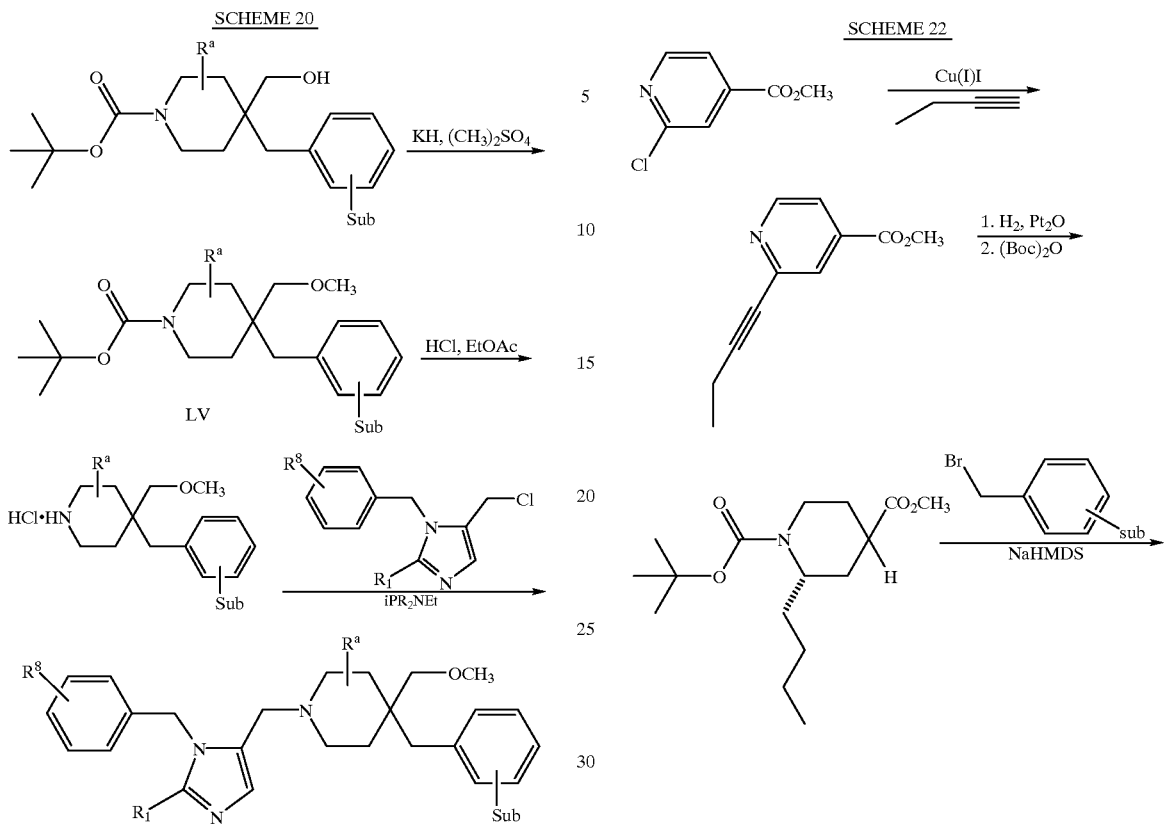
SCHEME 22
SCHEME 21
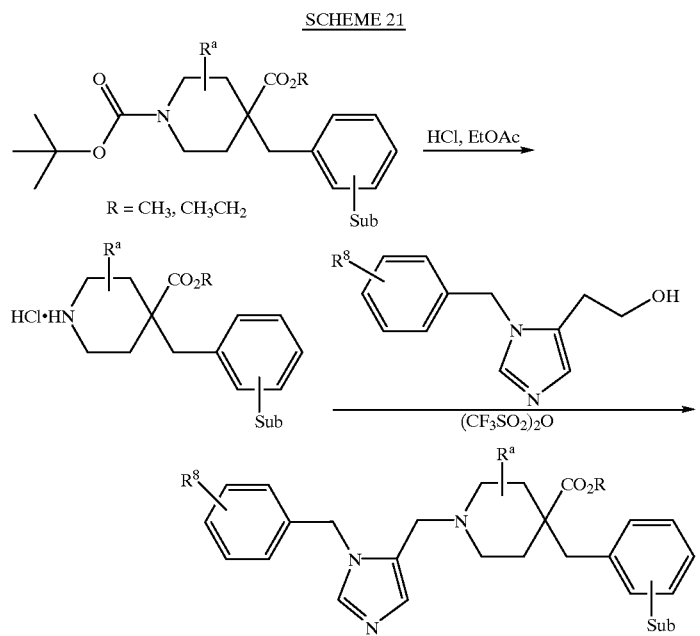

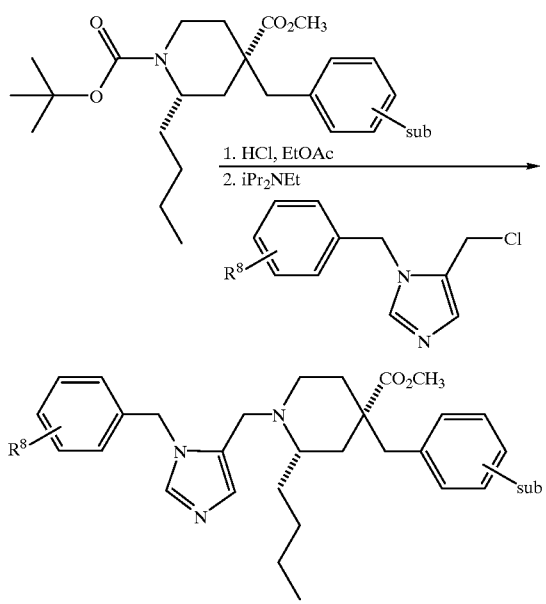
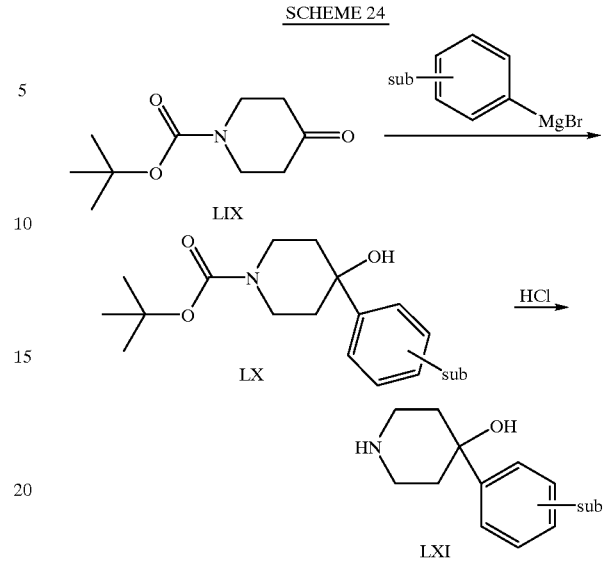
SCHEME 23
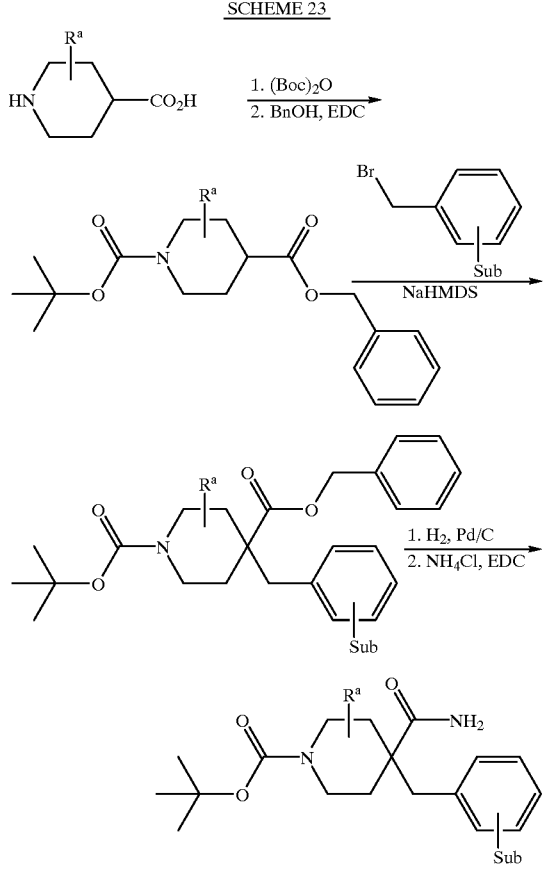
SCHEME 25
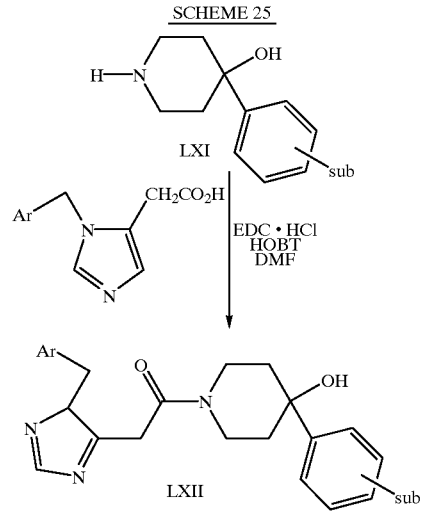
SCHEME 26
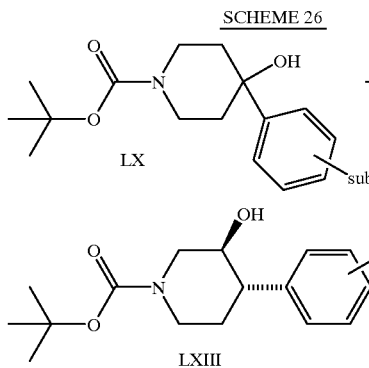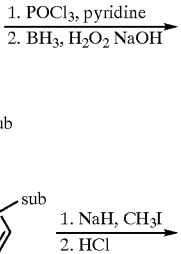

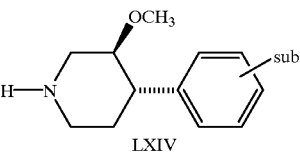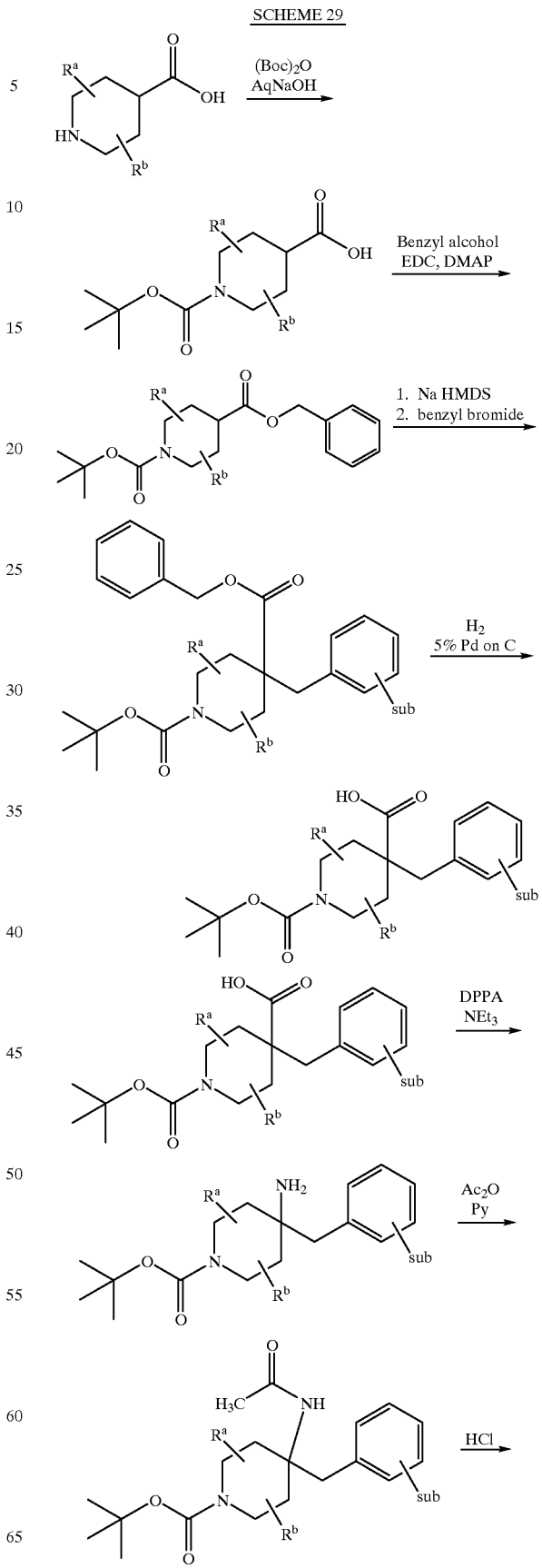

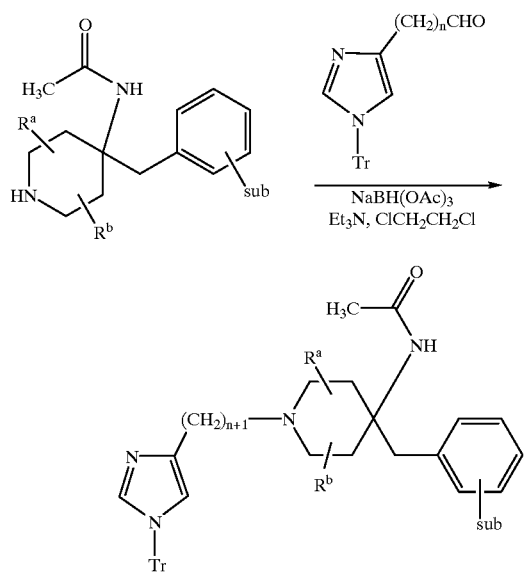
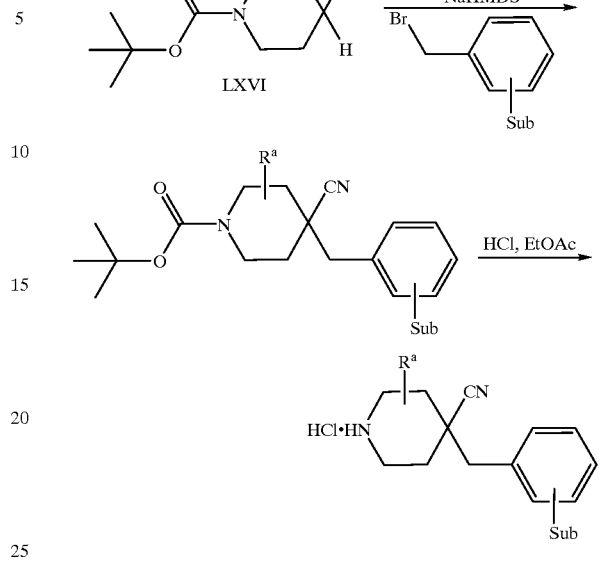
SCHEME 30
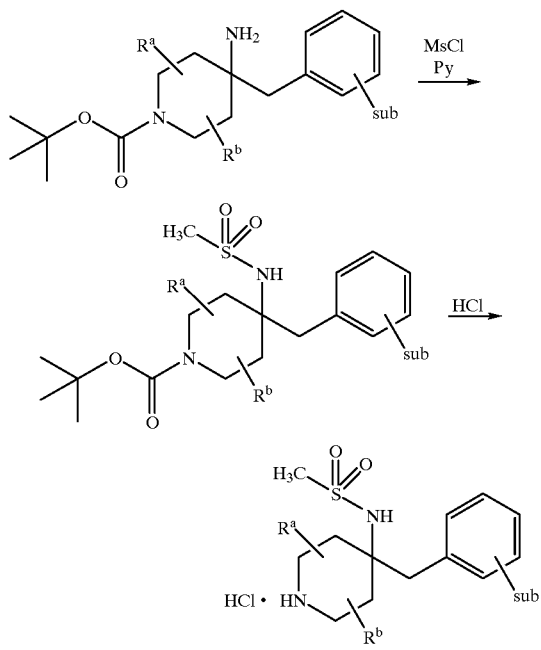
SCHEME 31
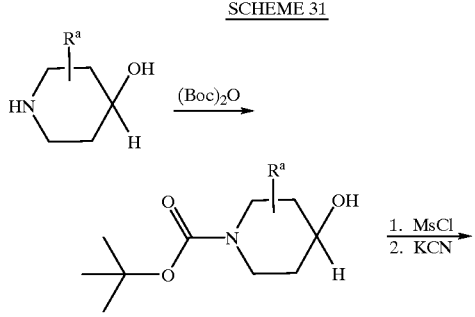
SCHEME 32
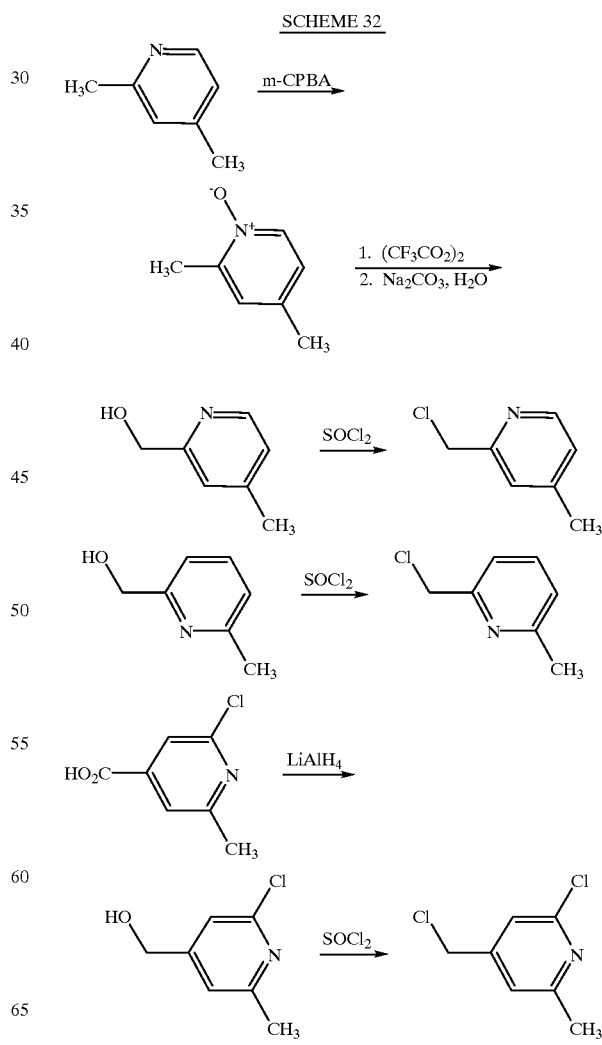

61
-continued
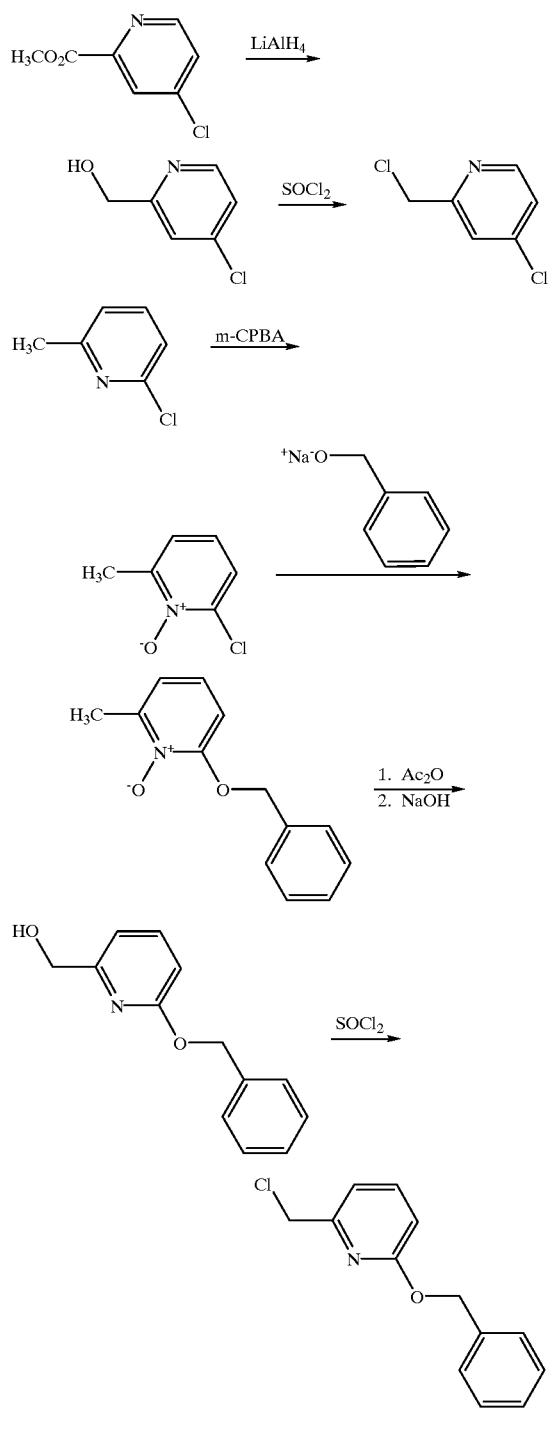
SCHEME 33
62
-continued
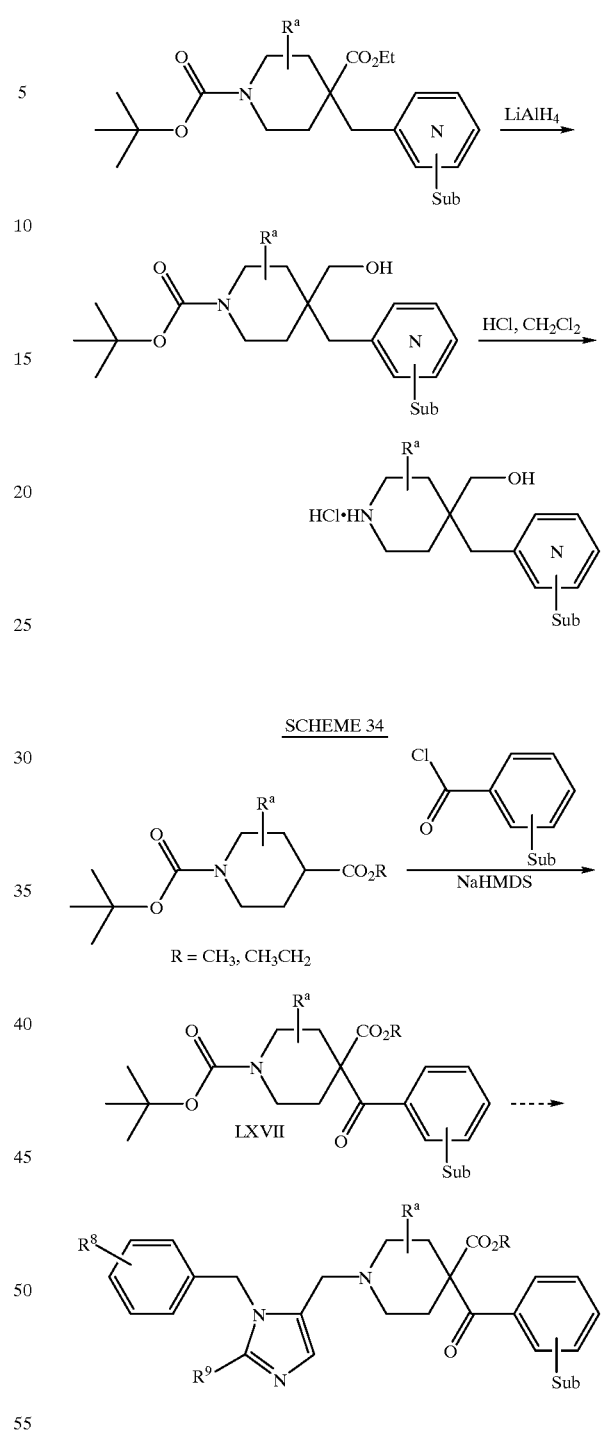
SCHEME 34
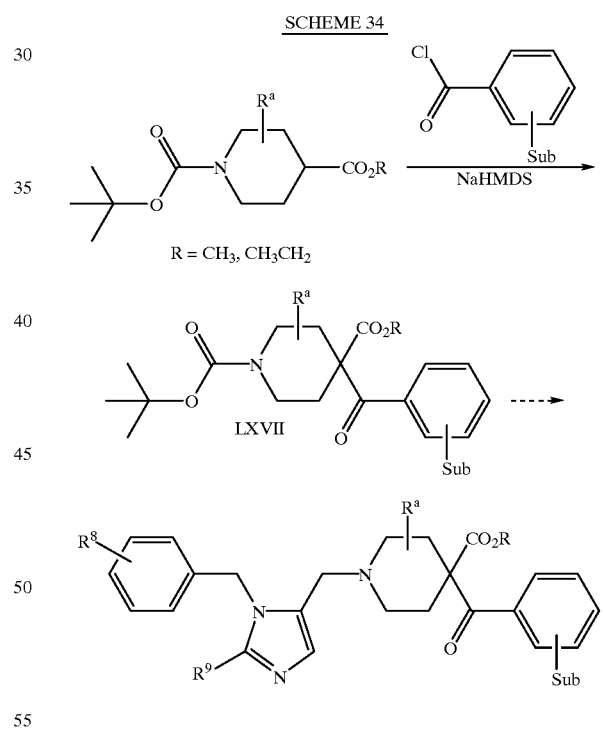
SCHEME 35
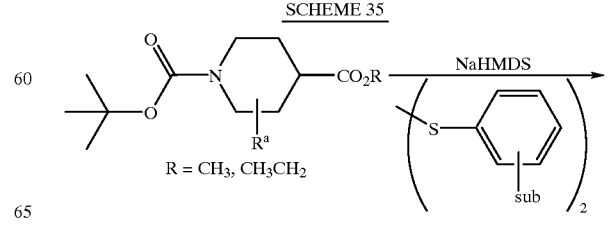
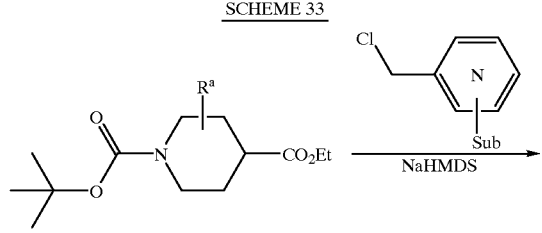

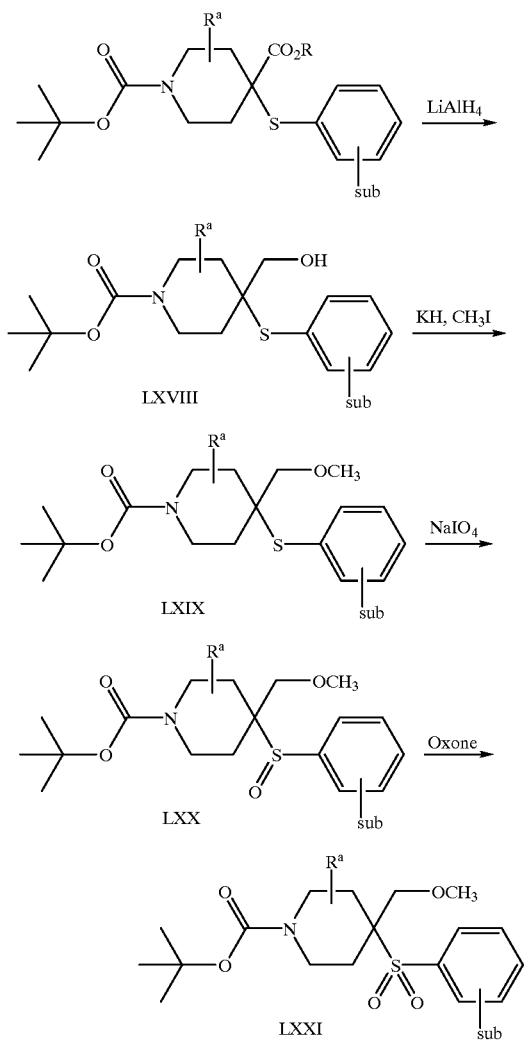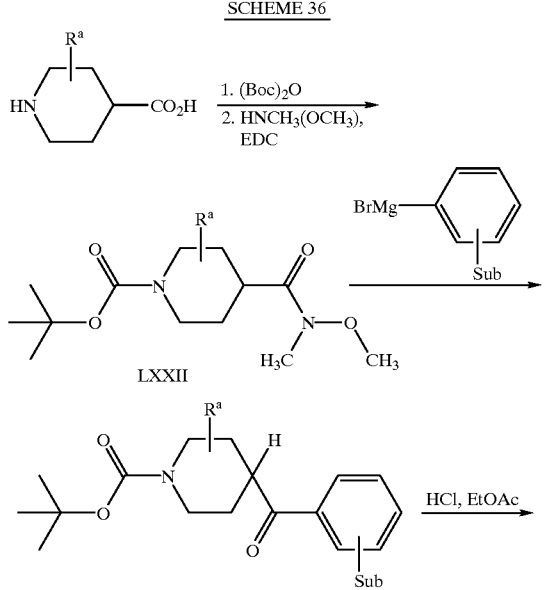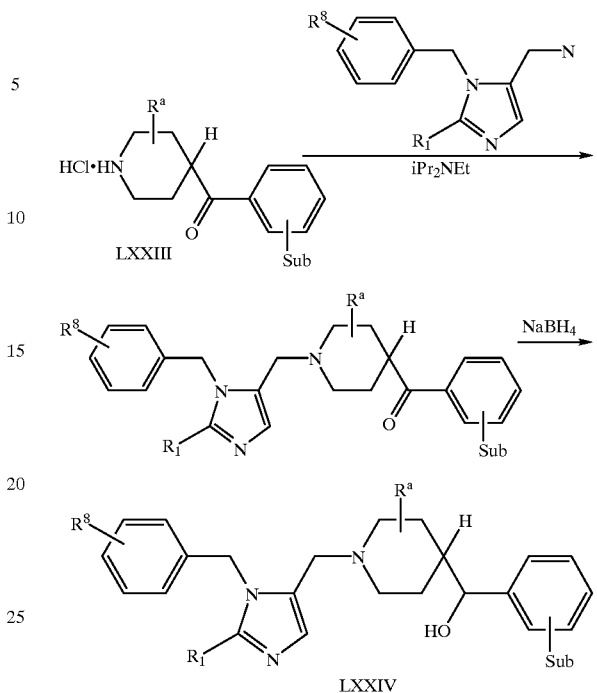

-continued

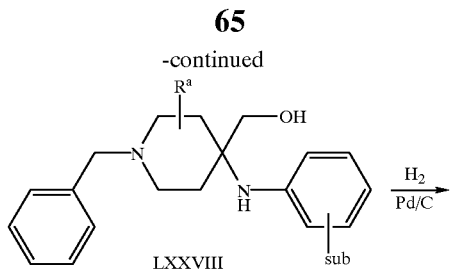

LXXVIII

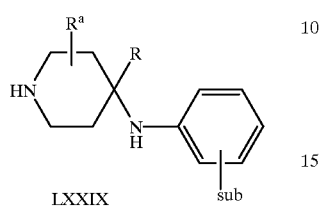

LXXIX

Compounds of this invention of formula (III) are prepared by employing the reactions shown in the following Reaction Schemes 38–51, in addition to other standard manipulations such as ester hydrolysis, cleavage of protecting groups, etc., as may be known in the literature or exemplified in the experimental procedures. Some key bond-forming and peptide modifying reactions are:

Reaction A Amide bond formation and protecting group cleavage using standard solution or solid phase methodologies.

Reaction B Preparation of a reduced peptide subunit by reductive alkylation of an amine by an aldehyde using sodium cyanoborohydride or other reducing agents.

Reaction C Alkylation of a reduced peptide subunit with an alkyl or aralkyl halide or, alternatively, reductive alkylation of a reduced peptide subunit with an aldehyde using sodium cyanoborohydride or other reducing agents.

Reaction D Peptide bond formation and protecting group cleavage using standard solution or solid phase methodologies.

Reaction E Preparation of a reduced subunit by borane reduction of the amide moiety.

These reactions may be employed in a linear sequence to provide the compounds of the invention or they may be used to synthesize fragments which are subsequently joined by the alkylation reactions described in the Reaction Schemes and in Reaction Schemes 43–51 hereinbelow.

REACTION SCHEME 38
Reaction A. Coupling of residues to form an amide bond

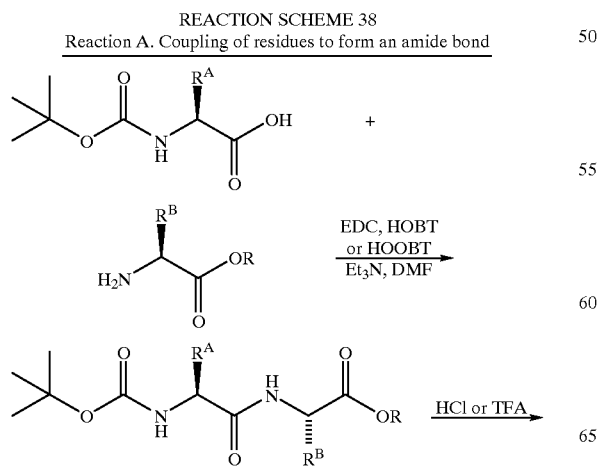

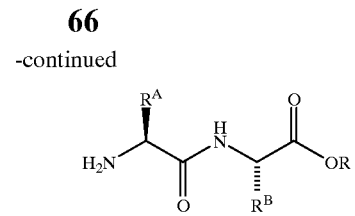

REACTION SCHEME 39
Reaction B. Preparation of reduced peptide subunits by reductive alkylation

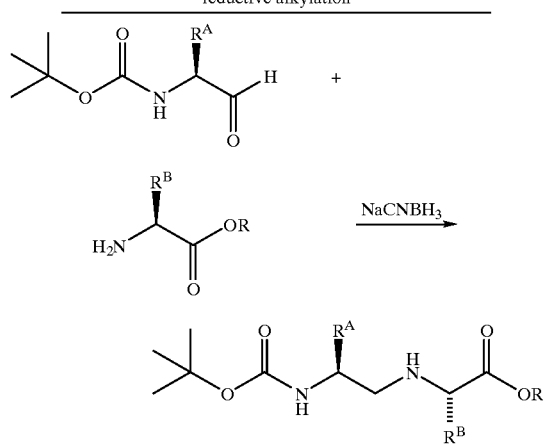

REACTION SCHEME 40
Reaction C. Alkylation/reductive alkylation of reduced peptide subunits

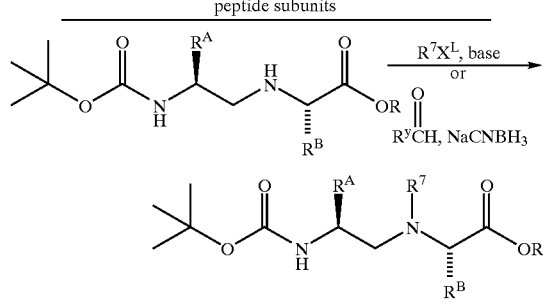

REACTION SCHEME 41
Reaction D. Coupling of residues to form an amide bond

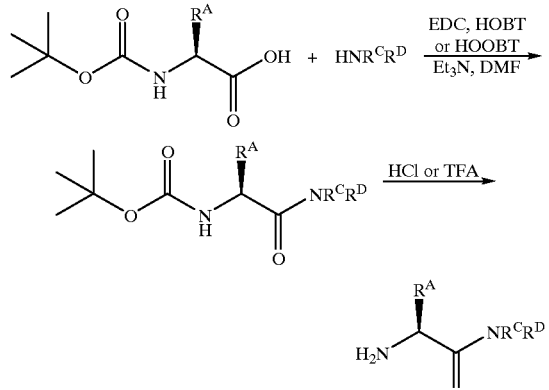

REACTION SCHEME 42
Reaction E. Preparation of reduced dipeptides from peptides

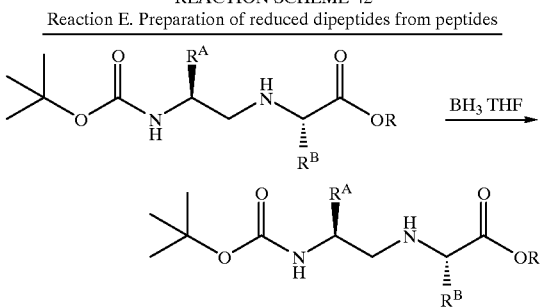

Where $R^A$ and $R^B$ are $R^2$, $R^3$ or $R^5$ as previously defined; $R^C$ and $R^D$ are $R^7$ or $R^{12}$; $X^L$ is a leaving group, e.g., Br—, I— or MsO—; and RY is defined such that $R^7$ is generated by the reductive alkylation process.

In addition to the reactions described in Reaction Schemes 26–30, other reactions used to generate the compounds of formula (III) of this invention are shown in the Reaction Schemes 43–51. All of the substituents shown in the Reaction Schemes, represent the same substituents as defined hereinabove. The substituent "Ar" in the Reaction Schemes represents a carbocyclic or heterocyclic, substituted or unsubstituted aromatic ring.

These reactions may be employed in a linear sequence to provide the compounds of the invention or they may be used to synthesize fragments which are subsequently joined by the alkylation reactions described in the Reaction Schemes. The sequential order whereby substituents are incorporated into the compounds is often not critical and thus the order of reactions described in the Reaction Schemes are illustrative only and are not limiting.

Synopsis of Reaction Schemes 43–51:

The requisite intermediates are in some cases commercially available, or can be readily prepared according to known literature procedures, including those described in Reaction Schemes 38–42 hereinabove.

Reaction Scheme 43 illustrates incorporation of the cyclic amine moiety, such as a reduced prolyl moiety, into the compounds of the formula III of the instant invention. Reduction of the azide LXXXI provides the amine LXXXII, which may be mono- or di-substituted using techniques described above. As an example, incorporation of a naphthylmethyl group and an acetyl group is illustrated.

As shown in Reaction Scheme 44, direct attachment of a aromatic ring to a substituted amine such as LXXXIII is accomplished by coupling with a triarylbismuth reagent, such as tris(3-chlorophenyl) bismuth.

Reaction Scheme 45 illustrates the use of protecting groups to prepare compounds of the instant invention wherein the cyclic amine contains an alkoxy moiety. The hydroxy moiety of key intermediate LXXXIVa may be further converted to a fluoro or phenoxy moiety, as shown in Reaction Scheme 46. Intermediates LXXXV and LXXXVI may then be further elaborated to provide the instant compounds.

Reaction Scheme 474 illustrates syntheses of instant compounds wherein the variable $-(CR^4{}_2)_qA^3(CR^5{}_2)_nR^6$ is a suitably substituted $\alpha$-hydroxybenzyl moiety. Thus the protected intermediate aldehyde is treated with a suitably substituted phenyl Grignard reagent to provide the enantiomeric mixture LXXXVII. Treatment of the mixture with 2-picolinyl chloride allows chromatographic resolution of compounds LXXXVIII and IXC. Removal of the picolinoyl group followed by deprotection provides the optically pure intermediate XC which can be further processed as described hereinabove to yield the instant compounds.

Syntheses of imidazole-containing intermediates useful in synthesis of instant compounds wherein the variable p is 0 or 1 and Z is $H_2$ are shown in Reaction Scheme 48 and 49. Thus the mesylate XCI can be utilized to alkylate a suitably substituted amine or cyclic amine, while aldehyde XCII can be used to similarly reductively alkylate such an amine.

Reaction Scheme 50 illustrates the syntheses of imidazole-containing intermediates wherein the attachment point of the $-(CR^2{}_2)_p-C(Z)-$ moiety to W (imidazolyl) is through an imidazole ring nitrogen. Reaction Scheme 51 illustrates the synthesis of an intermediate wherein an $R^2$ substituent is a methyl.

REACTION SCHEME 43

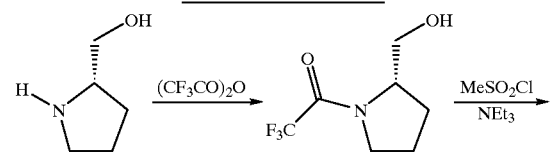

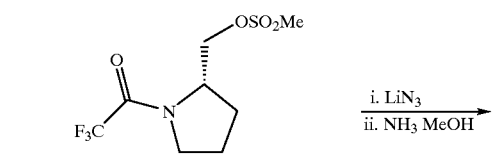

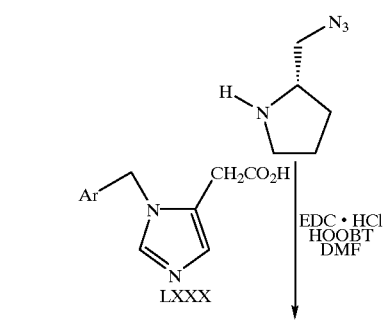

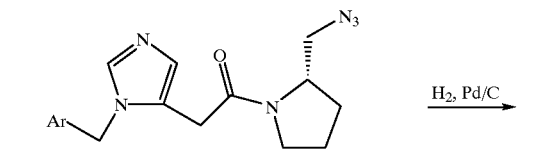

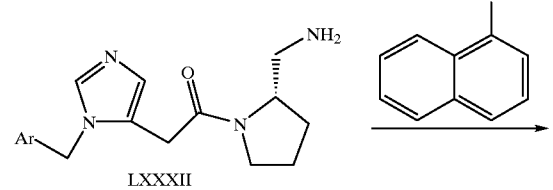

6,103,487
69
-continued
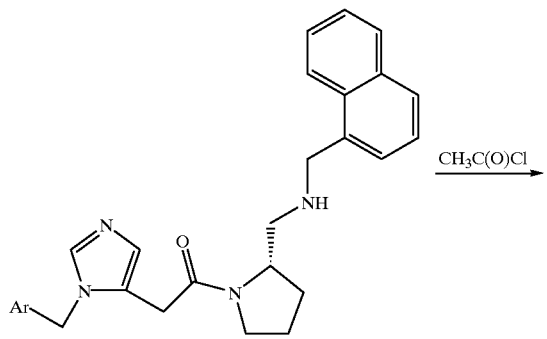
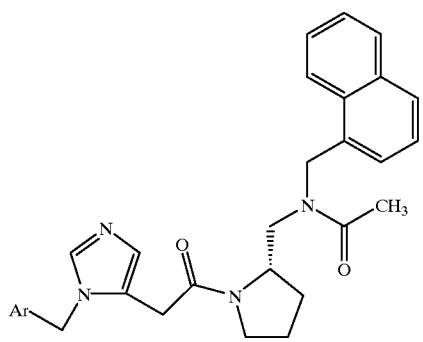
REACTION SCHEME 44
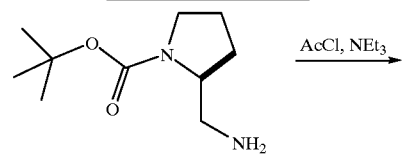
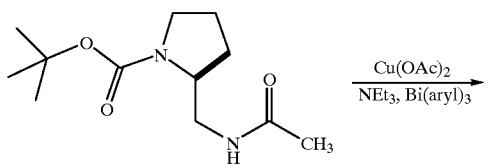
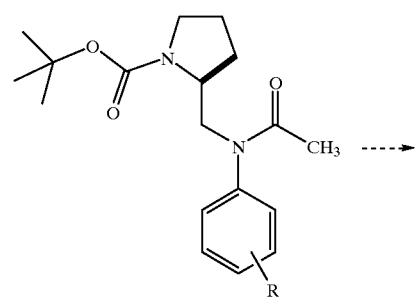
70
-continued
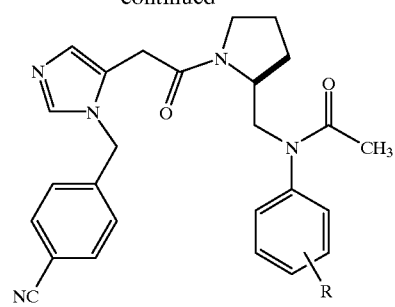
REACTION SCHEME 45
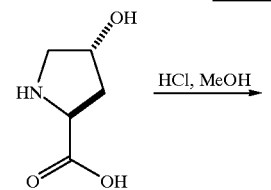
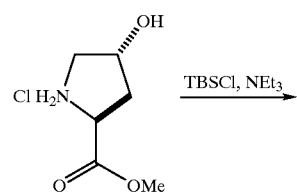
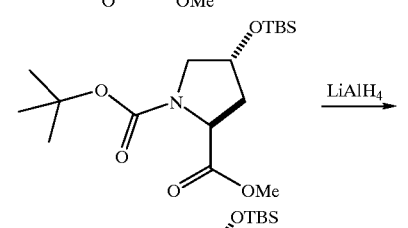
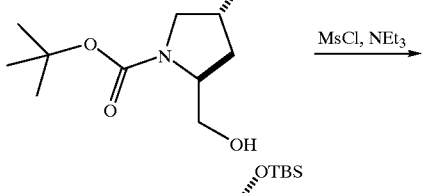
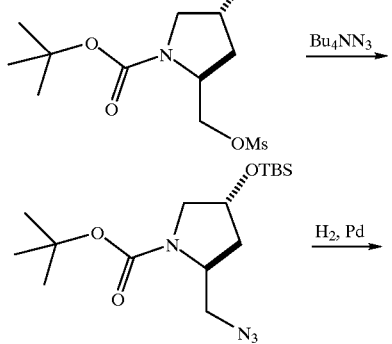

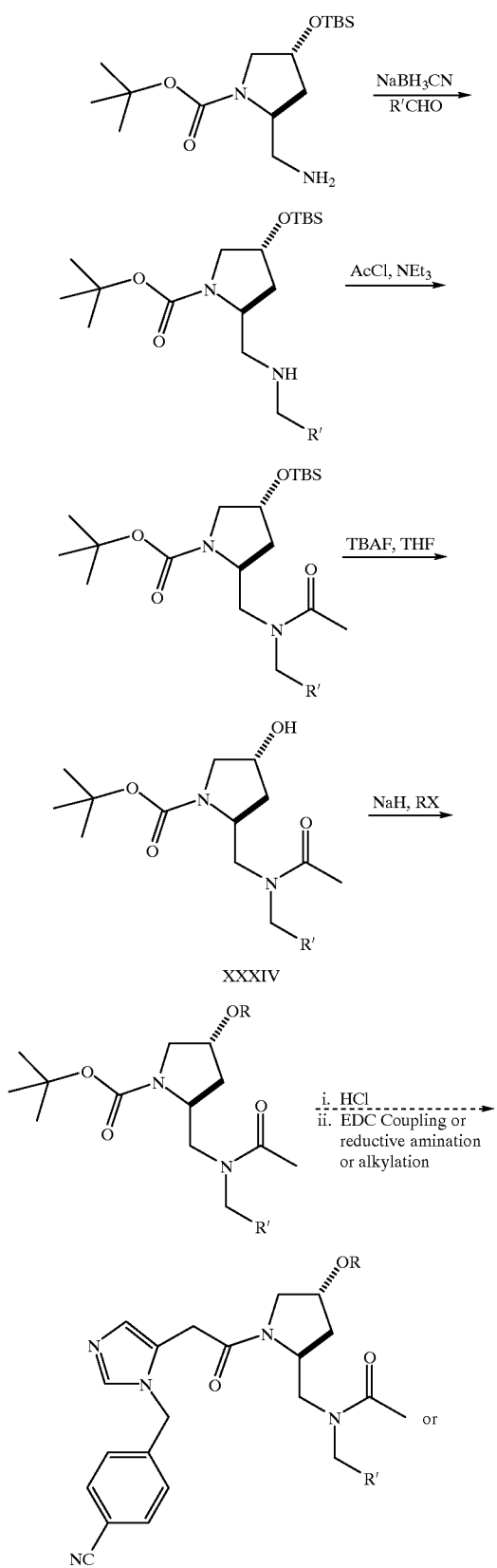
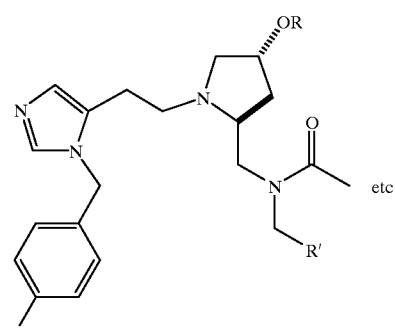
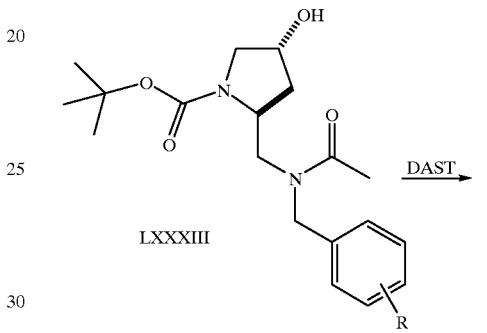
REACTION SCHEME 46
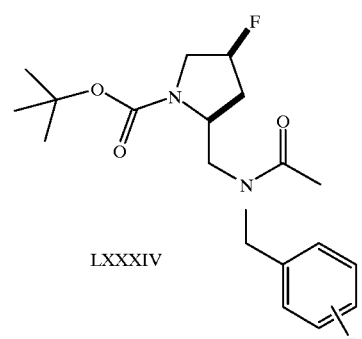
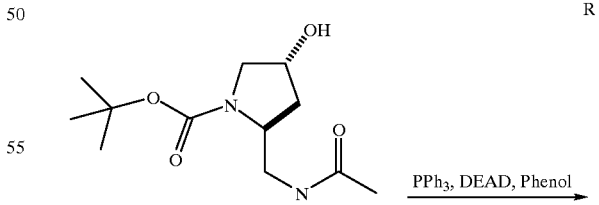

73
-continued
LXXXIII
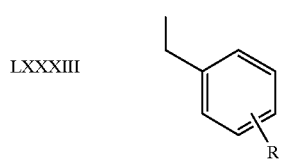
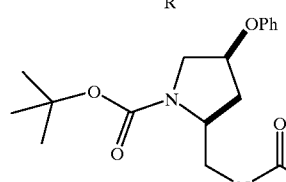
LXXXV
REACTION SCHEME 47
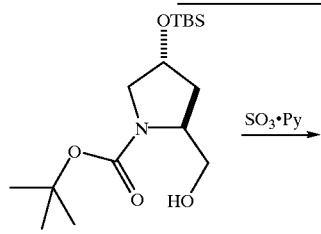
SO₃·Py →
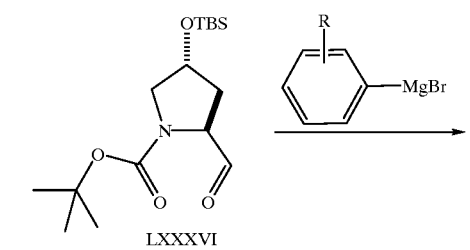
LXXXVI
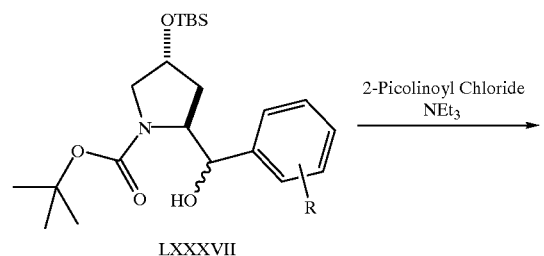
LXXXVII
2-Picolinoyl Chloride
NEt₃ →
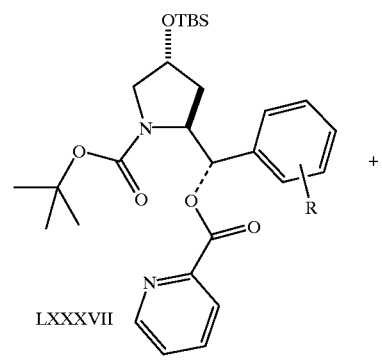
+
LXXXVII
74
-continued
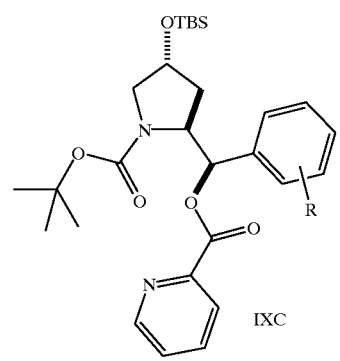
IXC
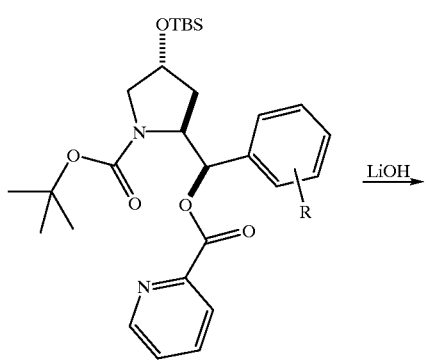
LiOH →
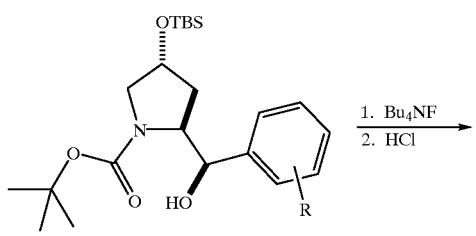
1. Bu₄NF
2. HCl →
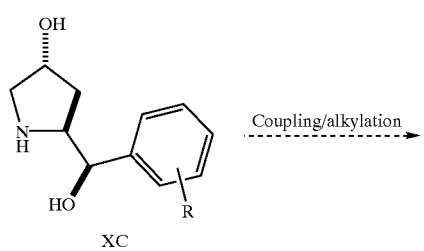
XC
Coupling/alkylation ⇢
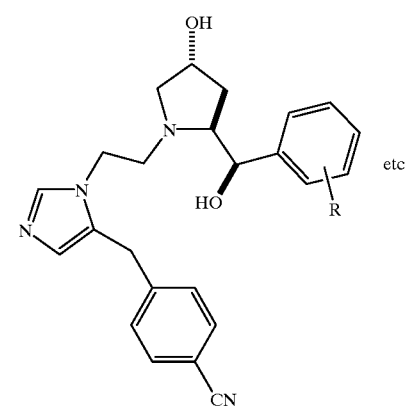
etc

REACTION SCHEME 48

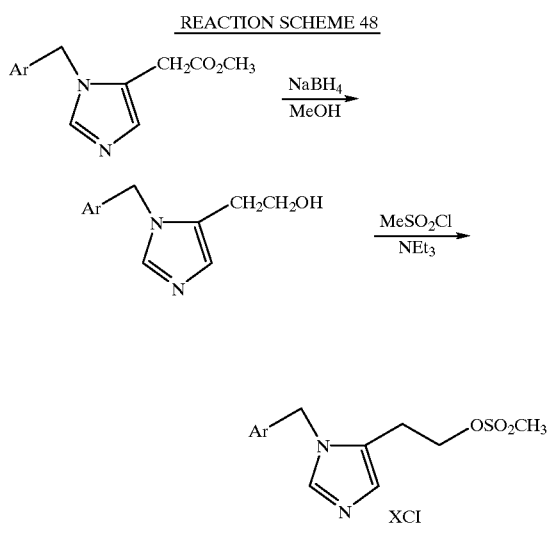

REACTION SCHEME 49

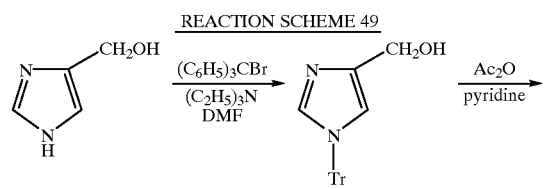

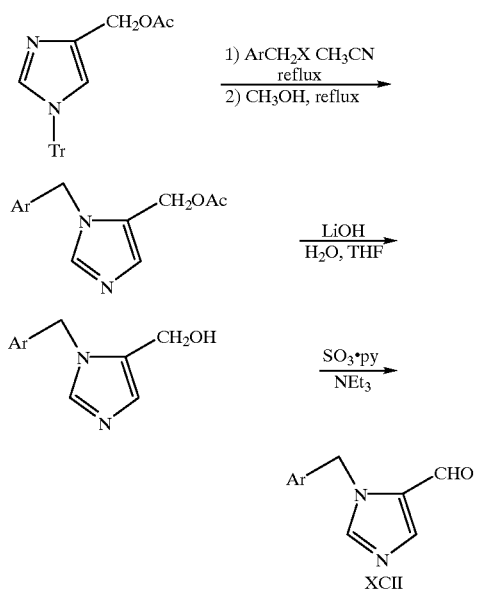

REACTION SCHEME 50

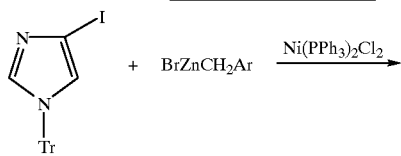

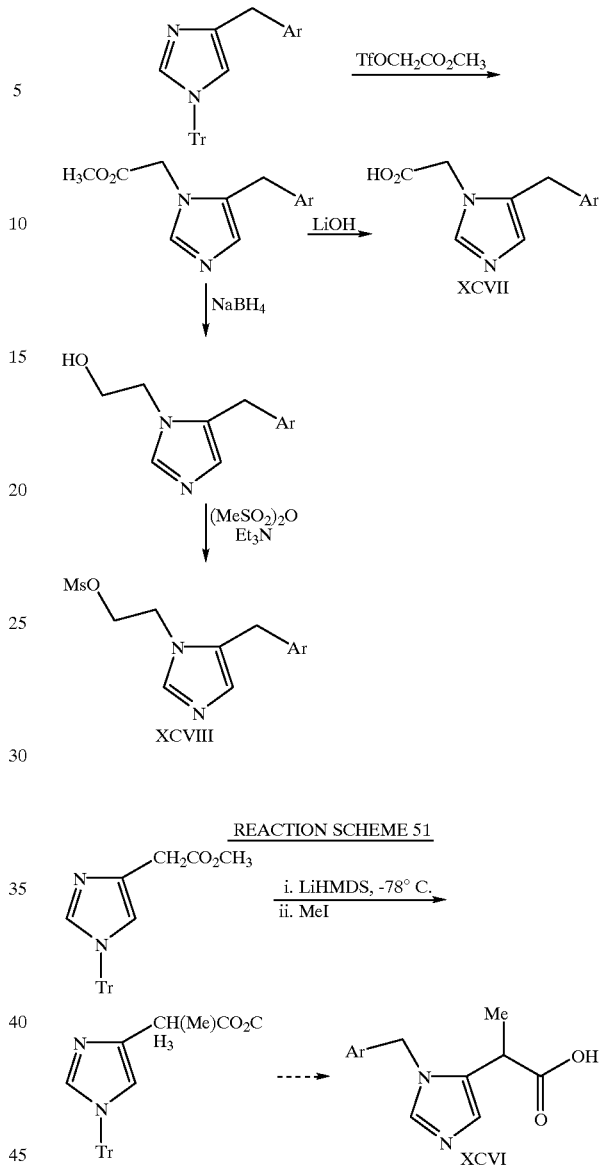

The prenyl transferase inhibitors of formula (A) can be synthesized in accordance with Reaction Scheme below, in addition to other standard manipulations such as ester hydrolysis, cleavage of protecting groups, etc., as may be known in the literature or exemplified in the experimental procedures. Some key reactions utilized to form the amino-diphenyl moiety of the instant compounds are shown.

The reactions may be employed in a linear sequence to provide the compounds of the invention or they may be used to synthesize fragments which are subsequently joined by the alkylation reactions described in the Reaction Scheme.

A method of forming the benzophenone intermediates, illustrated in Reaction Scheme 52, is a Stille reaction with an aryl stannane. Such amine intermediates may then be reacted as illustrated hereinabove with a variety of aldehydes and esters/acids.

REACTION SCHEME 52

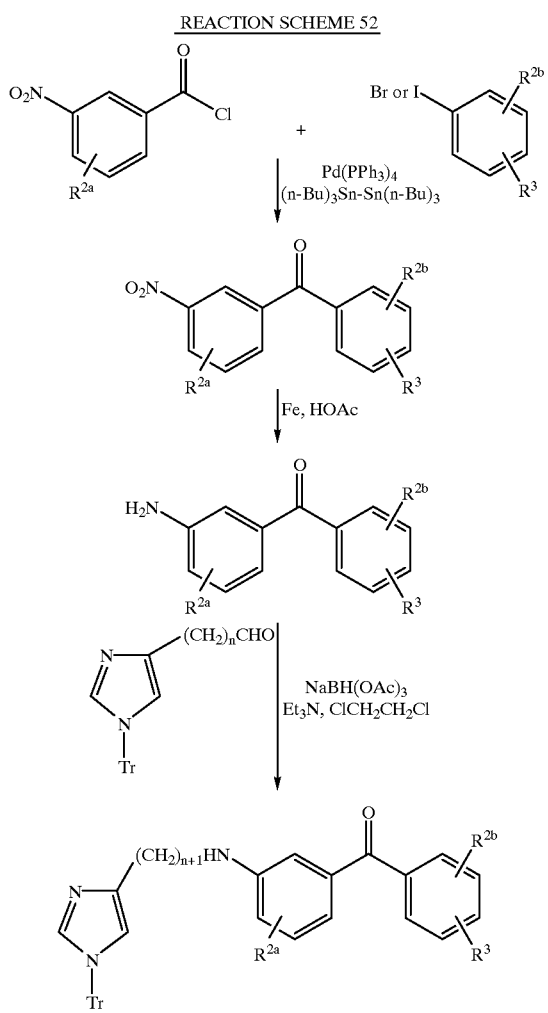

EXAMPLES

Examples provided are intended to assist in a further understanding of the invention. Particular materials employed, species and conditions are intended to be further illustrative of the invention and not limitative of the reasonable scope thereof.

The standard workup referred to in the examples refers to solvent extraction and washing the organic solution with 10% citric acid, 10% sodium bicarbonate and brine as appropriate. Solutions were dried over sodium sulfate and evaporated in vacuo on a rotary evaporator.

Example 1

1-(3-Chlorophenyl)-4-[1-(4-cyanobenzyl) imidazolylmethyl]-2-piperazinone dihydrochloride (Compound 1)

Step A: Preparation of 1-triphenylmethyl-4-(hydroxymethyl)-imidazole

To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: Preparation of 1-triphenylmethyl-4-(acetoxymethyl)-imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. $NaHCO_3$, and brine, then dried ($Na_2SO_4$), filtered, and concentrated in vacuo to provide the crude product. The acetate was isolated as a white powder which was sufficiently pure for use in the next reaction.

Step C: Preparation of 1-(4-cyanobenzyl)-5-(acetoxymethyl)-imidazole hydrobromide A solution of the product from Step B (85.8 g, 225 mmol) and α-bromo-p-tolunitrile (50.1 g, 232 mmol) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step D: Preparation of 1-(4-cyanobenzyl)-5-(hydroxymethyl)-imidazole

To a solution of the acetate from Step C (50.4 g, 150 mmol) in 1.5 L of 3:1 THF/water at 0° C. was added lithium hydroxide monohydrate (18.9 g, 450 mmol). After one hour, the reaction was concentrated in vacuo, diluted with EtOAc (3 L), and washed with water, sat. aq. $NaHCO_3$ and brine. The solution was then dried ($Na_2SO_4$), filtered, and concentrated in vacuo to provide the crude product as a pale yellow fluffy solid which was sufficiently pure for use in the next step without further purification.

Step E: Preparation of 1-(4-cyanobenzyl)-5-imidazolecarboxaldehyde

To a solution of the alcohol from Step D (21.5 g, 101 mmol) in 500 mL of DMSO at room temperature was added triethylamine (56 mL, 402 mmol), then $SO_3$-pyridine complex (40.5 g, 254 mmol). After 45 minutes, the reaction was poured into 2.5 L of EtOAc, washed with water (4×1 L) and brine, dried ($Na_2SO_4$), filtered, and concentrated in vacuo to provide the aldehyde as a white powder which was sufficiently pure for use in the next step without further purification.

Step F: Preparation of N-(3-chlorophenyl)ethylenediamine hydrochloride

To a solution of 3-chloroaniline (30.0 mL, 284 mmol) in 500 mL of dichloromethane at 0° C. was added dropwise a solution of 4 N HCl in 1,4-dioxane (80 mL, 320 mmol HCl). The solution was warmed to room temperature, then concentrated to dryness in vacuo to provide a white powder. A mixture of this powder with 2-oxazolidinone (24.6 g, 282 mmol) was heated under nitrogen atmosphere at 160° C. for 10 hours, during which the solids melted, and gas evolution was observed. The reaction was allowed to cool, forming the crude diamine hydrochloride salt as a pale brown solid.

Step G: Preparation of N-(tert-butoxycarbonyl)-N'-(3-chlorophenyl)ethylenediamine The amine hydrochloride from Step F (ca. 282 mmol, crude material prepared above) was taken up in 500 mL of THF and 500 mL of sat. aq. $NaHCO_3$ soln., cooled to 0° C., and di-tert-butylpyrocarbonate (61.6 g, 282 mmol) was added. After 30 h, the reaction was poured into EtOAc, washed with water and brine, dried ($Na_2SO_4$), filtered, and concentrated in vacuo to provide the titled carbamate as a brown oil which was used in the next step without further purification.

Step H: Preparation of N-[2-(tert-butoxycarbamoyl)ethyl]-N-(3-chlorophenyl)-2-chloroacetamide A solution of the product from Step G (77 g, ca. 282 mmol) and triethylamine (67 mL, 480 mmol) in 500 mL of $CH_2Cl_2$ was cooled to 0° C. Chloroacetyl chloride (25.5 mL, 320 mmol) was added dropwise, and the reaction was maintained at 0° C. with stirring. After 3 h, another portion of chloroacetyl chloride (3.0 mL) was added dropwise. After 30 min, the reaction was poured into EtOAc (2 L) and washed with water, sat. aq. $NH_4Cl$ soln, sat. aq. $NaHCO_3$ soln., and brine. The solution was dried ($Na_2SO_4$), filtered, and concentrated in vacuo to provide the chloroacetamide as a brown oil which was used in the next step without further purification.

Step I: Preparation of 4-(tert-butoxycarbonyl)-1-(3-chlorophenyl)-2-piperazinone To a solution of the chloroacetamide from Step H (ca. 282 mmol) in 700 mL of dry DMF was added $K_2CO_3$ (88 g, 0.64 mol). The solution was heated in an oil bath at 70–75° C. for 20 hrs., cooled to room temperature, and concentrated in vacuo to remove ca. 500 mL of DMF. The remaining material was poured into 33% EtOAc/hexane, washed with water and brine, dried ($Na_2SO_4$), filtered, and concentrated in vacuo to provide the product as a brown oil. This material was purified by silica gel chromatography (25–50% EtOAc/hexane) to yield pure product, along with a sample of product (ca. 65% pure by HPLC) containing a less polar impurity.

Step J: Preparation of 1-(3-chlorophenyl)-2-piperazinone

Through a solution of Boc-protected piperazinone from Step I (17.19 g, 55.4 mmol) in 500 mL of EtOAc at -78° C. was bubbled anhydrous HCl gas. The saturated solution was warmed to 0° C., and stirred for 12 hours. Nitrogen gas was bubbled through the reaction to remove excess HCl, and the mixture was warmed to room temperature. The solution was concentrated in vacuo to provide the hydrochloride as a white powder. This material was taken up in 300 mL of $CH_2Cl_2$ and treated with dilute aqueous $NaHCO_3$ solution. The aqueous phase was extracted with $CH_2Cl_2$ (8×300 mL) until tlc analysis indicated complete extraction. The combined organic mixture was dried ($Na_2SO_4$), filtered, and concentrated in vacuo to provide the titled free amine as a pale brown oil.

Step K: Preparation of 1-(3-chlorophenyl)-4-[1-(4-cyanobenzyl)imidazolylmethyl]-2-piperazinone dihydrochloride To a solution of the amine from Step J (55.4 mmol, prepared above) in 200 mL of 1,2-dichloroethane at 0° C. was added 4 Å powdered molecular sieves (10 g), followed by sodium triacetoxyborohydride (17.7 g, 83.3 mmol). The imidazole carboxaldehyde from Step E of Example 1 (11.9 g, 56.4 mmol) was added, and the reaction was stirred at 0° C. After 26 hours, the reaction was poured into EtOAc, washed with dilute aq. $NaHCO_3$, and the aqueous layer was back-extracted with EtOAc. The combined organics were washed with brine, dried ($Na_2SO_4$), filtered, and concentrated in vacuo. The resulting product was taken up in 500 mL of 5:1 benzene:$CH_2Cl_2$, and propylamine (20 mL) was added. The mixture was stirred for 12 hours, then concentrated in vacuo to afford a pale yellow foam. This material was purified by silica gel chromatography (2–7% MeOH/$CH_2Cl_2$), and the resultant white foam was taken up in $CH_2Cl_2$ and treated with 2.1 equivalents of 1 M HCl/ether solution. After concentrated in vacuo, the product dihydrochloride was isolated as a white powder.

Examples 2–5 (Table 1) were prepared using the above protocol, which describes the synthesis of the structurally related compound 1-(3-chlorophenyl)-4-[1-(4-cyanobenzyl)-imidazolylmethyl]-2-piperazinone dihydrochloride. In Step F, the appropriately substituted aniline was used in place of 3-chloroaniline.

TABLE 1

1-Aryl-4-[1-(4-cyanobenzyl)imidazolylmethyl]-2-piperazinones

| Example | X | FAB mass spectrum (M + 1) | CHN Analysis |
|---|---|---|---|
| 2 | 3-OCF$_3$ | 456 | C$_{23}$H$_{20}$F$_3$N$_5$O$_2$.2.0HCl.0.60H$_2$O calcd; C, 51.24; H, 4.34; N, 12.99. found; C, 51.31; H, 4.33; N, 12.94. |
| 3 | 2,5-(CH$_3$)$_2$ | 400 | C$_{24}$H$_{25}$N$_5$O.2.00HCl.0.65H$_2$O calcd; C, 59.54; H, 5.89; N, 14.47 found; C, 59.54; H, 5.95; N, 14.12. |
| 4 | 3-CH$_3$ | 386 | C$_{23}$H$_{23}$N$_5$O.2.0HCl.0.80H$_2$O calcd; C, 58.43; H, 5.67; N, 14.81. found; C, 58.67; H, 6.00; N, 14.23. |
| 5 | 3-I | 498 | C$_{22}$H$_{20}$N$_5$OI.2.25HCl.0.90H$_2$O calcd; C, 44.36; H, 4.07; N, 11.76. found; C, 44.37; H, 4.06; N, 11.42. |

Example 6

1-(3-chlorophenyl)-4-[1-(4-cyano-3-methoxybenzyl) imidazolylmethyl]-2-piperazinone dihydrochloride Step A: Preparation of Methyl 4-Amino-3-hydroxybenzoate Through a solution of 4-amino-3-hydroxybenzoic acid (75 g, 0.49 mol) in 2.0 L of dry methanol at room temperature was bubbled anhydrous HCl gas until the solution was saturated. The solution was stirred for 48 hours, then concentrated in vacuo. The product was partitioned between EtOAc and saturated aq. $NaHCO_3$ solution, and the organic layer was washed with brine, dried ($Na_2SO_4$), and concentrated in vacuo to provide the titled compound (79 g, 96% yield).

Step B: Preparation of Methyl 3-Hydroxy-4-iodobenzoate

A cloudy, dark solution of the product from Step A (79 g, 0.47 mol), 3N HCl (750 mL), and THF (250 mL) was cooled to 0° C. A solution of $NaNO_2$ (35.9 g, 0.52 mol) in 115 mL of water was added over ca. 5 minutes, and the solution was stirred for another 25 minutes. A solution of potassium iodide (312 g, 1.88 mol) in 235 mL of water was added all at once, and the reaction was stirred for an additional 15 minutes. The mixture was poured into EtOAc, shaken, and the layers were separated. The organic phase was washed with water and brine, dried ($Na_2SO_4$), and concentrated in vacuo to provide the crude product (148 g). Purification by column chromatography through silica gel (0%–50% EtOAc/hexane) provided the titled product (96 g, 73% yield).

Step C: Preparation of Methyl 4-Cyano-3-hydroxybenzoate

A mixture of the iodide product from Step B (101 g, 0.36 mol) and zinc(II)cyanide (30 g, 0.25 mol) in 400 mL of dry DMF was degassed by bubbling argon through the solution for 20 minutes. Tetrakis(triphenylphosphine)palladium (8.5 g, 7.2 mmol) was added, and the solution was heated to 80° C. for 4 hours. The solution was cooled to room temperature, then stirred for an additional 36 hours. The reaction was poured into EtOAc/water, and the organic layer was washed with brine (4x), dried ($Na_2SO_4$), and concentrated in vacuo to provide the crude product. Purification by column chromatography through silica gel (30%–50% EtOAc/hexane) provided the titled product (48.8 g, 76% yield).

Step D: Preparation of Methyl 4-Cyano-3-methoxybenzoate

Sodium hydride (9 g, 0.24 mol as 60% wt. disp. mineral oil) was added to a solution of the phenol from Step C (36.1 g, 204 mmol) in 400 mL of dry DMF at room temperature. Iodomethane was added (14 mL. 0.22 mol) was added, and the reaction was stirred for 2 hours. The mixture was poured into EtOAc/water, and the organic layer was washed with water and brine (4x), dried ($Na_2SO_4$), and concentrated in vacuo to provide the titled product (37.6 g, 96% yield).

Step E: Preparation of 4-Cyano-3-methoxybenzyl Alcohol

To a solution of the ester from Step D (48.8 g, 255 mmol) in 400 mL of dry THF under argon at room temperature was added lithium borohydride (255 mL, 510 mmol, 2M THF) over 5 minutes. After 1.5 hours, the reaction was warmed to reflux for 0.5 hours, then cooled to room temperature. The solution was poured into EtOAc/1N HCl soln. [CAUTION], and the layers were separated. The organic layer was washed with water, sat $Na_2CO_3$ soln. and brine (4x), dried ($Na_2SO_4$), and concentrated in vacuo to provide the titled product (36.3 g, 87% yield).

Step F: Preparation of 4-Cyano-3-methoxybenzyl Bromide

A solution of the alcohol from Step E (35.5 g, 218 mmol) in 500 mL of dry THF was cooled to 0° C. Triphenylphosphine was added (85.7 g, 327 mmol), followed by carbontetrabromide (108.5 g, 327 mmol). The reaction was stirred at 0° C. for 30 minutes, then at room temperature for 21 hours. Silica gel was added (ca. 300 g), and the suspension was concentrated in vacuo. The resulting solid was loaded onto a silica gel chromatography column. Purification by flash chromatography (30%–50% EtOAc/hexane) provided the titled product (42 g, 85% yield).

Step G: Preparation of 1-(4-cyano-3-methoxybenzyl)-5-(acetoxymethyl)-imidazole hydrobromide The titled product was prepared by reacting the bromide from Step F (21.7 g, 96 mmol) with the imidazole product from Step B of Example 1 (34.9 g, 91 mmol) using the procedure outlined in Step C of Example 1. The crude product was triturated with hexane to provide the titled product hydrobromide (19.43 g, 88% yield).

Step H: Preparation of 1-(4-cyano-3-methoxybenzyl)-5-(hydroxymethyl)-imidazole

The titled product was prepared by hydrolysis of the acetate from Step G (19.43 g, 68.1 mmol) using the procedure outlined in Step D of Example 1. The crude titled product was isolated in modest yield (11 g, 66% yield). Concentration of the aqueous extracts provided solid material (ca. 100 g) which contained a significant quantity of the titled product, as judged by $^1H$ NMR spectroscopy.

Step I: Preparation of 1-(4-cyano-3-methoxybenzyl)-5-imidazolecarboxaldehyde

The titled product was prepared by oxidizing the alcohol from Step H (11 g, 45 mmol) using the procedure outlined in Step E of Example 1. The titled aldehyde was isolated as a white powder (7.4 g, 68% yield) which was sufficiently pure for use in the next step without further purification.

Step J: Preparation of 1-(3-chlorophenyl)-4-[1-(4-cyano-3-methoxybenzyl)imidazolylmethyl]-2-piperazinone dihydrochloride The titled product was prepared by reductive alkylation of the aldehyde from Step I (859 mg, 3.56 mmol) and the amine (hydrochloride) from Step K of Example 1 (800 mg, 3.24 mmol) using the procedure outlined in Step H of Example 1. Purification by flash column chromatography through silica gel (50%–75% acetone $CH_2Cl_2$) and conversion of the resulting white foam to its dihydrochloride salt provided the titled product as a white powder (743 mg, 45% yield). FAB ms (m+1) 437.

Anal. Calc. for $C_{23}H_{23}ClN_5O_{2.2}.0HCl.0.35CH_2Cl_2$: C, 51.97; H, 4.80; N, 12.98. Found: C, 52.11; H, 4.80; N, 12.21.

Example 7

1-(3-trifluoromethoxyphenyl)-4-[1-(4-cyano-3-methoxybenzyl)imidazolyl methyl]-2-piperazinone dihydrochloride 1-(3-trifluoromethoxy-phenyl)-2-piperazinone hydrochloride was prepared from 3-trifluoromethoxyaniline using Steps F–J of Example 1. This amine (1.75 g, 5.93 mmol) was coupled to the aldehyde from Step I of Example 6 (1.57 g, 6.52 mmol) using the procedure outlined in Step H of Example 1. Purification by flash column chromatography through silica gel (60%–100% acetone $CH_2Cl_2$) and conversion of the resulting white foam to its dihydrochloride salt provided the titled product as a white powder (1.947 g, 59% yield). FAB ms (m+1) 486.

Anal. Calc. for $C_{24}H_{23}F3N_5O_{3.2.0}HCl.0.60H_2O$: C, 50.64; H, 4.46; N, 12.30. Found: C, 50.69; H, 4.52; N, 12.13.

Example 8

4-[((1-(4-cyanobenzyl)-5-imidazolyl)methyl)amino] benzophenone hydrochloride

The titled product was prepared by reductive alkylation of the aldehyde from Step E of Example 1 (124 mg, 0.588 mmol) and 4-aminobenzophenone (116 mg, 0.588 mmol) using the procedure outlined in Step K of Example 1. Purification by flash column chromatography through silica gel (2–6% MeOH/$CH_2Cl_2$) and conversion to the hydrochloride salt provided the titled product as a white solid (126 mg, 50% yield). FAB ms (m+1) 393.11.

Anal. Calc. for $C_{25}H_{20}N_5O.1.40HCl0.40H_2O$: C, 66.62; H, 4.96; N, 12.43. Found: C, 66.73; H, 4.94; N, 12.46.

Example 9

N-{1-(4-Cyanobenzyl)-1H-imidazol-5-ylethyl}-4(R)-benzyloxy-2(S)-{N'-acetyl-N'-3-chlorobenzyl}aminomethylpyrolidine Step A: 4(R)-Hydroxyproline methyl ester A suspension of 4(R)-hydroxyproline (35.12 g, 267.8 mmol) in methanol (500 ml) was saturated with gaseous hydrochloric acid. The resulting solution was allowed to stand for 16 hrs and the solvent evaporated in vacuo to afford the title compound as a white solid.

$^1$H NMR CD$_3$OD δ4.60 (2H, m), 3.86(3H, s), 3.48(1H, dd, J=3.6 and 12.0 Hz), 3.23(1H, d, J=12.0 Hz), 2.43(1H, m) and 2.21(1H, m) ppm.

Step B: N-t-Butoxycarbonyl-4(R)-hydroxyproline methyl ester

To a solution of 4(R)-hydroxyproline methyl ester (53.5 g, 268 mmol), and triethylamine (75 ml, 540 mmol), in CH$_2$Cl$_2$ (500 ml), at 0° C., was added a solution of di-t-butyl dicarbonate (58.48, 268 mmol), in CH$_2$Cl$_2$ (75 ml). The resulting mixture was stirred for 48 hrs at room temperature. The solution was washed with 10% aqueous citric acid solution, saturated NaHCO$_3$ solution, dried (Na$_2$SO$_4$) and the solvent evaporated in vacuo. The title compound was obtained as a yellow oil and used in the next step without further purification.

$^1$H NMR CD$_3$OD δ4.40–4.30 (2H, m), 3.75(3H, m), 3.60–3.40(2H, m), 2.30(1H, m), 2.05(1H, m) and 1.55–1.40 (9H, m) ppm.

Step C: N-t-Butoxycarbonyl-4(R)-t-butyldimethylsilyloxy proline methyl ester

To a solution of N-t-butoxycarbonyl-4(R)-hydroxy proline methyl ester (65.87 g, 268 mmol), and triethylamine (41 ml, 294 mmol), in CH$_2$Cl$_2$ (536 ml), at 0° C., was added a solution of t-butyldimethyl silylchloride (42.49 g, 282 mmol), in CH$_2$Cl$_2$ (86 ml). The resulting mixture was stirred for 16 hrs at room temperature. The solution was washed with 10% aqueous citric acid solution, saturated NaHCO$_3$ solution, dried (Na$_2$SO$_4$) and the solvent evaporated in vacuo. The title compound was obtained as a yellow oil and used in the next step without furthur purification.

$^1$H NMR CD$_3$OD δ4.60–4.40 (2H, m), 3.75(3H, m), 3.60–3.20(2H, n), 2.30–1.90(2H, m), 45–1.40(9H, m), 0.90–0.85(9H, m), 0.10–0.00(6H, m) ppm.

Step D: N-t-Butoxycarbonyl-4(R)-t-butyldimethylsilyloxy-2(S)-hydroxymethylpyrrolidine A solution of N-t-butoxycarbonyl-4-(R)-t-butyldimethylsilyloxy proline methyl ester (86.65 g, 241 mmol), in THF (150 ml), was added over 90 minutes to a solution of lithium aluminum hydride (247 ml of a 1 M solution in THF, 247 mmol), under argon, so that the temperature did not exceed 12° C. Stirring was continued for 50 mins and then EtOAc (500 ml) was added cautiously, followed by sodium sulphate decahydrate (34 g), and the resulting mixture stirred for 16 hrs at room temperature. Anhydrous Na$_2$SO$_4$ (34 g) was added and the mixture stirred an additional 30 min and then filtered. The solids were washed with EtOAc (800 ml), the filtrates combined and the solvent evaporated in vacuo. The title compound was obtained as a colourless oil and used in the next step without further purification.

Step D: N-t-Butoxycarbonyl-4(R)-t-butyldimethylsilyloxy-2(S)-methanesulfonyloxymethylpyrrolidine To a solution of N-t-butoxycarbonyl-4(R)-t-butyldimethylsilyloxy-2(S)-hydroxymethylpyrrolidine (50.0 g, 150.8 mmol) and triethylamine (42.0 ml, 300 mmol) in CH$_2$Cl$_2$(11) was added methane sulfonyl chloride (12.4 ml, 160 mmol) over a period of 5 minutes and stirring was continued for 1 hour. The solvent was evaporated in vacuo diluted with EtOAc (800 mL) and washed sequentially with aqueous citric acid and NaHCO$_3$. The organic extracts were dried (Na$_2$SO$_4$), evaporated in vacuo and the residue purified by chromatography (SiO$_2$, 15% EtOAc in hexanes). The title compound was obtained as a pale yellow solid FAB Mass spectrum, m/z=410(M+1).

$^1$H NMR CDCl$_3$δ4.60–4.00 (4H, m), 3.60–3.30(2H, m), 2.98(3H, s), 2.05–2.00(2H, m), 1.48–1.42(9H, m), 0.90–0.80(9H, ml), 0.10–0.00(6H, m) ppm.

Step F: Preparation of N-t-Butoxycarbonyl-4(R)-t-butyldimethylsilyloxy-2(S)-azidomethylpyrrolidine In a flask protected by a safety screen, a solution of N-t-butoxycarbonyl-4(S)-t-butyldimethylsilyloxy-2(S)-methane-sulfonyloxy methyl pyrrolidine(10.40 g, 25.39 mmol) and tetrabutyl-ammonium azide (8.18 g, 28.7 mmol) in toluene (250 mmol was stirred at 80° C. for 5 hr. The reaction was cooled to room temperature and diluted with EtOAc (250 mn), washed with water and brine and dried (Na$_2$SO$_4$). The solvent was evaporated in vacuo to afford the title compound as a yellow oil which was used in the next step without furthur purification.

$^1$H NMR CDCl$_3$δ4.60–3.20 (6H, m), 2.05–1.90(2H, m), 1.47(9H, s), 0.87(9H, s) and 0.10–0.00(6H, m) ppm.

Step G: Preparation of N-t-Butoxycarbonyl-4(R)-t-butyldimethylsilyloxy-2(S)-aminomethylpyrrolidine A solution of N-t-butoxycarbonyl-4(R)-t-butyldimethylsilyloxy-2(S )-azidomethylpyrrolidine (9.06 g, 25.39 mmol) in EtOAc (120 ml) was purged with argon and 10% palladium on carbon (1.05 g) added. The flask was evacuated and stirred under an atmosphere of hydrogen (49 psi) for 16 hrs. The hydrogen was replaced by argon, the catalyst removed by filtration and the solvent evaporated in vacuo. The residue was chromatographed (SiO$_2$, 2.5 to 5% saturated NH$_4$OH in acetonitrile gradient elution), to afford the title compound as an oil.

$^1$H NMR(CDCl$_3$, 400 MHz) δ4,40–2.60 (6H, s), 2.05–1.80(2H, m), 1.46)9H, s), 1.36(2H, s), 0.87)9H, s), 0.10–0.00(6H, m)ppm.

Step H: Preparation of N-t-Butoxycarbonyl-4(R)-t-butyldimethylsilyloxy-2(S)-{N'-3-chlorobenzyl}aminomethylpyrrolidine To a slurry of 3-chlorobenzaldehyde (1.2 ml, 10.6 mmol), crushed 3 A molecular sieves (9.5 g) and the amine from step G (3.50 g, 10.6 mmol) in methanol (150 ml) was added sodium cyanoborohydride (11.0 ml of a 1M solution in THF, 11.0 mmol) at room temperature. The pH was adjusted to 7 by the addition of glacial acetic acid (0.68 ml, 12 mmol) and the reaction was stirred for 16 hrs. The reaction was filtered and the filtrate evaporated in vacuo. The residue was partitioned between EtOAc and saturated NaHCO$_3$ solution and the organic extract washed with brine, dried (Na$_2$SO$_4$), and the solvent evaporated in vacuo. The residue was purified by chromatography (SiO$_2$, 2.5% MeOH in CH$_2$Cl$_2$) to provide the title compound as an oil.

$^1$HNMR(CDCl$_3$, 400 MHz) δ7.40–7.10(4H, m), 4.36(1H, s), 4.15–3.90(2H, m), 3.90–3.30(2H, m), 2.85–2.60(2H, m), 2.05–1.90(2H, m), 1.44(9H, s), 0.87(9H, s) and 0.06(6H, m) ppm.

Step I: Preparation of N-t-Butoxycarbonyl-4(R)-t-butyldimethylsilyloxy-2(S)-{N'-3-chlorobenzyl-N'-acetyl}-aminomethylpyrrolidine To a solution of N-t-butoxycarbonyl-4(R)-t-butyl-dimethylsilyloxy-2(S)-{N'-3-chlorobenzyl}-aminomethyl pyrrolidine (3.80 g, 8.35 mmol) in CH$_2$Cl$_2$ (85 ml) and triethylamine (2.40 ml, 17.0 mmol) at 0° C. was added acetyl chloride (0.60 ml, 8.44 mmol). The reaction was stirred at room temperature for 1 hr, diluted with water and extracted with CH$_2$Cl$_2$. The extracts were washed with brine, dried (Na$_2$SO$_4$) and the solvent evaporated in vacuo. The residue was purified by chromatography (SiO$_2$, 10 to 25% EtOAc in CH$_2$Cl$_2$ gradient elution).

$^1$HNMR (CDCl$_3$, 400 MHz) δ7.40–7.00(4H, m), 5.10–3,00(8H, m), 2.20–1.70(5H, m), 1.50–1.30(9H, m), 0.87(9H, s) and 0.06(6H, m) ppm.

Step J: Preparation of N-t-Butoxycarbonyl-4(R)-hydroxy-2 (S)-(N'-3-chlorobenzyl-N'-acetyl}-aminomethylpyrrolidine To a solution of N-t-butoxycarbonyl-4(R)-t-butyl-dimethylsilyloxy -2(S)-{N'-3-chlorobenzyl-N'-acetyl}-aminomethyl-pyrrolidine (4.02 g, 8.09 mmol) in THF (80 ml) at 0° C. was added tetrabutylammonium fluoride (9.00 ml of a 1M solution in THF, 9.00 mmol). The reaction was stirred at 0° C. for 1 hr and then at room temperature for 30 min. The reaction was quenched by the addition of a saturated $NH_4Cl$ solution (50 ml), dilution with EtOAc. The organic extracts were washed with brine, dried ($Na_2SO_4$) and the solvent evaporated in vacuo. The residue purified by chromatography ($SiO_2$, 3 to 5% MeOH in $CH_2Cl_2$, gradient elution) to afford the title compound as a foam.

$^1$HNMR (CDCl$_3$, 400 MHz) δ7.40–7.00(4H, m), 5.00–4,00(4H, m), 4.00–3.10(4H, m), 2.30–1.60(5H, m) and 1.50–1.30(9H, m) ppm.

Step K: N-t-Butoxycarbonyl-4(R)-benzyloxyoxy-2(S)-{N'-acetyl-N'-3-chlorobenzyl}aminomethylpyrrolidine To a solution of N-t-Butoxycarbonyl-4(S)-hydroxy-2(S)-{N'-acetyl-N'3-chlorobenzyl}aminomethylpyrrolidine (701 mg, 1.83 mmol) in DMF (9 ml) at 0° C. was added sodium hydride (110 mg of a 60% dispersion in mineral oil, 2.75 mmol). After 15 min benzyl bromide (0.435 ml, 3.66 mmol), was added and the reaction stirred at room temperature for 16 hrs. The reaction was quenched with saturated $NaHCO_3$ solution (2 ml) and extracted with ethyl acetate. The organic extract was washed with brine and dried ($Na_2SO_4$), and the solvent evaporated in vacuo. The residue was purified by chromatography ($SiO_2$, 25 to 50% EtOAc in $CH_2Cl_2$, gradient elution) to afford the title compound as a foam.

Step L: 4(S)-Benzyloxy-2(S)-{N'-acetyl-N'-3-chlorobenzyl}-aminomethylpyrrolidine hydrochloride A solution of the product from step K (0.834 g, 1.76 mmol) in EtOAc (25 ml) at 0° C. was saturated with gaseous hydrogen chloride. The resulting solution was allowed to stand at room temperature for 30 min. The solvent was evaporated in vacuo to afford the title compound as a white solid.

Step M: Preparation of 1H-Imidazole-4-acetic acid methyl ester hydrochloride.

A solution of 1H-imidazole-4-acetic acid hydrochloride (4.00 g, 24.6 mmol) in methanol (100 ml) was saturated with gaseous hydrogen chloride. The resulting solution was allowed to stand at room temperature (RT) for 18 hr. The solvent was evaporated in vacuo to afford the title compound as a white solid.

$^1$H NMR(CDCl$_3$, 400 MHz) δ8.85(1H, s),7.45(1H, s), 3.89(2H, s) and 3.75(3H, s) ppm.

Step N: Preparation of 1-(Triphenylmethyl)-1H-imidazol-4-ylacetic acid methyl ester.

To a solution of the product from Step M (24.85 g, 0.141 mol) in dimethyl formamide (DMF) (115 ml) was added triethylamine (57.2 ml, 0.412 mol) and triphenylmethyl bromide (55.3 g, 0.171 mol) and the suspension was stirred for 24 hr. After this time, the reaction mixture was diluted with ethyl acetate (EtOAc) (11) and water (350 ml). The organic phase was washed with sat. aq. $NaHCO_3$ (350 ml), dried ($Na_2SO_4$) and evaporated in vacuo. The residue was purified by flash chromatography ($SiO_2$, 0–100% ethyl acetate in hexanes; gradient elution) to provide the title compound as a white solid.

$^1$H NMR (CDCl$_3$, 400 MHz) δ7.35(1H, s), 7.31(9H, m), 7.22(6H, m), 6.76(1H, s), 3.68(3H, s) and 3.60(2H, s) ppm.

Step O: Preparation of [1-(4-cyanobenzyl)-1H-imidazol-5-yllacetic acid methyl ester.

To a solution of the product from Step N (8.00 g, 20.9 mmol) in acetonitrile (70 ml) was added bromo-p-tolunitrile (4.10 g, 20.92 mmol) and heated at 55° C. for 3 hr. After this time, the reaction was cooled to room temperature and the resulting imidazolium salt (white precipitate) was collected by filtration. The filtrate was heated at 55° C. for 18 hr. The reaction mixture was cooled to room temperature and evaporated in vacuo. To the residue was added EtOAc (70 ml) and the resulting white precipitate collected by filtration. The precipitated imidazolium salts were combined, suspended in methanol (100 ml) and heated to reflux for 30 min. After this time, the solvent was removed in vacuo, the resulting residue was suspended in EtOAc (75 ml) and the solid isolated by filtration and washed (EtOAc). The solid was treated with sat aq $NaHCO_3$ (300 ml) and $CH_2Cl_2$ (300 ml) and stirred at room temperature for 2 hr. The organic layer was separated, dried ($MgSO_4$) and evaporated in vacuo to afford the title compound as a white solid:

$^1$HNMR(CDCl$_3$, 400 MHz) δ7.65(1 H, d, J=8 Hz), 7.53 (1H, s), 7.15(1H, d, J=8 Hz), 7.04(1H, s), 5.24(2H, s), 3.62(3H, s) and 3.45(2H, s) ppm.

Step P: Preparation of (1-(4-Cyanobenzyl)-1H-imidazol-5-yl)-ethanol

To a stirred solution of the ester from step O, (1.50 g, 5.88 mmol), in methanol (20 ml) at 0° C., was added sodium borohydride (1.0 g, 26.3 mmol) portionwise over 5 minutes. The reaction was stirred at 0° C. for 1 hr and then at room temperature for an additional 1 hr. The reaction was quenched by the addition of sat.$NH_4Cl$ solution and the methanol was evaporated in vacuo. The residue was partitioned between EtOAc and sat $NaHCO_3$ solution and the organic extracts dried ($MgSO_4$), and evaporated in vacuo. The residue was purified by chromatography ($SiO_2$, 4 to 10% methanol in methylene chloride, gradient elution) to afford the title compound as a solid.

$^1$H NMR CDCl$_3$δ7.64(2H, d, J=8.2 Hz), 7.57(1H, s), 7.11(2H, d, J=8.2 Hz), 6.97(1H, s), 5.23(2H, s), 3.79(2H, t, J=6.2 Hz) and 2.66(2H, t, J=6.2 Hz) ppm.

Step Q: 1-(4-Cyanobenzyl)-imidazol-5-yl-ethylmethanesulfonate

A solution of (1-(4-Cyanobenzyl)-1H-imidazol-5-yl)-ethanol (0.500 g, 2.20 mmol) in methylene chloride (6.0 ml) at 0° C. was treated with Hunig's base (0.460 ml, 2.64 mmol) and methane sulfonyl chloride (0.204 ml, 2.64 mmol). After 2 hrs, the reaction was quenched by addition of saturated $NaHCO_3$ solution (50 ml) and the mixture was extracted with methylene chloride (50 ml), dried ($MgSO_4$) and the solvent evaporated in vacuo. The title compound was used without furthur purification.

$^1$H NMR CDCl$_3$δ7.69 (1H, s) 7.66(2H, d, J=8.2 Hz), 7.15 (2H, d, J=8.2 Hz), 7.04(1H, s), 5.24(2H, s), 4.31(2H, t, J=6.7 Hz), 2.96(3H, s), and 2.88(2H, t, J=6.6 Hz)ppm.

Step R: N {1-(4-Cyanobenzyl)-1H-imidazol-5-ylethyl}-4 (R)-benzyloxyoxy-2(S)-{N'-acetyl-N'-3-chlorobenzyl}aminomethylpyrrolidine A mixture of 4(R)-benzyloxy-2(S)-{N'-acetyl-N'-3-chlorobenzyl-aminomethyl}pyrrolidine (199 mg, 0.486 mmol), the mesylate from step Q (140 mg, 0.458 mmol), potassium carbonate (165 mg, 1.19 mmol), and sodium iodide (289 mg, 1.93 mmol) in DMF (1.5 ml), were heated at 55° C. for 16 hrs. The cooled mixture was diluted with EtOAc, washed with $NaHCO_3$ solution and brine, dried ($Na_2SO_4$) and the solvent evaporated in vacuo. The residue was purified by preparative HPLC (C-18, 95:5 to 5:95 water in acetonitrile containing 0.1% TFA, gradient elution). The title compound was obtained as a white solid after lyophillisation.

Anal. calc'd for $C_{34}H_{36}N_5O_2Cl$ 3.00 TFA, 0.85 $H_2O$: C, 51.14; H, 4.37, N, 7.45. Found: C, 51.15; H, 4.42; N, 6.86.

FAB HRMS exact mass calc'd for $C_{34}H_{37}N_5O_2Cl$ 582.263579(MH+), Found: 582.263900.

Example 10

In vitro Inhibition

Transferase Assays. Prenyl-protein transferase activity assays are carried out at 30° C. unless noted otherwise. A typical reaction contains (in a final volume of 50 μL): [³H]farnesyl diphosphate or [³H]geranylgeranyl diphosphate, Ras protein, 50 mM HEPES, pH 7.5, 5 mM MgCl₂, 5 mM dithiothreitol, 10 μM ZnCl₂, 0.1% polyethyleneglycol (PEG) (15,000–20,000 mw) and isoprenyl-protein transferase. The FPTase employed in the assay is prepared by recombinant expression as described in Omer, C. A., Kral, A. M., Diehl, R. E., Prendergast, G. C., Powers, S., Allen, C. M., Gibbs, J. B. and Kohl, N. E. (1993) *Biochemistry* 32:5167–5176. The geranylgeranyl-protein transferase-type I employed in the assay is prepared as described in U.S. Pat. No. 5,470,832, incorporated by reference. After thermally pre-equilibrating the assay mixture in the absence of enzyme, reactions are initiated by the addition of isoprenyl-protein transferase and stopped at timed intervals (typically 15 min) by the addition of 1 M HCl in ethanol (1 mL). The quenched reactions are allowed to stand for 15 m (to complete the precipitation process). After adding 2 mL of 100% ethanol, the reactions are vacuum-filtered through Whatman GF/C filters. Filters are washed four times with 2 mL aliquots of 100% ethanol, mixed with scintillation fluid (10 mL) and then counted in a Beckman LS3801 scintillation counter.

For inhibition studies, assays are run as described above, except inhibitors are prepared as concentrated solutions in 100% dimethyl sulfoxide and then diluted 20-fold into the enzyme assay mixture. Substrate conditions for inhibitor IC₅₀ determinations are as follows: FTase, 650 nM Ras-CVLS, 100 nM farnesyl diphosphate; GGPTase-I, 500 nM Ras-CAIL, 100 nM geranylgeranyl diphosphate.

Alternatively, enzymologic $K_i$ values for inhibition of either FPTase or GGPTase-I can be determined using the methodology described by I. H. Segel ("Enzyme Kinetics", pages 342–345; Wiley and Sons, New York, N.Y. (1975) and references cited therein).

Example 11

Modified In Vitro GGTase Inhibition Assay

The modified geranylgeranyl-protein transferase inhibition assay is carried out at room temperature. A typical reaction contains (in a final volume of 50 μL): [³H] geranylgeranyl diphosphate, biotinylated Ras peptide, 50 mM HEPES, pH 7.5, a modulating anion (for example 10 mM glycerophosphate or 5 mM ATP), 7 mM MgCl₂, 10 μM ZnCl₂, 0.1% PEG (15,000–20,000 mw), 2 mM dithiothreitol, and geranylgeranyl-protein transferase type I (GGTase-I). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code). Reactions are initiated by the addition of GGTase and stopped at timed intervals (typically 15 min) by the addition of 200 μL of a 3 mg/mL suspension of streptavidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. For inhibition studies with slow-binding inhibitors, GGTase and inhibitors are preincubated for one hour and reactions are initiated by the addition of peptide substrate, following methodology described by J. F. Morrison, C. T. Walsh, Adv. Enzymol. & Related Areas Mol. Biol., 61 201–301 (1988). IC₅₀ values are determined with Ras peptide near $K_M$ concentrations. Enzyme and substrate concentrations for inhibitor IC₅₀ determinations are as follows: 75 pM GGTase-I, 1.6 μM Ras peptide, 100 nM geranylgeranyl diphosphate.

Alternatively, enzymologic $K_i$ values for inhibition of GGPTase-I can be determined using the methodology described by I. H. Segel ("Enzyme Kinetics", pages 342–345; Wiley and Sons, New York, N.Y. (1975) and references cited therein).

Example 12

Cell-based In Vitro Ras Prenylation Assay

The cell lines used in this assay consist of either Rat1 or NIH₃T3 cells transformed by either viral H-ras; an N-ras chimeric gene in which the C-terminal hypervariable region of viral-H-ras was substituted with the corresponding region from the N-ras gene; or ras-CVLL, a viral-H-ras mutant in which the C-terminal exon encodes leucine instead of serine, making the encoded protein a substrate for geranylgeranylation by GGTase-I. The assay can also be performed using cell lines transformed with human H-ras, N-ras or K4B-ras. The assay is performed essentially as described in DeClue, J. E. et al., Cancer Research 51:712–717, (1991). Cells in 10 cm dishes at 50–75% confluency are treated with the test compound(s) (final concentration of solvent, methanol or dimethyl sulfoxide, is 0.1%). After 4 hours at 37° C., the cells are labeled in 3 ml methionine-free DMEM supplemented with 10% regular DMEM, 2% fetal bovine serum, 400 μCi[³⁵S]methionine (1000 Ci/mmol) and test compound (s). Cells treated with lovastatin, a compound that blocks Ras processing in cells by inhibiting the rate-limiting step in the isoprenoid biosynthetic pathway (Hancock, J. F. et al. *Cell*, 57:1167 (1989); DeClue, J. E. et al. *Cancer Res.*, 51:712 (1991); Sinensky, M. et al. *J. Biol. Chem.*, 265:19937 (1990)), serve as a positive control in this assay. After an additional 20 hours, the cells are lysed in 1 ml lysis buffer (1% NP40/20 mM HEPES, pH 7.5/5 mM MgCl₂/1 mM DTT/10 mg/ml aprotinen/2 mg/ml leupeptin/2 mg/ml antipain/0.5 mM PMSF) and the lysates cleared by centrifugation at 100,000 ×g for 45 min. Alternatively, four hours after the addition of the labeling media, the media is removed, the cells washed, and 3 ml of media containing the same or a different test compound added. Following an additional 16 hour incubation, the lysis is carried out as above. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., J. Virol. 43:294–304, (1982)). Following a 2 hour antibody incubation at 4° C., 200 μl of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to prenylated and nonprenylated Ras proteins are compared to determine the percent inhibition of prenyl transfer to protein.

Example 13

Cell-based in vitro anchorage independent growth assay (SALSA)

SALSA (Soft Agar-Like Surrogate Assay) measures the inhibition of anchorage-independent growth by prenyl-transferase inhibitors. Only transformed cells are able to grow anchorage-independently in the SALSA format. Additionally, cells growing in the SALSA format grow in clumps, resembling the colonies formed in soft agar. SALSA may been used to measure the growth inhibition by prenyl-transferase inhibitors in a variety of transformed cell lines, including Rat1 fibroblasts transformed with viral-H-ras (H-ras/rat1), as well as a panel of human tumor cell lines (HTL3 s).

SALSA is performed in 96-well plates that are coated with a thin film of the polymer, PolyHEMA (Poly(2-hydroxyethyl methacrylate)), which prevents cells from attaching to the plate. Rat1 fibroblast cells transformed with v-Ha-ras (this cell line has been deposited in the ATCC on Aug. 19, 1997 under the terms of the Budapest convention and has been given a designation of ATCC CRL-12387) are seeded at 5000 cells/well, grown for 4 hr, then vehicle or half-log dilutions of test compound (in either an 8 or 12 point titration) are added. The cells are then grown for 6 days at 37 degrees, without changing the growth media or adding fresh compound. At day 6, cell growth is assessed via a colorimetric assay that measures the cleavage of the tetrazolium dye, MTT, to an insoluble purple formazan, a reaction dependent upon mitochondrial dehydrogenases. At day 6, the cells are incubated for 4 hr with 0.5 mg/ml MTT, and then SDS is added to 9% w/v to lyse the cells and solubilize the insoluble MTT-formazan. The amount of MTT metabolism is quantitated via spectrophotometric detection at 570 nM. Dose-inhibition curves and $IC_{50}$'s are determined.

Example 15

In vivo tumor growth inhibition assay (nude mouse)

In vivo efficacy as an inhibitor of the growth of cancer cells may be confirmed by several protocols well known in the art. Examples of such in vivo efficacy studies are described by N. E. Kohl et al. (*Nature Medicine*, 1:792–797 (1995)) and N. E. Kohl et al. (*Proc. Nat. Acad. Sci. U.S.A.*, 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle, compound or combination treatment group. Animals are dosed subcutaneously starting on day 1 and daily for the duration of the experiment. Alternatively, the farnesyl-protein transferase inhibitor may be administered by a continuous infusion pump. Compound, compound combination or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:

1. An assay for identifying a compound that inhibits geranylgeranyl-protein transferase type I activity, comprising:
   a) reacting a protein or peptide substrate comprising a $CAAX^G$ motif with geranylgeranyl pyrophosphate and geranylgeranyl-protein transferase type I in the presence of a test compound and further in the presence of a modulating anion;
   b) detecting whether the geranylgeranyl residue is incorporated into the protein or peptide substrate, in which the ability of the test compound to inhibit geranylgeranyl-protein transferase type I activity is indicated by a decrease in the incorporation of the geranylgeranyl residue into the protein or peptide substrate as compared to the amount of the geranylgeranyl residue incorporated into the protein or peptide substrate in the absence of the test compound.

2. The assay according to claim 1 for identifying a compound that inhibits in vivo geranylgeranyl-protein transferase type I activity.

3. The assay according to claim 1 wherein the modulating anion is a phosphate or sulfate containing anion.

4. The assay according to claim 3 wherein the modulating anion is selected from the group consisting of: adenosine 5'-triphosphate (ATP), 2'-deoxyadenosine 5'-triphosphate, 2'-deoxycytosine 5'-triphosphate, β-glycerol phosphate, pyrophosphate, guanosine 5'-triphosphate, 2'-deoxyguanosine 5'-triphosphate, uridine 5'-triphosphate, dithiophosphate, thymidine 5'-triphosphate, tripolyphosphate, D-myo-inositol 1,4,5-triphosphate and sulfate.

5. The assay according to claim 4 wherein the modulating anion is selected from the group consisting of: adenosine 5'-tinphosphate (ATP), β-glycerol phosphate, pyrophosphate, dithiophosphate and sulfate.

6. The assay according to claim 4 wherein the concentration of the modulating anion in the assay is selected from a range of from about 0.1 mM to about 100 mM.

7. The assay according to claim 4 wherein the concentration of the modulating anion in the assay is selected from a range of from about 1 mM to about 10 mM.

8. The assay according to claim 1 wherein the $CAAX^G$ motif is selected from the group consisting of: CVIM, CVLL.

9. The assay according to claim 8 wherein the $CAAX^G$ motif is CVIM.

10. A method for identifying a prenyl-protein transferase inhibitor which is efficacious in vivo as an inhibitor of geranylgeranyl-protein transferase type I which comprises the steps of:
    a) assessing a test compound for its in vitro inhibitory activity against transfer of a geranylgeranyl residue to a protein or peptide substrate comprising a $CAAX^G$ motif by geranylgeranyl-protein transferase type I in the presence of a modulating anion;
    b) assessing the test compound for its in vitro inhibitory activity against said transfer of a geranylgeranyl residue in the absence of a modulating anion; and
    c) comparing the inhibitory activity of the test compound in the assessment of step a) with the inhibitory activity of the test compound in the assessment of step b).

11. The method according to claim 10 wherein the prenyl-protein transferase inhibitor is a dual inhibitor of farnesyl-protein transferase and geranylgeranyl-protein transferase type I.

* * * * *